US011781955B2

(12) United States Patent
Kobayashi et al.

(10) Patent No.: US 11,781,955 B2
(45) Date of Patent: *Oct. 10, 2023

(54) PHOTO-CONTROLLED REMOVAL OF TARGETS IN VITRO AND IN VIVO

(71) Applicant: The United States of America, as represented by the Secretary, Department of Health and Human Services, Bethesda, MD (US)

(72) Inventors: Hisataka Kobayashi, Laurel, MD (US); Peter Choyke, Rockville, MD (US); Martin John Schnermann, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 314 days.

This patent is subject to a terminal disclaimer.

(21) Appl. No.: 17/026,724

(22) Filed: Sep. 21, 2020

(65) Prior Publication Data

US 2021/0010914 A1    Jan. 14, 2021

Related U.S. Application Data

(63) Continuation of application No. 15/318,104, filed as application No. PCT/US2015/044168 on Aug. 7, 2015, now Pat. No. 10,830,678.
(Continued)

(51) Int. Cl.
*G01N 1/44* (2006.01)
*A61K 47/68* (2017.01)
(Continued)

(52) U.S. Cl.
CPC ............ *G01N 1/44* (2013.01); *A61K 41/0071* (2013.01); *A61K 47/6891* (2017.08);
(Continued)

(58) Field of Classification Search
CPC ...... G01N 33/5002; G01N 1/405; G01N 1/44; A61K 49/0036; A61K 47/6891;
(Continued)

(56) References Cited

U.S. PATENT DOCUMENTS 2,915,392 A   12/1959  Pedersen
5,196,005 A    3/1993  Doiron et al.
(Continued)

FOREIGN PATENT DOCUMENTS

CN   102585003       7/2012
CN   104203286 A    12/2014
(Continued)

OTHER PUBLICATIONS

Nakaya and Kurata, "Possibility of Immunotherapy in combination with cytotoxic chemotherapy/radiotherapy," *Journal of Molecular Targeted Therapy for Cancer* 13(4): 438-442, 2016.
(Continued)

*Primary Examiner* — Shafiqul Haq
(74) *Attorney, Agent, or Firm* — Klarquist Sparkman, LLP

(57) ABSTRACT

This disclosure provides IR700-molecule conjugates and methods of their use to remove (e.g., separate or isolate) a target from a sample in vivo or from a subject in vitro. It is shown herein that exposure of IR700 to near infrared (NIR) light removes a portion of IR700, changing it from a hydrophilic molecule, to one that is hydrophobic, resulting in aggregation of IR700 and anything bound to it. For example, the disclosed IR700-molecule conjugates and methods provide photo-controlled ways to control the phar-
(Continued)

macokinetics of a drug in vivo, and can be used to remove undesired agents from environmental or food samples or to isolate target molecules in a laboratory.

22 Claims, 35 Drawing Sheets

Related U.S. Application Data

(60) Provisional application No. 62/034,990, filed on Aug. 8, 2014.

(51) Int. Cl.
*A61K 49/00* (2006.01)
*A61K 41/00* (2020.01)
*A61N 5/06* (2006.01)
*G01N 1/40* (2006.01)
*G01N 33/50* (2006.01)

(52) U.S. Cl.
CPC .......... *A61K 49/0036* (2013.01); *A61N 5/062* (2013.01); *G01N 1/405* (2013.01); *G01N 33/5002* (2013.01); *A61N 2005/0651* (2013.01); *A61N 2005/0663* (2013.01)

(58) Field of Classification Search
CPC ...... A61K 41/0071; A61P 39/02; A61P 35/00; A61N 5/062; A61N 2005/0663; A61N 2005/0651
See application file for complete search history.

(56) References Cited

U.S. PATENT DOCUMENTS

| | | |
|---|---|---|
| 5,494,793 A | 2/1996 | Schindele et al. |
| 6,344,050 B1 | 2/2002 | Chen |
| 6,534,041 B1 | 3/2003 | Licha et al. |
| 7,005,518 B2 | 2/2006 | Peng et al. |
| 7,498,029 B2 | 3/2009 | Hasan et al. |
| 8,524,239 B2 | 9/2013 | Kobayashi et al. |
| 8,623,354 B2 | 1/2014 | Brown et al. |
| 9,358,306 B2 | 6/2016 | Kobayashi et al. |
| 9,538,306 B2 | 1/2017 | Nakamura |
| 10,537,641 B2 | 1/2020 | Kobayashi et al. |
| 10,538,590 B2 | 1/2020 | Kobayashi et al. |
| 11,013,803 B2 | 5/2021 | Kobayashi et al. |
| 11,364,297 B2 | 6/2022 | Kobayashi et al. |
| 11,364,298 B2 | 6/2022 | Kobayashi et al. |
| 2001/0044124 A1 | 11/2001 | Bacus |
| 2004/0120949 A1 | 6/2004 | Adolf et al. |
| 2005/0147612 A1 | 7/2005 | Yayon |
| 2005/0157292 A1 | 7/2005 | Saitoh et al. |
| 2006/0188509 A1 | 8/2006 | Derynck et al. |
| 2006/0231107 A1 | 10/2006 | Glickman et al. |
| 2007/0020272 A1 | 1/2007 | Hasan |
| 2007/0133086 A1 | 6/2007 | Wilhelm et al. |
| 2008/0073566 A1 | 3/2008 | Frangioni |
| 2008/0095699 A1 | 4/2008 | Zheng et al. |
| 2008/0095950 A1 | 4/2008 | Hall-Goulle et al. |
| 2008/0253960 A1 | 10/2008 | Zheng et al. |
| 2010/0215575 A1 | 8/2010 | O'Neill et al. |
| 2010/0255057 A1 | 10/2010 | Hyde et al. |
| 2011/0082412 A1 | 4/2011 | Hyde et al. |
| 2011/0288234 A1 | 11/2011 | Pandey et al. |
| 2012/0010558 A1 | 1/2012 | Kobayashi et al. |
| 2012/0070377 A1 | 3/2012 | Yahioglu et al. |
| 2012/0070853 A1 | 3/2012 | Johansen et al. |
| 2012/0122094 A1 | 5/2012 | May et al. |
| 2013/0287688 A1 | 10/2013 | Jain et al. |
| 2013/0336995 A1 | 12/2013 | Kobayashi et al. |
| 2014/0120119 A1 | 5/2014 | Kobayashi et al. |
| 2014/0309578 A1 | 10/2014 | Anvari |
| 2015/0140022 A1 | 5/2015 | Barth et al. |
| 2015/0343060 A1 | 12/2015 | Kovar et al. |
| 2015/0343084 A1 | 12/2015 | Dilley |
| 2015/0374819 A1 | 12/2015 | Kovar |
| 2016/0015829 A1 | 1/2016 | Kobayashi et al. |
| 2016/0228568 A1 | 8/2016 | de los Pinos et al. |
| 2016/0256564 A2 | 9/2016 | Kobayashi et al. |
| 2017/0122853 A1 | 5/2017 | Kobayashi et al. |
| 2018/0113246 A1 | 4/2018 | Rose et al. |
| 2018/0113247 A1 | 4/2018 | Rose et al. |
| 2018/0236076 A1 | 8/2018 | Kobayashi et al. |
| 2018/0239074 A1 | 8/2018 | Rose et al. |
| 2018/0250405 A1 | 9/2018 | Biel et al. |
| 2019/0015510 A1 | 1/2019 | Makings et al. |
| 2019/0282696 A1 | 9/2019 | Biel et al. |
| 2019/0365897 A1 | 12/2019 | Garcia-Guzman et al. |
| 2020/0085950 A1 | 3/2020 | Kobayashi et al. |
| 2020/0095331 A1 | 3/2020 | Kobayashi et al. |
| 2021/0079112 A1 | 3/2021 | Kobayashi et al. |
| 2022/0288210 A1 | 9/2022 | Kobayashi et al. |
| 2023/0050584 A1 | 2/2023 | Kobayashi et al. |

FOREIGN PATENT DOCUMENTS

| | | |
|---|---|---|
| DE | 197 17 904 A1 | 10/1998 |
| EP | 1512963 A1 | 3/2005 |
| EP | 2731626 B1 | 12/2018 |
| JP | 2003-284757 A | 10/2003 |
| JP | 2003-344284 A | 12/2003 |
| JP | 2006-515892 A | 6/2006 |
| JP | 2006-517230 A | 7/2006 |
| JP | 2007-155722 A | 6/2007 |
| WO | WO 2000/062807 A1 | 10/2000 |
| WO | WO 2001/057495 | 8/2001 |
| WO | WO 2003/011106 A2 | 2/2003 |
| WO | WO 2003/032900 A2 | 4/2003 |
| WO | WO 2003/083811 A1 | 10/2003 |
| WO | WO 2004/038378 A2 | 5/2004 |
| WO | WO 2004/067038 A1 | 8/2004 |
| WO | WO 2004/071571 A1 | 8/2004 |
| WO | WO 2005/099689 | 10/2005 |
| WO | WO 2006/092598 A2 | 9/2006 |
| WO | WO 2007/070680 A2 | 6/2007 |
| WO | WO 2008/005942 A2 | 1/2008 |
| WO | WO 2008/120134 A1 | 10/2008 |
| WO | WO 2008/152424 | 12/2008 |
| WO | WO 2009/038776 | 3/2009 |
| WO | WO 2009/079024 A1 | 6/2009 |
| WO | WO 2009/092062 | 7/2009 |
| WO | WO 2009/107139 A1 | 9/2009 |
| WO | WO 2010/047611 A1 | 4/2010 |
| WO | WO 2010/085651 A1 | 7/2010 |
| WO | WO 2010/121163 | 10/2010 |
| WO | WO 2011/014726 A1 | 2/2011 |
| WO | WO 2011/025950 | 3/2011 |
| WO | WO 2011/038006 | 3/2011 |
| WO | WO 2011/123742 A1 | 10/2011 |
| WO | WO 2012/076631 | 6/2012 |
| WO | WO 2012/082118 | 6/2012 |
| WO | WO 2013/009475 A1 | 1/2013 |
| WO | WO 2013/044156 | 3/2013 |
| WO | WO 2014/084394 A1 | 6/2014 |
| WO | WO 2014/089247 | 6/2014 |
| WO | WO 2014/127365 | 8/2014 |
| WO | WO 2014/168950 | 10/2014 |
| WO | WO 2015/057692 | 4/2015 |
| WO | WO 2015/187651 | 12/2015 |
| WO | WO 2015/187677 | 12/2015 |
| WO | WO 2016/022896 A1 | 2/2016 |
| WO | WO 2017/027247 A1 | 2/2017 |
| WO | WO 2017/031363 | 2/2017 |
| WO | WO 2017/031367 A1 | 2/2017 |
| WO | WO 2018/080952 | 5/2018 |
| WO | WO 2018/156815 | 8/2018 |

(56) References Cited

FOREIGN PATENT DOCUMENTS

WO WO 2019/009941 1/2019
WO WO 2019/199751 A1 10/2019

OTHER PUBLICATIONS

Wooldridge et al.., "Immunostimulatory Oligodeoxynucleotides Containing CpG Motifs Enhance the Efficacy of Monoclonal Antibody Therapy of Lymphoma," Blood 89:2994-2998, 1997.
PCT/US2022/014448 International Search Report and Written Opinion dated May 13, 2022 (14 pages).
Ali et al., "Dynamic fluorescent imaging with indocyanine green for monitoring the therapeutic effects of photoimmunotherapy," Contrast Media Mol Imaging 9(4):276-282, 2014.
Amoury et al., "Photoimmunotheranostic agents for triple-negative breast cancer diagnosis and therapy that can be activated on demand," Oncotarget 7(34):54925-54936, 2016.
Anonymous, "Anodyne: Tratamento com tecnologia MIRE," Forumenfermagem-Projecto Feridas, Jan. 24, 2011, XP002686605, retrieved from the internet: URL:http://forumenfermagem.org/feridas/?s=anodyne, retrieved on Nov. 7, 2012.
Anonymous, "Near Infrared Light for the Treatment of Painful Peripheral Neuropathy," U.S. National Institutes of Health, Aug. 2, 2012, XP002686617, retrieved from the internet: URL:http://www.clinicaltrials.gov/ct2/show/NCT00125268, retrieved on Nov. 7, 2011.
Anonymous, "Near IR Signature Management for Combat Clothing and Equipment," Australian Government Department of Defence, DSTO, Apr. 7, 2005, XP002686606, retrieved from the internet: URL:http://www.dsto.defence.gov.au/reserach/3214/?print=true, retrieved on Nov. 6, 2012.
Ballou et al., "Tumor Labeling in Vivo Using Cyanine-Conjugated Monoclonal Antibodies," Cancer Immunol. Immunother. 41:257-263, 1995.
Baolin et al., Practical Pathophysiology, Qing Dao Ocean University Press, Dec. 1995.
Barrett et al., "In vivo Diagnosis of Epidermal Growth Factor Receptor Expression using Molecular Imaging with a Cocktail of Optically Labeled Monoclonal Antibodies," Clin Cancer Res. 13:6639-6648, 2007.
Carcenac et al., "Internalisation enhances photo-induced cytotoxicity of monoclonal antibody-phthalocyanine conjugates." Br J. Cancer 85:1787-1793, 2001.
Carter et al., "Identification and Validation of Cell Surface Antigens for Antibody Targeting in Oncology," Endocr Relat Cancer 11:659-687, 2004.
Chen et al., "Tumor vascular permeabilization by vascular-targeting photosensitization: effects, mechanism, and therapeutic implications," Clin Cancer Res. 12:917-923, 2006.
Chiarello, K., "In between the light and the dark: developments in Photosensitive Pharmaceuticals," Pharmaceutical Technology, pp. 48-54, Dec. 2004.
Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].
Clinical Trial Identifier NCT02422979, first posted on Apr. 22, 2015, last updated on Sep. 20, 2019 (9 pages).
Davis et al., "Nanoparticle Therapeutics: an Emerging Treatment Modality for Cancer," Nat Rev Drug Dis. 7:771-782, 2008.
De Boer et al., "A standardized light-emitting diode device for photoimmunotherapy," J Nucl Med. 55(11):1893-1898, 2014.
De Boer et al., "Biodistribution Study of Intravenously Injected Cetuximab-IRDye700DX in Cynomolgus Macaques," Mol Imaging Biol. 18(2):232-242, 2016.
Del Governatore et al., "Experimental Photoimmunotherapy of Hepatic Metastases of Colorectal Cancer with a 17.1A chlorin$_{e6}$ Immunoconjugate," Cancer Res. 60:4200-4205, 2000.

Denis et al., "Synthesis, bioanalysis and biodistribution of photosensitizer conjugates for photodynamic therapy," Bioanalysis 5:1099-1114, 2013.
Dixit et al., "Transferrin Receptor-Targeted Theranostic Gold Nanoparticles for Photosensitizer Delivery in Brain Tumors," Nanoscale, 7(5):1782-1790, 2015.
Doane et al., "Observation and Photophysical Characterization of Silicon Phthalocyanine J-Aggregate Dimers in Aqueous Solutions," Chem Eur J. 20:8030-8039, 2014.
Dougherty et al., "Photodynamic Therapy," J Natl Cancer Inst. 90:889-905, 1998.
Duska et al., Combination Photoimmunotherapy and Cisplatin: Effects on Human Ovarian Cancer Ex Vivo, J Nat Cancer Inst. 91:1557-1563, 1999.
Gajewski et al., "The P815 Mastocytoma Tumor Model," Curr Protoc Immunol. 43:20.4.1-20.4.18, 2001.
Gao et al., "In vivo Cancer Targeting and Imaging With Semiconductor Quantum Dots," Nat Biotechnol. 22:969-976 and 5 pages of supplemental notes, 2004.
Gleysteen et al.,"Fluorescently labeled cetuximab to evaluate head and neck cancer response to treatment," Cancer Biol Ther. 6:e1-e5, 2007.
Greish, Khaled, "Enhanced permeability and retention of macromolecular drugs in solid tumors: a royal gate for targeted anticancer nanomedicines," J Drug Target. 15:457-464, 2007.
Hanaoka et al., "Glypican-3 targeted human heavy chain antibody as a drug carrier for hepatocellular carcinoma therapy," Mol Pharm. 12(6):2151-2157, 2015.
Hanaoka et al., "Photoimmunotherapy of hepatocellular carcinoma-targeting Glypican-3 combined with nanosized albumin-bound paclitaxel," Nanomedicine (Lond). 10(7):1139-1147, 2015.
Heukers et al., "Nanobody-photosensitizer conjugates for targeted photodynamic therapy," Nanomedicine 10:1441-1451, 2014.
Hiroshima et al., "Photoimmunotherapy Inhibits Tumor Recurrence After Surgical Resection on a Pancreatic Cancer Patient-Derived Orthotopic Xenograft (PDOX) Nude Mouse Model," Ann Surg Oncol. 22 Suppl 3:S1469-S1474, 2015.
Iqbal et al., "Phthalocyanine-Biomolecule Conjugated Photosensitizers for Targeted Photodynamic Therapy and Imaging," Curr Drug Metab. 16(9):816-832, 2015.
Ishida et al., "Trastuzumab-Based Photoimmunotherapy Integrated with Viral HER2 Transduction Inhibits Peritoneally Disseminated HER2-Negative Cancer," Mol Cancer Ther. 15(3):402-411, 2016.
Ishii et al., "Defucosylated Humanized Anti-CCR4 Monoclonal Antibody KW-0761 as a Novel Immunotherapeutic Agent for Adult T-cell Leukemia/Lymphoma," Clin Cancer Res. 16:1520-1531, 2010.
Ito et al., "Combination photoimmunotherapy with monoclonal antibodies recognizing different epitopes of human epidermal growth factor receptor 2: an assessment of phototherapeutic effect based on fluorescence molecular imaging," Oncotarget 7:14143-14152, 2016.
Ito et al., "Molecular targeted photoimmunotherapy for HER2-positive human gastric cancer in combination with chemotherapy results in improved treatment outcomes through different cytotoxic mechanisms," BMC Cancer 16:37, 2016.
Jia et al., "Cannabinoid CB2 receptor as a new phototherapy target for the inhibition of tumor growth," Mol Pharm. 11(6):1919-1929, 2014.
Jing et al., "Imaging and Selective Elimination of Glioblastoma Stem Cells with Theranostic Near-Infrared-Labeled CD133-Specific Antibodies," Theranostics 6(6):862-874, 2016.
Kijanka et al., "Optical imaging of pre-invasive breast cancer with a combination of VHHs targeting CAIX and HER2 increases contrast and facilitates tumour characterization," EJNMMI Res. 6(1):14, 2016.
Kines et al., "HPV Based Photodynamic Therapy: a New Approach for Anti-Cancer Therapy," J. Immunol. 192(1): Supplement 206.8, 2014.
Kirveliene et al., "Schedule-Dependent Interaction Between Doxorubicin and mTHPC-Mediated Photodynamic Therapy in Murine Hepatoma in Vitro and in Vivo," Cancer Chemother. Pharmacol. 57:65-72, 2005.

(56) References Cited

OTHER PUBLICATIONS

Kishimoto et al., "Evaluation of oxygen dependence on in vitro and in vivo cytotoxicity of photoimmunotherapy using IR-700-antibody conjugates," *Free Radic Biol Med.* 85:24-32, 2015.
Kobayashi, "Activatable Fluorescent Imaging Probes for Cancer Detection and Diagnosis," Abstract presented at the American Chemical Society meeting in San Francisco, 2014.
Kobayashi, "Near infrared photoimmunotherapy: a new cancer therapy kills cancer cells with the exposure of harmless near infrared light," Poster Presentation, at NEST Conference, Tokyo, Japan, Apr. 2018.
Kovar et al., "A Systematic Approach to the Development of Fluorescent Contrast Agents for Optical Imagining of Mouse Cancer Models," *Anal. Biochem.* 367:1-12, 2007.
Li-Cor, "IRDye® Infrared Dyes: Advancing Discovery with Infrared Imaging," 2010.
Li-Cor, "High Photostability of IRDye® 700DX," Retrieved on Aug. 23, 2018. Retrieve on https://www.licor.comlbio/products/reagents/irdye/700dx/photostability.html.
Maawy et al., "Near infra-red photoimmunotherapy with anti-CEA-IR700 results in extensive tumor lysis and a significant decrease in tumor burden in orthotopic mouse models of pancreatic cancer," *PLoS One* 10(3):e0121989, 2015.
Maawy et al., "Photoimmunotherapy lowers recurrence after pancreatic cancer surgery in orthotopic nude mouse models," *J Surg Res.* 197:5-11, 2015.
Maruoka et al., "Combined CD44- and CD25-targeted Near-Infrared Photoimmunotherapy to Selectively Kill Cancer and Regulatory T cells in Syngeneic Mouse Cancer Models," *Cancer Immunol Res.* 8:345-355, 2020.
Maya et al., "Synthesis, Aggregation Behavior and Nonlinear Absorption Properties of Lead Phthalocyanines Substituted with Siloxane Chains," *J Materials Chem.* 13:1603-1613, 2003.
McHugh et al., "The role of suppressor T cells in regulation of immune responses," *J Allergy Clin Immunol.* 110:693-702, 2002.
Mitchell et al., "Comparison of Two Infrared Devices in Their Effectiveness in Reducing Symptoms Associated with RLS," Physiother. Theory Prac., 2011, XP002686651, retrieved from the internet: URL:http://www.ncbi.nlm.nih.gov.pubmed/20950168, retrieved on Nov. 8, 2012.
Mitchell et al., "Comparison of Two Infrared Devices in Their Effectiveness in Reducing Symptoms Associated with RLS," *Physiother. Theory Pract.* 27:352-359, 2011.
Mitsunaga et al., "Cancer Cell-Selective in Vivo Near Infrared Photoimmunotherapy Targeting Specific Membrane Molecules," *Nat Med.* 17:1685-1691, 2011.
Mitsunaga et al., "Abstract 3618: Target-Specific Photo-Activatable Immunotherapy (PIT) for Cancer Based on a Monoclonal Antibody-Photosensitizer Conjugate," in *Proceedings of the 102nd Annual Meeting of the American Association for Cancer Research*; Apr. 2-6, 2011; Orlando, FL. Philadelphia (PA): AACR; Cancer Res. 71:3618, 2011.
Mitsunaga et al., "Immediate in vivo target-specific cancer cell death after near infrared photoimmunotherapy," *BMC Cancer.* 12:345, 2012.
Mitsunaga et al., "Near-Infrared Theranostic Photoimmunotherapy (PIT): Repeated Exposure of Light Enhances the Effect of Immunoconjugate," *Bioconjug Chem.* 23:604-609, 2012.
Moore et al., "Photoimmunotherapy of residual disease after incomplete surgical resection in head and neck cancer models," *Cancer Med.* 5(7):1526-1534, 2016.
Nagaya et al., "Host Immunity Following Near-Infrared Photoimmunotherapy Is Enhanced with PD-1 Checkpoint Blockade to Eradicate Established Antigenic Tumors," Cancer Immunol Res. 7:401-413, 2019.
Nagaya et al., "Near Infrared Photoimmunotherapy Targeting EGFR Positive Triple Negative Breast Cancer: Optimizing the Conjugate-Light Regimen," *PLoS One* 10(8):e0136829, 2015.
Nagaya et al., "Near infrared photoimmunotherapy with an anti-mesothelin antibody," *Oncotarget* 7(17):23361-23369, 2016.
Nagaya et al., "Near infrared photoimmunotherapy of B-cell lymphoma," *Mol Oncol.* 10:1404-1414, 2016.
Nagaya et al., "Improved micro-distribution of antibody-photon absorber conjugates after initial near infrared photoimmunotherapy (NIR-PIT)," *J Control Release* 232:1-8, 2016.
Nagaya et al., "Near infrared photoimmunotherapy with avelumab, an anti-programmed death-ligand 1 (PD-L1) antibody," Oncotarget 8:8807-8817, 2017.
Nagaya et al., "Syngeneic Mouse Models of Oral Cancer Are Effectively Targeted by Anti-CD44-Based NIR-PIT," *Mol Cancer Res.* 15:1667-1677, 2017.
Nagaya et al., "Near infrared photoimmunotherapy targeting bladder cancer with a canine anti-epidermal growth factor receptor (EGFR) antibody," Oncotarget 9:19026-19038, 2018.
Nakajima et al., "Real-time monitoring of in vivo acute necrotic cancer cell death induced by near infrared photoimmunotherapy using fluorescence lifetime imaging," *Cancer Res.* 72(18):4622-4628, 2012.
Nakajima et al., "Improving the Efficacy of Photoimmunotherapy (PIT) Using a Cocktail of Antibody Conjugates in a Multiple Antigen Tumor Model," *Theranostics* 3:357-365, 2013.
Nakajima et al., "The effects of conjugate and light dose on photo-immunotherapy induced cytotoxicity," *BMC Cancer* 30;14:389, 2014.
Nakamura et al., "MR imaging biomarkers for evaluating therapeutic effects shortly after near infrared photoimmunotherapy," *Oncotarget* 7(13):17254-17264, 2016.
Nowis et al., "The influence of photodynamic therapy on the immune response," *Photodiagnosis Photodyn Ther.* 2:283-298, 2005.
Ogawa et al., "In vivo Molecular Imaging of Cancer with a Quenching Near-Infrared Fluorescent Probe Using Conjugates of Monoclonal Antibodies and Indocyanine Green," *Cancer Res.* 69:1268-1272, 2009.
Peng et al., "Phthalocyanine dye as an extremely photostable and highly fluorescent near-infrared labeling reagent," *Proc. SPIE, Optical Molecular Probes for Biomedical Applications*, 60970E (Feb. 14, 2006) (12 pages).
Rosas-Arellano et al., "A simple solution for antibody signal enhancement in immunofluorescence and triple immunogold assays," *Histochem Cell Biol.* 146:421-430, 2016.
Rosenthal et al., "In Vivo Detection of Head and Neck Cancer Orthotopic Xenografts by Immunofluorescence," *Laryngoscope* 116:1636-1641, 2006.
Sanchez-Barcelo et al., "Recent Patents on Light Based Therapies: Photodynamic Therapy, Photothermal Therapy and Photoimmunotherapy," *Recent Patents on Endocrine, Metabolic & Immune Drug Discovery* 8:1-8, 2014.
Sano et al., "Acute cytotoxic effects of photoimmunotherapy assessed by 18F-FDG PET," *J Nucl Med.* 54(5):770-775, 2013.
Sano et al., "Markedly Enhanced Permeability and Retention Effects Induced by Photo-Immunotherapy of Tumors," ACS Nano. 7:717-724, 2013, including 19 pages of supporting information).
Sano et al., "The effect of photoimmunotherapy (PIT) followed by liposomal daunorubicin in a mixed tumor model: a demonstration of the super-enhanced permeability and retention (SUPR) effect after PIT," *Mol Cancer Ther.* 13(2):426-432, 2014.
Sato et al., "Photoimmunotherapy: comparative effectiveness of two monoclonal antibodies targeting the epidermal growth factor receptor," *Mol Oncol.* 8(3):620-632, 2014.
Sato et al., "Photoimmunotherapy of gastric cancer peritoneal carcinomatosis in a mouse model," *PLoS One* 9(11):e113276, 2014.
Sato et al., "Near infrared photoimmunotherapy for lung metastases," *Cancer Lett.* 365(1):112-121, 2015.
Sato et al., "Near infrared photoimmunotherapy in the treatment of disseminated peritoneal ovarian cancer," *Mol Cancer Ther.* 14(1):141-150, 2015.
Sato et al., "Near infrared photoimmunotherapy in the treatment of pleural disseminated NSCLC: preclinical experience," *Theranostics* 5(7):698-709, 2015.
Sato et al., "Selective cell elimination in vitro and in vivo from tissues and tumors using antibodies conjugated with a near infrared phthalocyanine," *RSC Adv.* 5(32):25105-25114, 2015.

(56) References Cited

OTHER PUBLICATIONS

Sato et al., "Comparative effectiveness of light emitting diodes (LEDs) and Lasers in near infrared photoimmunotherapy," *Oncotarget* 7(12):14324-14335, 2016.

Sato et al., "Spatially selective depletion of tumor-associated regulatory T cells with near-infrared photoimmunotherapy," *Sci Transl Med.* 8:352ra110, 2016.

Sato et al., "Photoinduced Ligand Release from a Silicon Phthalocyanine Dye Conjugated with Monoclonal Antibodies: a Mechanism of Cancer Cell Cytotoxicity after Near-Infrared Photoimmunotherapy," *ACS Cent Sci.* 4:1559-1569, 2018.

Savellano et al., "Multiepitope HER2 Targeting Enhances Photoimmunotherapy of HER2-Overexpressing Cancer Cells with Pyropheophorbide-a Immunoconjugates," *Cancer Res.* 65:6371-6379, 2005.

Scully et al., "Application of Fluorescence Lifetime Imaging Microscopy to the Investigation of Intracellular PDT Mechanisms," *Bioimaging* 5:9-18, 1997.

Serebrovskaya et al., "Targeting Cancer Cells by Using an Antireceptor Antibody-Photosensitizer Fusion Protein," *Proc Nat Acad Sci.* 106:9221-9225, 2009.

Serebrovskaia et al., "Genetically Encoded Photoimmunosensitizer," *Bioorg. Khim.* 37:137-144, 2011 (English Abstract Only).

Shimoyama et al., "Viral transduction of the HER2-extracellular domain expands trastuzumab-based photoimmunotherapy for HER2-negative breast cancer cells," *Breast Cancer Res Treat.* 149(3):597-605, 2015.

Shirasu et al., "Potent and specific antitumor effect of CEA-targeted photoimmunotherapy," *Int J Cancer.* 135(11):2697-710, 2014.

Snyder et al., "Photodynamic therapy: a means to enhanced drug delivery to tumors," *Cancer Res.* 63:8126-8131, 2003.

Soukos et al., "Epidermal Growth Factor Receptor-Targeted Immunophotodiagnosis and Photoimmunotherapy of Oral Precancer in Vivo," *Cancer Res.* 61:4490-4496, 2001.

Steele et al., "Suppressor deletion therapy: selective elimination of T suppressor cells in vivo using a hematoporphyrin conjugated monoclonal antibody permits animals to reject syngeneic tumor cells," *Cancer Immunol Immunother.* 26:125-131, 1988.

Sugiyama et al, "Anti-CCR4 mAb selectively depletes effector-type FoxP3+CD4+ regulatory T cells, evoking antitumor immune responses in humans," *Proc Natl Acad Sci. USA* 110:17945-17950, 2013.

Supplementary materials from Mitsunaga et al., "Cancer Cell-Selective in Vivo Near Infrared Photoimmunotherapy Targeting Specific Membrane Molecules," *Nat. Med.* 17:1685-1691, 2011.

Supplementary materials from Sugiyama et al., "Anti-CCR4 mAb selectively depletes effector-type FoxP3+CD4+ regulatory T cells, evoking antitumor immune responses in humans," *Proc Natl Acad Sci. USA* 110:17945-17950, 2013. (5 pages).

van Dongen et al., "Photosensitizer-Antibody Conjugates for Detection and Therapy of Cancer," *Adv Drug Deliv Rev.* 56:31-52, 2004.

Van Driel et al., "EGFR targeted nanobody-photosensitizer conjugates for photodynamic therapy in a pre-clinical model of head and neck cancer," *J Control Release* 229:93-105, 2016.

Von Felbert et al., "A specific photoimmunotheranostics agent to detect and eliminate skin cancer cells expressing EGFR," *J Cancer Res Clin Oncol.* 142(5):1003-1011, 2016.

Vrouenraets et al., "Targeting of Aluminum (III) Phthalocyanine Tetrasulfonate by Use of Internalizing Monoclonal Antibodies: Improved Efficacy in Photodynamic Therapy," *Cancer Res.* 61:1970-1975, 2001.

Waite and Roth, "Nanoscale drug delivery systems for enhanced drug penetration into solid tumors: current progress and opportunities," *Crit Rev Biomed Eng.* 40:21-41, 2012.

Wang et al., "Theranostic Agents for Photodynamic Therapy of Prostate Cancer by Targeting Prostate-Specific Membrane Antigen," *Mol Cancer Ther.* 15(8):1834-1844, 2016.

Watanabe et al., "Photoimmunotherapy Targeting Prostate-Specific Membrane Antigen: Are Antibody Fragments as Effective as Antibodies?," *J Nucl Med.* 56:140-144, 2015.

Wessels et al., "Advances in cellular, subcellular, and nanoscale imaging in vitro and in vivo," *Cytometry A*: 77:667-676, 2010.

Xu et al., "Antibody Conjugated Magnetic Iron Oxide Nanoparticles for Cancer Cell Separation in Fresh Whole Blood," *Biomaterials* 32:9758-9765, 2011.

Yoon et al., "Advance in Photosensitizers and Light Delivery for Photodynamic Therapy," *Clin Endosc.* 46:7-23, 2013.

Zhang et al., "Target-selective phototherapy using a ligand-based photosensitizer for type 2 cannabinoid receptor," *Chem Biol.* 21:338-344, 2014 (with 7 pages of Supplementary Materials).

Zhang et al., "Tumor mitochondria-targeted photodynamic therapy with a translocator protein (TSPO)-specific photosensitizer," *Acta Biotreater.* 28:160-170, 2015 (with 6 pages of Supplementary Materials).

Zhu et al., "Visualization of P53264-272/HLA-A*0201 Complexes Naturally Presented on Tumor Cell Surface by a Multimeric Soluble Single-Chain T Cell Receptor," *J. Immunol.* 176:3223-3232, 2006.

Zinn et al., "IND-Directed Safety and Biodistribution Study of Intravenously Injected Cetuximab-IRDye800 in Cynomolgus Macaques." *Mol Imaging Biol.* 17:49-57, 2015.

Zuluaga et al., "Combination of Photodynamic Therapy With Anti-Cancer Agents," *Curr. Med. Chem.* 15:1655-1673, 2008.

CN 201280043973.2 First Office Action dated Nov. 24, 2014, with English translation (19 pages).

CN 201280043973.2 Second Office Action dated Aug. 12, 2015, with English translation (15 pages).

CN 201280043973.2 Office Action dated Feb. 22, 2016 for Application No. 201280043973.2 (with English translation).

CN 201280043973.2 Reexamination Notification dated Nov. 17, 2016, with English translation.

EP12738664.7 Examination Report dated Jul. 6, 2016.

JP 2014-520202 Office Action dated Feb. 3, 2016 (16 pages).

JP 2014-520202 Final Official Action dated Sep. 28, 2016, with English translation.

PCT/US2012/044421 International Search Report and Written Opinion dated Nov. 26, 2012 (18 pages).

PCT/US2015/044168 International Search Report dated Oct. 19, 2015 (4 pages).

PCT/US2015/044168 Written Opinion dated Oct. 19, 2015 (7 pages).

PCT/US2016/045090 International Search Report and Written Opinion dated Oct. 11, 2016 (12 pages).

PCT/US2019/026488 International Search Report and Written Opinion dated Jun. 26, 2019 (15 pages).

SG 2013091822 Search Report and Written Opinion dated Mar. 20, 2015 (9 pages).

Sg 2013091822 Written Opinion dated Nov. 11, 2015 (10 pages).

Dancey et al., "Phase I Trial of the 131I-Labelled Anti-CD25 Antibody Basiliximab in the Treatment of Patients with Relapsed or Refractor Lymphoma," *Blood* 110:648, 2007.

Kuhn et al., "The Role of Interleukin-2 Receptor Alpha in Cancer," *Frontiers in Bioscience* 10:1462-1474, 2005.

Sasikumar et al., "Small-Molecule Immune Checkpoint Inhibitors Targeting PD-1/PD-L1 and Other Emerging Checkpoint Pathways," *BioDrugs* 32:481-497, 2018.

BIO Clinica, vol. 19, p. 398-403, 2004. Concise English description attached to document.

Medical Sci Digest., 2004, vol. 30, p. 545-548. Concise English description attached to document.

New Pharmacology (New Yakurigaku), Nankodo Co., Ltd., 2012, the third impression of the revised sixth edition, p. 558-559 (4 pages). English translation attached to document.

Simpson et al., "Fc-dependent depletion of tumor-infiltrating regulatory T cells co-defines the efficacy of anti-CTLA-4 therapy against melanoma," *J Exp Med.* 210:1695-1710, 2013.

Agostinis et al., "Photodynamic Therapy of Cancer: An Update," *CA Cancer J Clin.* 61(4): 250-281, 2011.

Bartl et al., "Emissivity of aluminium and its importance for radiometric measurement," Measurement of Physical Quantities, 31-36, 2004.

BIO Clinica, vol. 19, p. 398-403, 2004 (in Japanese, with concise description in English).

(56) References Cited

OTHER PUBLICATIONS

Busch et al., "Increasing Damage to Tumor Blood Vessels during Motexafin Lutetium-PDT through Use of Low Fluence Rate," *Radiat Res.* 174(3):331-340, 2010.

Chauhan et al., "Angiotensin inhibition enhances drug delivery and potentiates chemotherapy by decompressing tumour blood vessels," *Nat Commun.* 4:2516, 2013 (11 pages).

Dolmans et al., "Targeting Tumor Vasculature and Cancer Cells in Orthotopic Breast Tumor by Fractionated Photosensitizer Dosing Photodynamic Therapy," *Cancer Res.* 62(15):4289-4294, 2002.

Houston et al., "Quality analysis of in vivo near-infrared fluorescence and conventional gamma images acquired using a dual-labeled tumor-targeting probe," *J Biomed. Optics* 10:054010-1 to 054010-11, 2005.

Kabolizadeh et al., "The role of cetuximab in the management of head and neck cancers," *Exp Opin Biol Ther.* 12(4):517-528, 2012.

Lee et al., "Peptides and Peptide Hormones for Molecular Imaging and Disease Diagnosis," *Chem Rev.* 110(5):3087-3111, 2010.

Li et al., "Structural basis for inhibition of the epidermal growth factor receptor by cetuximab," *Cancer Cell* 7(4):301-311, 2005.

Master et al., "A Cell-targeted Photodynamic Nanomedicine Strategy for Head & Neck Cancers," *Mol Pharm.* 10:1988-1997, 2013.

Medical Sci Digest., 2004, vol. 30, p. 545-548 (In Japanese, with concise description in English).

New Pharmacology (New Yakurigaku), Nankodo Co., Ltd., 2012, the third impression of the revised sixth edition, p. 558-559 (4 pages). (In Japanese, with translation).

Peng et al., "A nonfluorescent, broad-range quencher dye for Förster resonance energy transfer assays," *Anal Biochem.* 388(2):220-228, 2009.

Sekkat et al., "Like a bolt from the Blue: Phthalocyanines in Biomedical Optics," *Molecules* 17:98-144, 2012.

Sharman et al., "Targeted Photodynamic Therapy via Receptor-Mediated Delivery Sytems," *Adv Drug Deliv Rev.* 56(1):53-76, 2004.

Turner et al., "Administration of substances to laboratory animals: routes of administration and factors to consider," *J Am Assoc Lab Anim Sci.* 50(5):600-613, 2011.

Van Cutsem et al., "Cetuximab and chemotherapy as initial treatment for metastatic colorectal cancer," *N Engl J Med.* 360:1408-1417, 2009.

Van Cutsem et al., "Intrapatient cetuximab dose escalation in metastatic colorectal cancer according to the grade of early skin reactions: the randomized EVEREST study," *J Clin Oncol.* 30(23):2861-2868, 2012.

Wollina, "Cetuximab in non-melanoma skin cancer," *Exp Opin Biol Ther.* 12(7):949-956, 2012.

Safi et al., "Functional T cells targeting tumor-associated antigens are predictive for recurrence-free survival of patients with radically operated non-small cell lung cancer," *Oncoimmunol.* 6(11):E1360458, 2017 (12 pages).

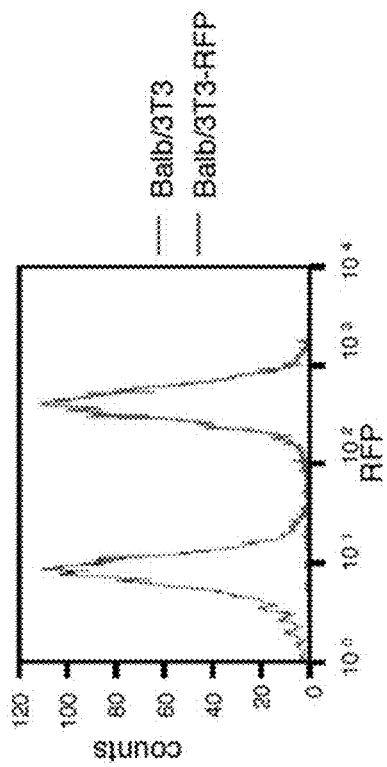
FIG. 10B
FIG. 10A
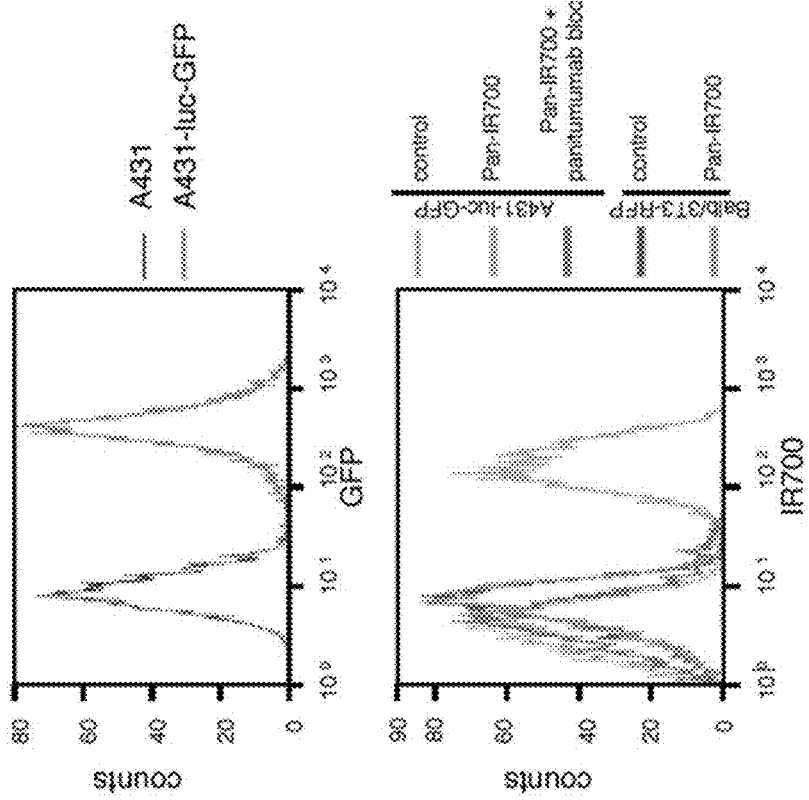
FIG. 10C

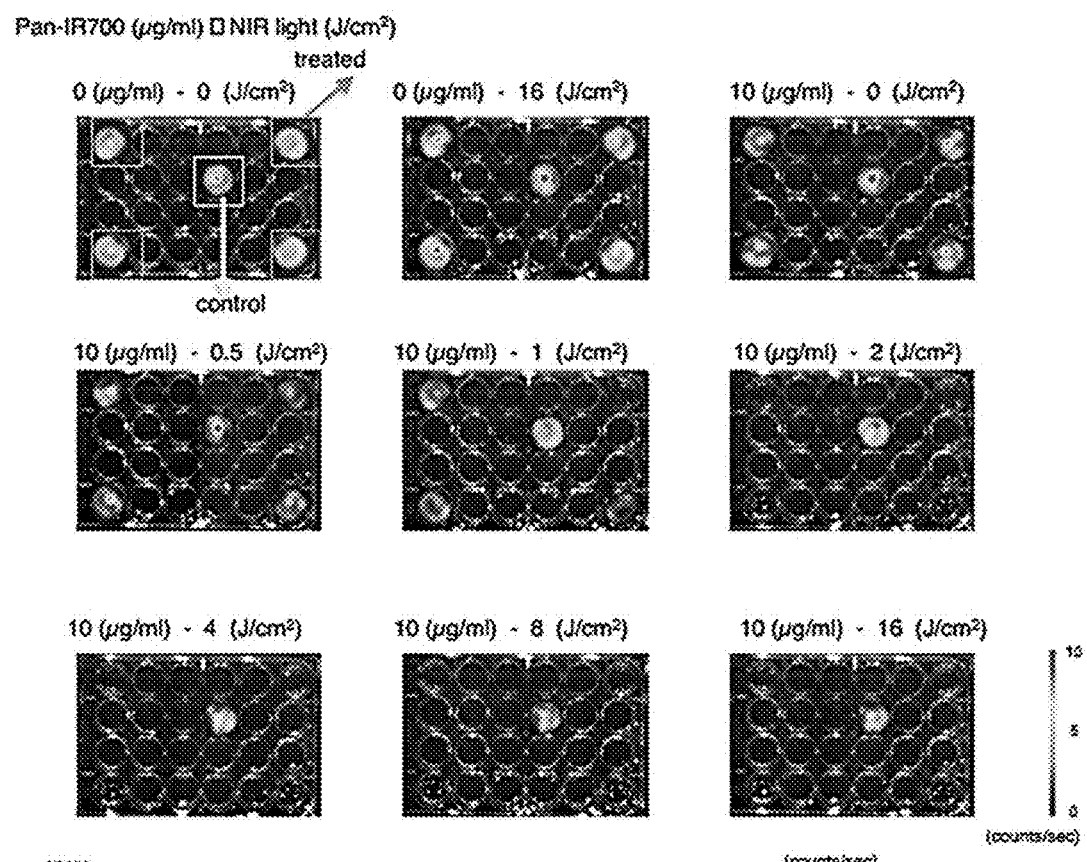
FIG. 12A
FIG. 12B
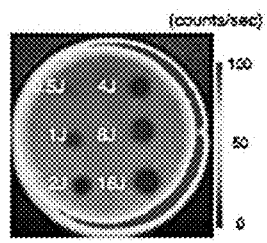
FIG. 12C

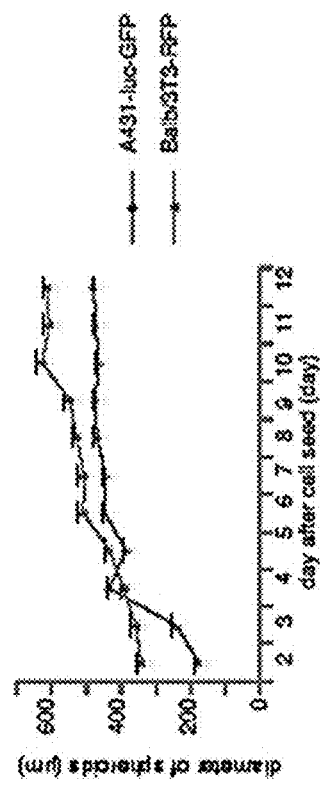
FIG. 15A
FIG. 15B
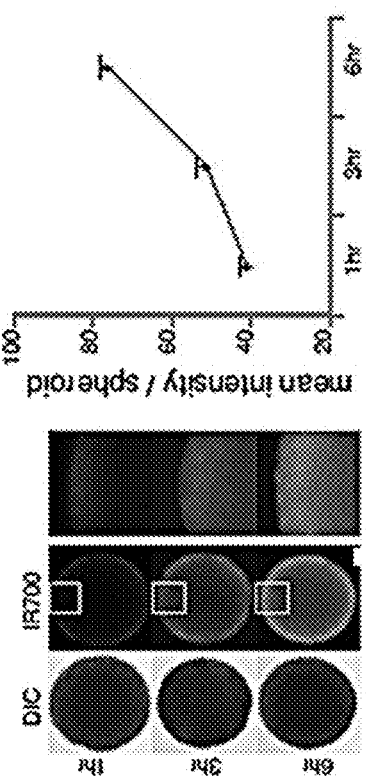
FIG. 15C
FIG. 15D
FIG. 15E
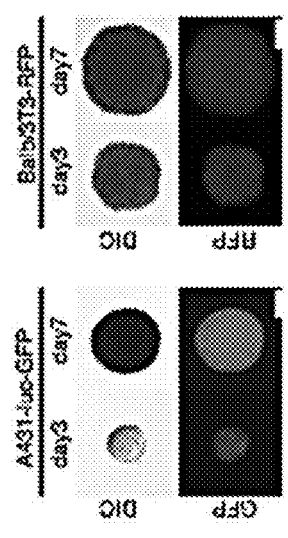
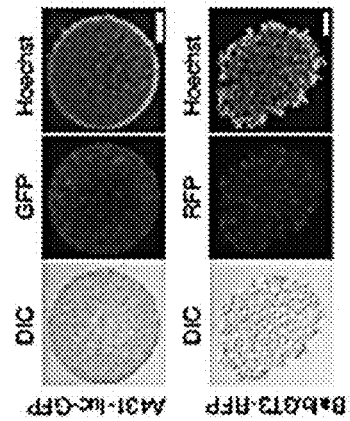
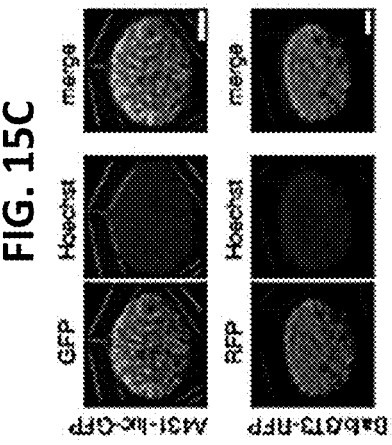

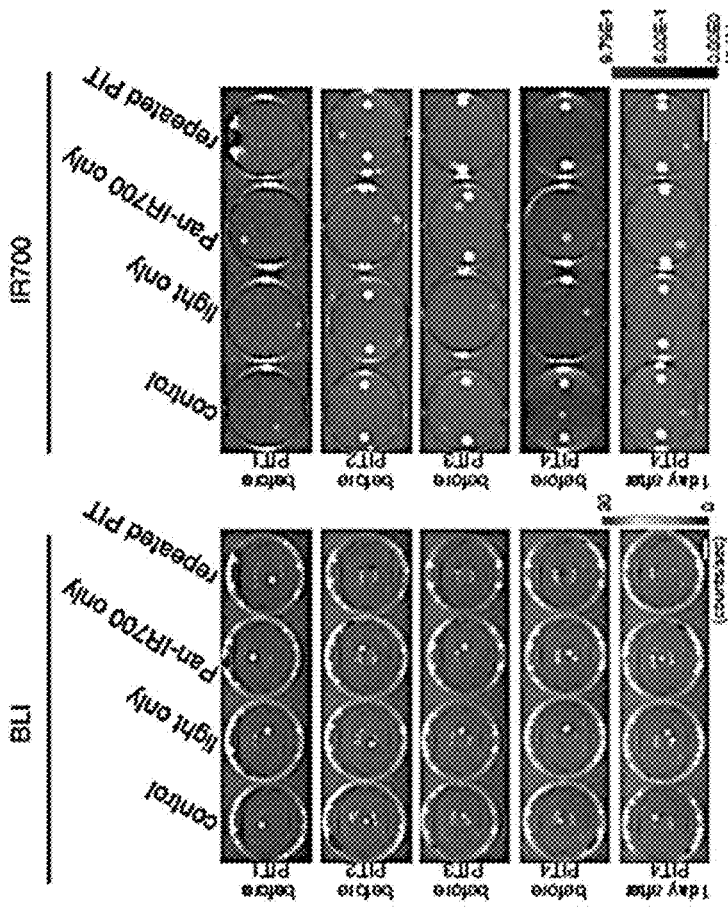
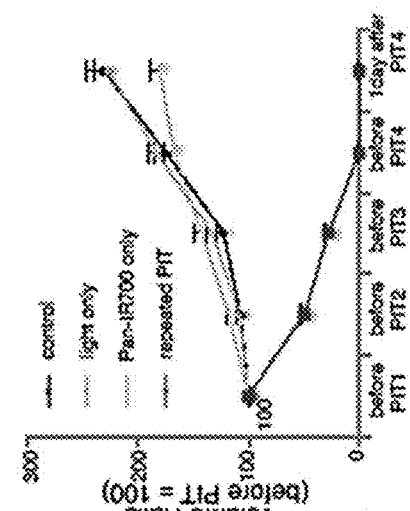
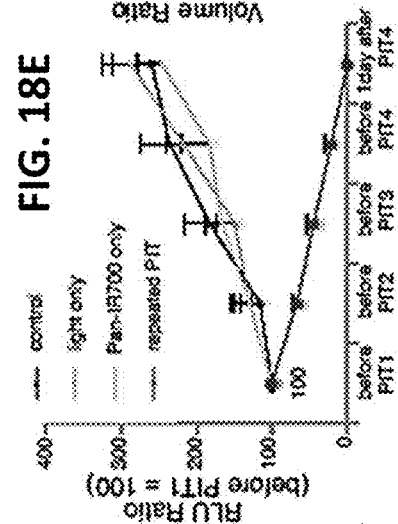
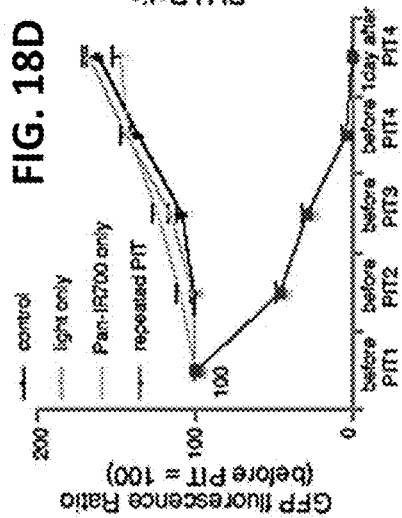
FIG. 18C
FIG. 18D
FIG. 18E
FIG. 18F

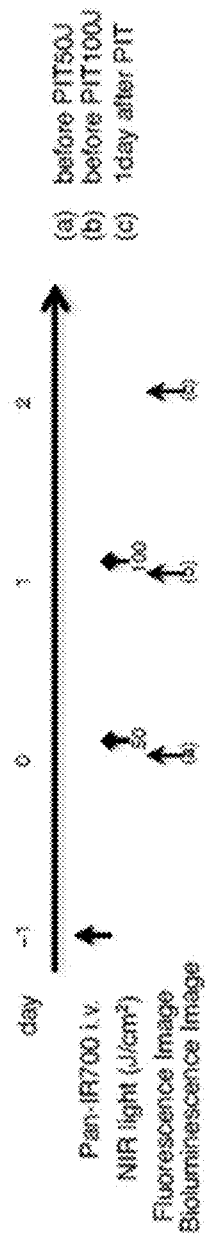
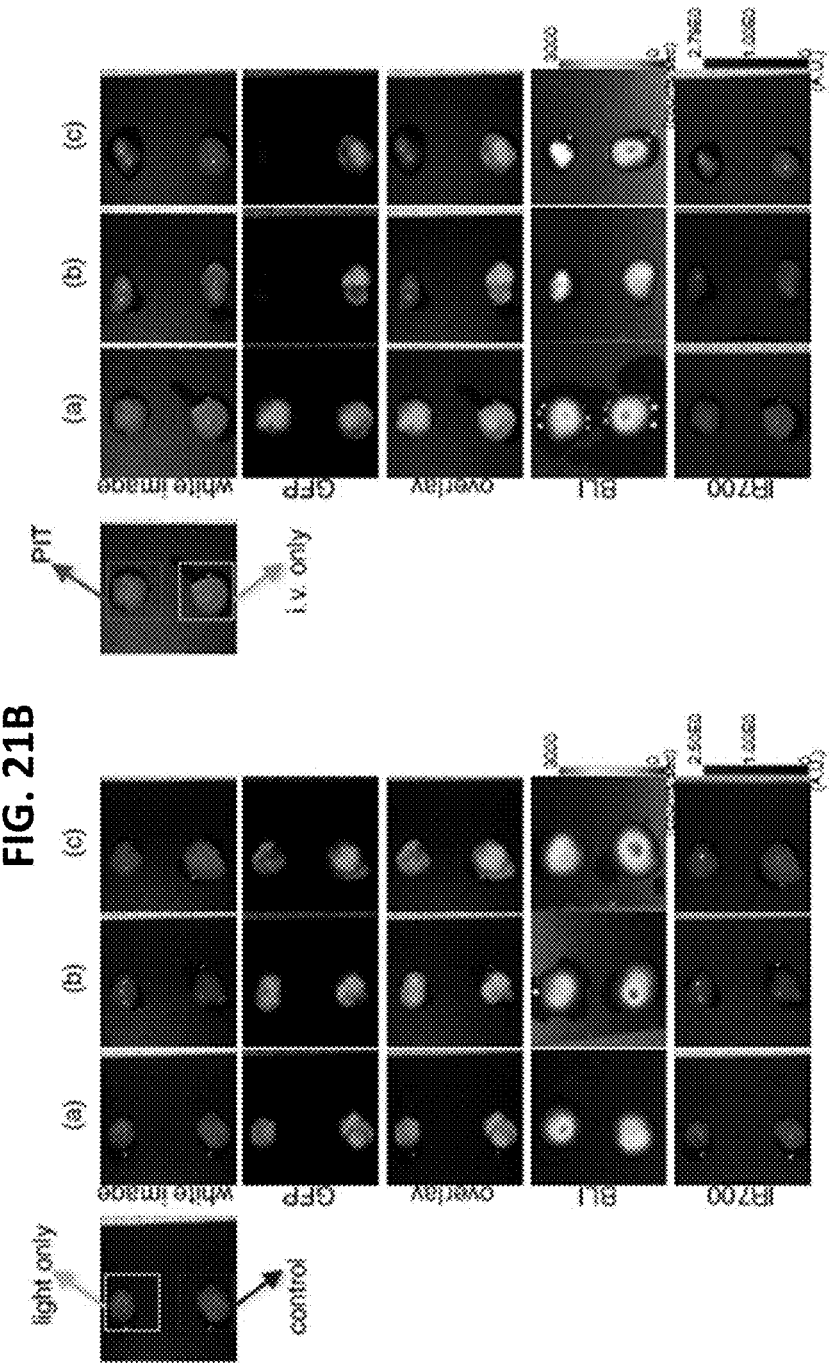
FIG. 21A
FIG. 21B

FIG. 24A
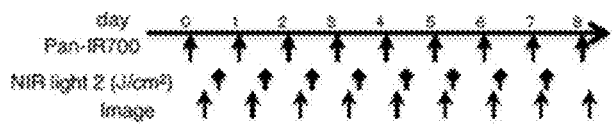
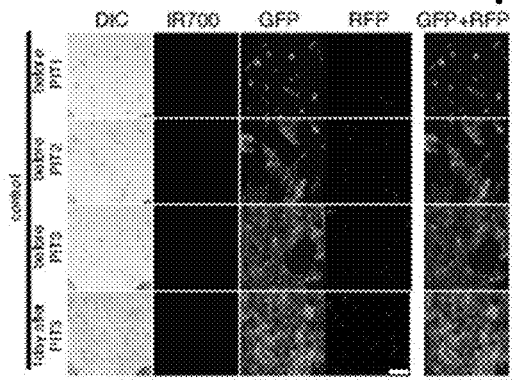
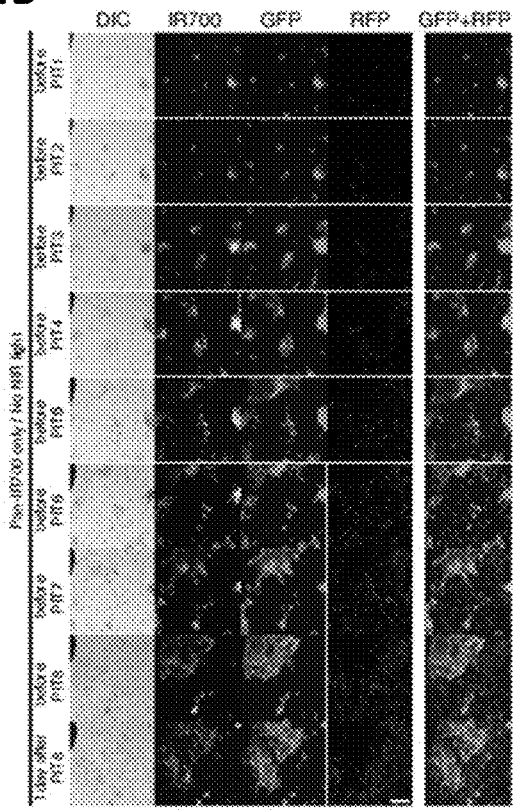
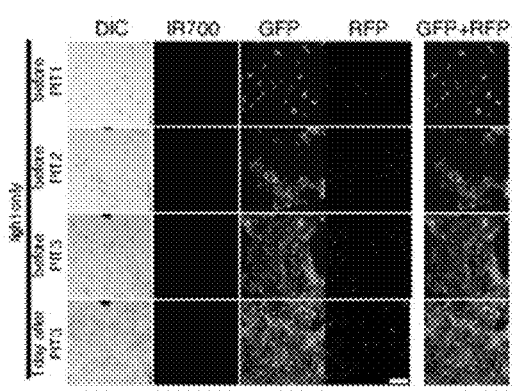
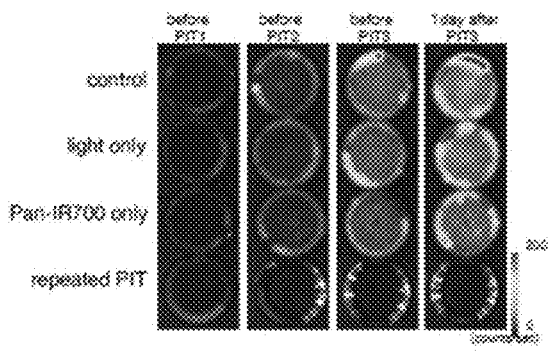
FIG. 24C

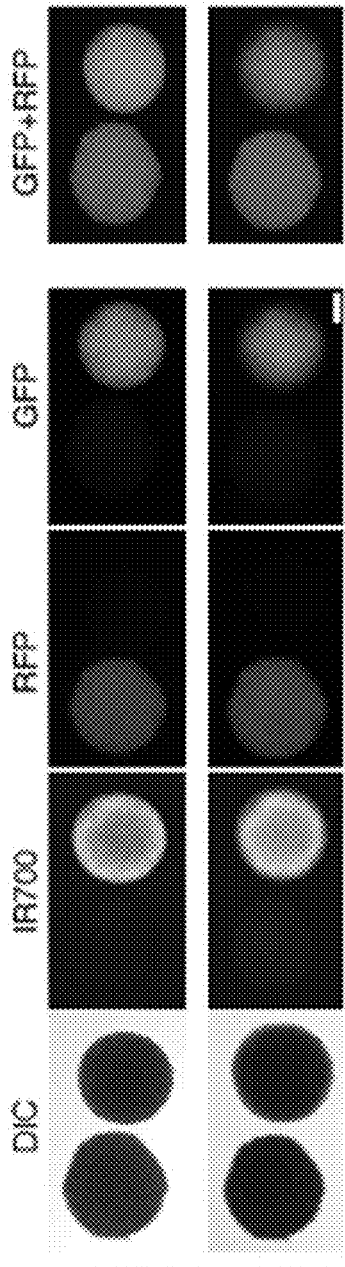
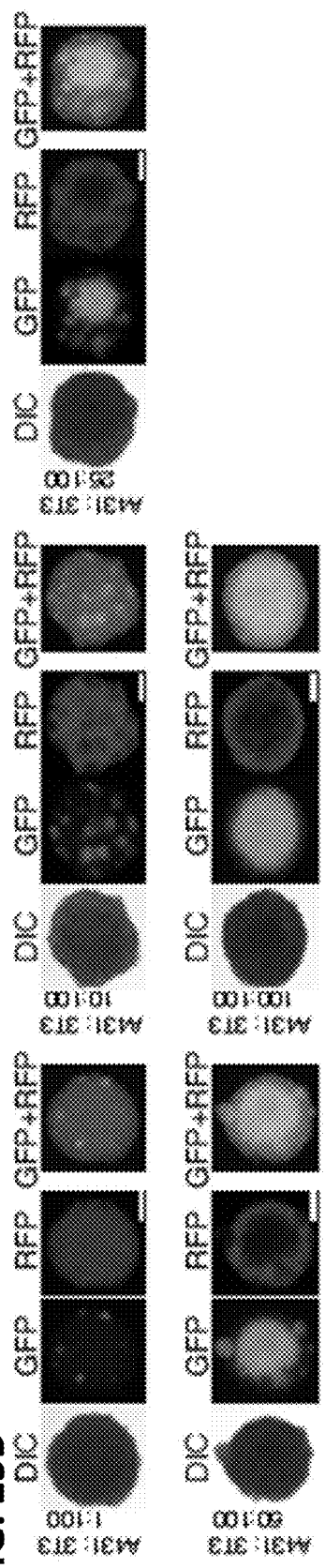
FIG. 25A
FIG. 25B

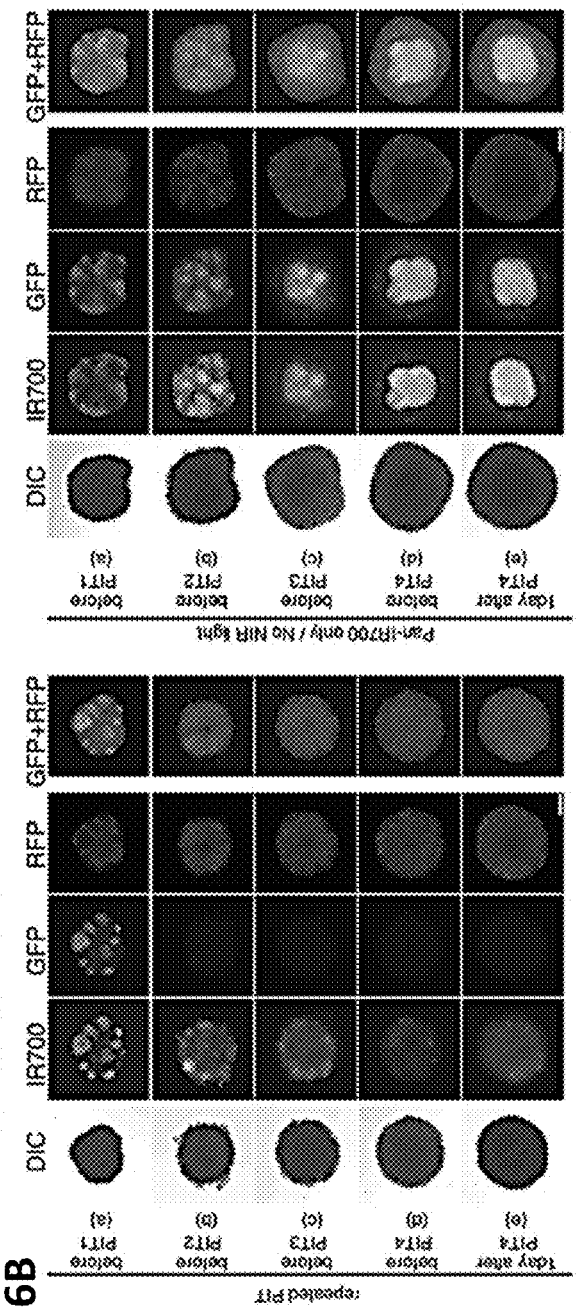
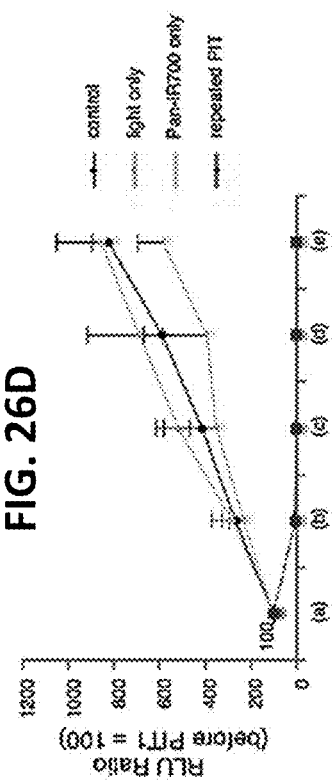
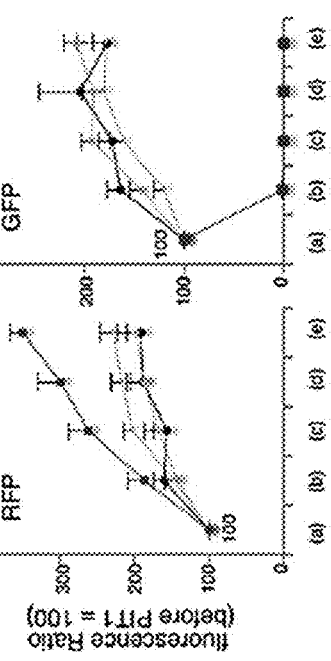
FIG. 26A
FIG. 26B
FIG. 26C
FIG. 26D

FIG. 27A
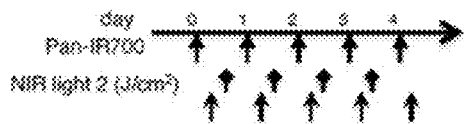
FIG. 27B
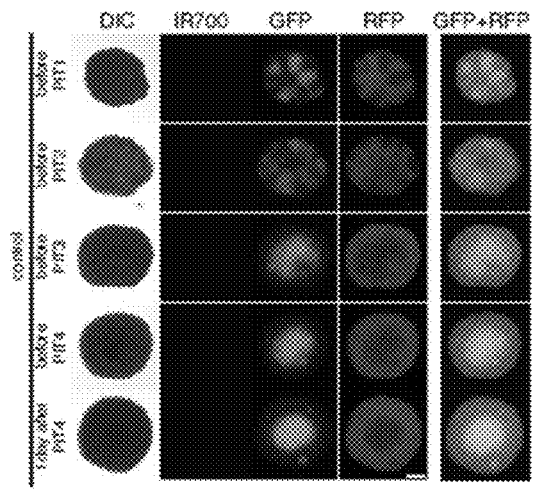
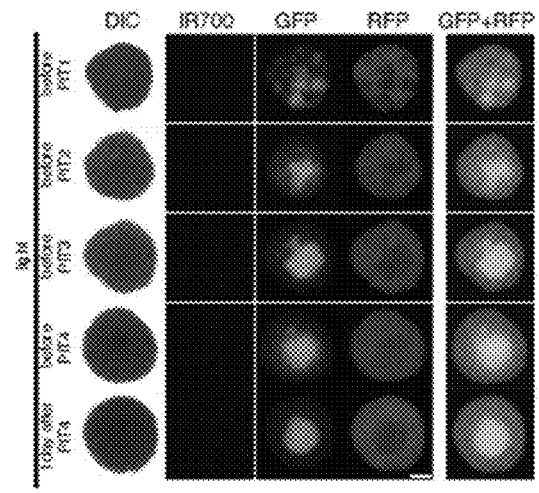
FIG. 27C

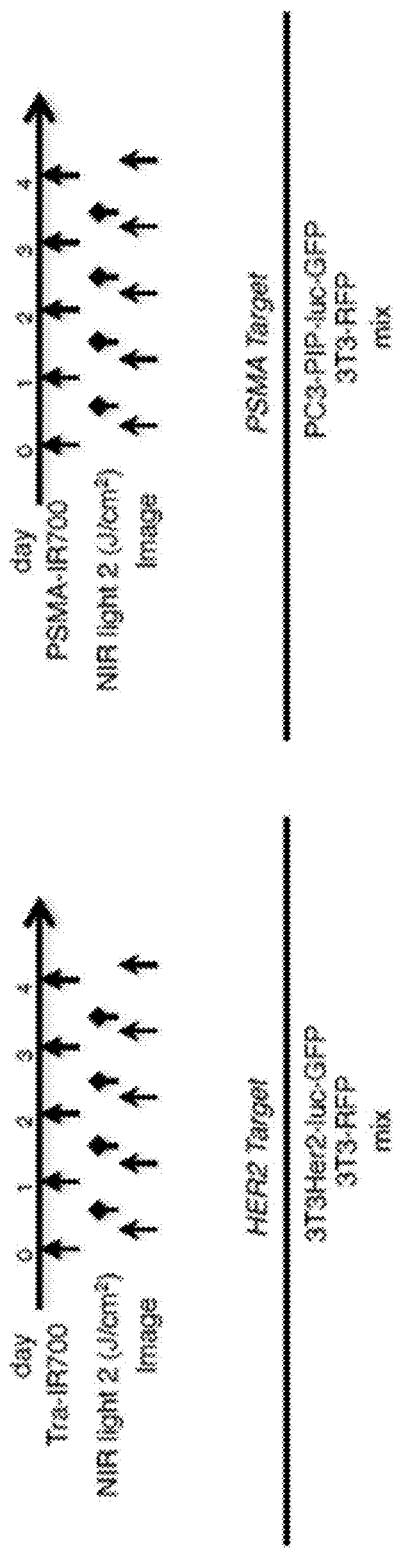

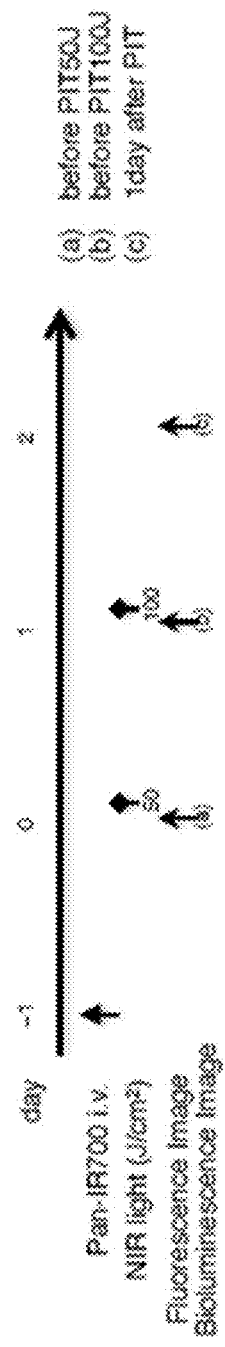
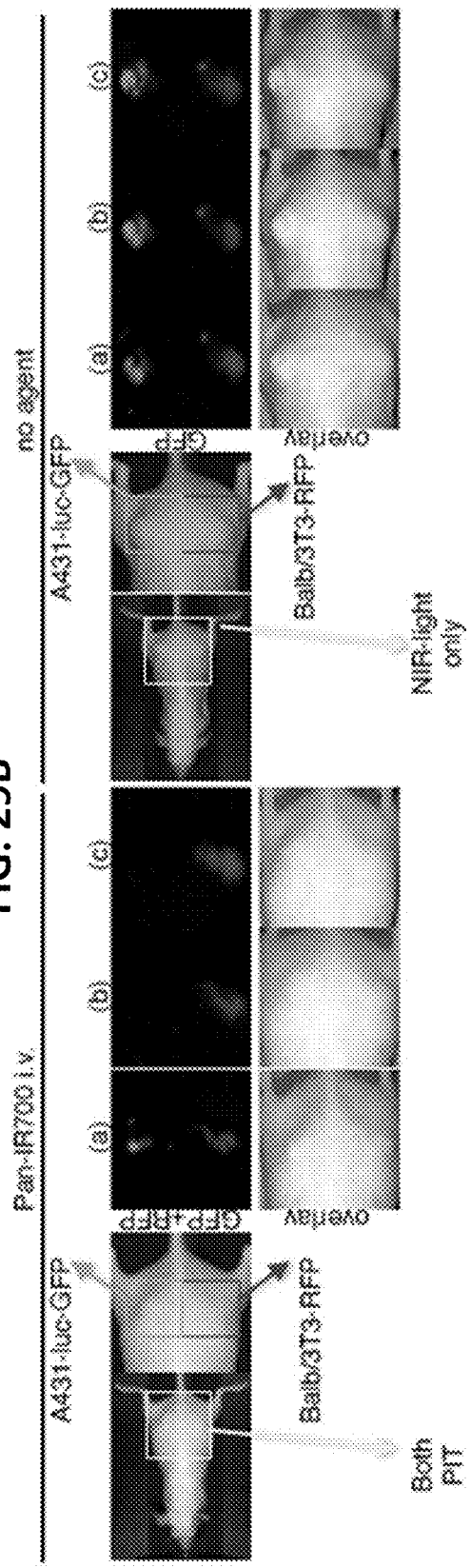
FIG. 29A
FIG. 29B

PHOTO-CONTROLLED REMOVAL OF TARGETS IN VITRO AND IN VIVO

CROSS-REFERENCE TO RELATED APPLICATIONS

This is a continuation of U.S. application Ser. No. 15/318,104 filed Dec. 12, 2016, now U.S. Pat. No. 10,830,678, which is the U.S. National Stage of International Application No. PCT/US2015/044168, filed Aug. 7, 2015, which was published in English under PCT Article 21(2), which in turn claims priority to U.S. Provisional Application No. 62/034,990 filed Aug. 8, 2014, herein incorporated by reference.

FIELD

This application relates to IR700 conjugates and methods of their use to remove (e.g., separate or isolate) a target agent in vivo or in vitro. For example, the disclosed IR700 conjugates and methods provide photo-controlled ways to control the pharmacokinetics of a drug in vivo, and can be used to remove undesired agents from environmental or food samples or to isolate target molecules in a laboratory.

BACKGROUND

Separation of biomolecules from complex mixtures is desirable in many applications, including removing toxins, pathogens, or drugs from a subject in vivo, or from other samples in vitro. In addition, many in vitro techniques, including diagnostic methods, environmental monitoring, or research techniques rely upon separation or isolation of molecules from complex mixtures. With current technologies, it is difficult to modify, isolate and/or eliminate a selected biomolecule among a mixture of biomolecules in environments such as solutions, cells, and whole organisms.

SUMMARY OF THE DISCLOSURE

With current technologies, it is difficult to isolate and eliminate a selected protein or other target molecule among a mixture of proteins in environments such as solutions, cells, and whole organisms. The methods disclosed here can remove or isolate an IR700-labeled molecule or a cluster of molecules associated with the IR700-labeled molecule (e.g. IR700-antibody-antigen complex). The phthalocyanine IRDye700DX (IR700), when conjugated to a specific binding agent (e.g., antibody, antibody fragment, hapten, protein, nucleic acid molecule, functional nucleic acid, and the like) is used to label target agents via binding between the specific binding agent and the target. Similarly, when IR700 is conjugated to a molecule, such as a pharmacological agent or drug, permits control of the removal of the agent, for example in a subject. Upon exposure to near infrared (NIR) light (e.g., 690 nm+/−20 nm), the IR700 dye is cleaved, changing the molecule from hydrophilic to hydrophobic, and resulting in aggregation of the molecule. This enables the removal of the target from a solution, cell or an organism. Furthermore, this change can affect the target attached to the IR700-specific binding agent complex, wherein the target (e.g., protein) can lose its function and form aggregates in solution, damage a cell membrane and induce cytotoxicity in cells to which the target is bound or results in removal of such cells, for example by macrophages in the liver.

Provided herein are in vitro, ex vivo, and in vivo methods for removing, such as isolating or separating, one or more target molecules or agents from a sample or a subject. For example, the method can allow for removal or separation of proteins, peptides, lectins, carbohydrates, metals (such as heavy metals), nucleic acid molecules, small organic molecules, drugs, pathogens (e.g., virus, bacterium, parasite, or fungus), and cells. In some examples, the method also includes detecting the removed target. For example, the methods can be used to remove unwanted agents (such as impurities, metals, pathogenic organisms, spores, and the like) from a manufacturing process (such as a drug manufacturing process), for example to improve a purification process. Similarly, the methods can be used to remove pathogens, toxins, spores, or metals from an environmental source or sample, or from a food sample or item. In addition, the disclosed methods can be used to control the pharmacokinetics of a drug in vivo, such as controlled drug delivery, for example by removing a drug from a patient in vivo. In another example, the methods can be used to remove unwanted agents in vivo, for example by removing a potentially dangerous or poisonous material (e.g., a pathogen, toxins, metal, recreational drug, virus, venom, and the like), or by removing specific cells or cell populations from a tumor to modulate the immune response (e.g., killing specific tumor cells or immune cells in a tumor, such as cancer stem cells). In some examples, such methods are used in combination with apheresis, for example to remove a target (e.g., target cell) from the blood, or in combination with a method that uses an organ that is vascularly isolated for perfusion. In addition, the methods can be used ex vivo, for example to isolate or remove targets (e.g., cells) from a sample, such as a blood sample, bone marrow sample, or tissue culture.

Provided herein are methods for removing (e.g., isolating or separating) a target from a sample. Such methods can include contacting the sample with an IR700-molecule conjugate, wherein the molecule conjugated to the IR700 is a specific binding agent (e.g., antibody, antibody fragment, hapten, protein, nucleic acid molecule, functional nucleic acid, and the like) that preferentially binds to the target. The sample is incubated with the IR700-molecule conjugate under conditions that permit the target to bind to the molecule of the IR700-molecule conjugate, resulting in an IR700-molecule conjugate-target complex. The sample is irradiated with NIR light, for example at a wavelength of 660 to 710 nm at a dose of at least 1 J cm$^{-2}$ under conditions sufficient for generating a hydrophobic IR700-molecule conjugate-target complex. For example, irradiation of the IR700-molecule conjugate-target complex cleaves or removes a portion of the IR700, changing the IR700-molecule conjugate-target complex from a hydrophilic to a hydrophobic IR700-molecule conjugate-target complex.

The sample is then incubated under conditions that permit the hydrophobic IR700-molecule conjugate-target complex to aggregate. For example, the sample can be reacted or mixed under conditions that allow the aggregate or precipitate to form, which in some examples collects or deposits at the bottom of a container. In some examples, the sample is centrifuged to collect the resulting aggregate. The hydrophobic IR700-molecule conjugate-target complex is then removed or separated from the sample, thereby removing, isolating or separating the target from the sample. In some examples, the method also includes detecting or measuring the target removed from the sample. In some examples, the method also includes detecting other molecules (such as other proteins, nucleic acids, lectins, carbohydrates, etc.) bound to the target. In some examples, the method includes removing unwanted cells from a cell culture (2D or 3D), as for example in tissue regeneration.

Also provided are in vivo methods that can be used to remove a target molecule from a subject, such as a mammal. In some examples, the methods include administering to a subject a therapeutically effective amount of an IR700-molecule conjugate, wherein the molecule conjugated to the IR700 includes the target molecule (e.g., a pharmacological agent) or wherein the IR700-molecule conjugate specifically binds to the target molecule (e.g., includes IR700 conjugated to a specific binding agent). The subject is irradiated with NIR light under conditions sufficient for cleaving or removing a portion of the IR700, changing the IR700-molecule conjugate or IR700-molecule conjugate-target complex from hydrophilic to hydrophobic. Examples of such conditions include irradiation at a wavelength of 660 to 710 nm, for example at a dose of at least 10 J cm$^{-2}$. For example, the irradiating can be performed by a device worn by the subject, wherein the device includes a NIR light emitting diode (LED). Such devices can include an article of clothing, jewelry, or a covering, which may further include power and/or cooling sources. The hydrophobic IR700-molecule conjugate or IR700-molecule conjugate-target complex is allowed to aggregate and removed from the subject (for example via the liver and/or spleen), thereby removing the target molecule from the subject. The method can also include detecting a decrease in the amount of the target molecule in the subject (for example by performing a blood test that permits detection of the target, such as an immunoassay, nucleic acid hybridization, sequencing, or PCR assay). The method can also be used to remove specific cells, for example, regulatory immune cells from a tumor, thus enhancing natural host immune response to a tumor.

The foregoing and other features of the disclosure will become more apparent from the following detailed description of a several embodiments which proceeds with reference to the accompanying figures.

BRIEF DESCRIPTION OF THE FIGURES

FIGS. 10A-10C show the characterization of A431 cell line. (A) A431 cells were stably transfected with luciferase and GFP (both on the same plasmid) as confirmed by FACS. (B) Balb/3T3 cells were stably transfected with RFP as confirmed by FACS. (C) A431-luc-GFP cells demonstrate EGFR expression. Specific binding was demonstrated with a blocking study. Non-EGFR expressing Balb/3T3-RFP were also incubated with Pan-IR700, but no binding was observed.

FIGS. 12A-12C show the quantification of PIT effect on 2D culture of A431-luc-GFP cells by luciferase activity. (A, B) Bioluminescence in A431-luc-GFP cells was measured as relative light unit (RLU), and was decreased in a NIR-light dose-dependent manner (1 hr after PIT). (C) Bioluminescence imaging (BLI) of a 10 cm dish demonstrated that luciferase activity in A431-luc-GFP cells decreased in a NIR-light dose-dependent manner.

FIGS. 15A-15E show the characterization of in vitro 3D spheroids. (A) Representative image of A431-luc-GFP/Balb/3T3-RFP 3D spheroids. Bar=200 μm. (B) 3D spheroids grew to around 500 μm (n=10). (C) 3D reconstruction image of a 3D spheroid at day 7. Bar=100 μm. (D) Frozen section of 3D spheroid. Cells accumulate within the core of the spheroid. Bar=100 μm. (E) Pan-IR700 permeates centrally in a time-dependent manner (mean intensity of IR700 fluorescence in a spheroid) (n=10).

FIGS. 18A-18F show the effects of repeated PIT on 3D spheroids. (A) The PIT regimen incorporating repeated NIR light exposures is shown. (B) Day 7 A431-luc-GFP 3D spheroids were divided into 4 groups as shown. Bar=100 μm. (C) Bioluminescence imaging (BLI) of each group demonstrated that luciferase activity decreased after repeated PIT. Bar=5 mm. Macroscopic view of IR700 fluorescence was also demonstrated (by Pearl Imager). (D) Quantification of GFP-fluorescence intensity showed progressive decreases after repeated PIT eventually resulting in no detectable fluorescence (total pixels of GFP fluorescence in the same spheroid) (n=10 spheroids in each group). (E) Bioluminescence was measured as relative light units (RLU), which decreased progressively after repeated PIT eventually resulting in near 0 RLU (under the background level)(n=10). (F) The volume of A431-luc-GFP 3D spheroids also decreased after repeated PIT (n=10).

FIGS. 21A-21B show the PIT effect on ex vivo A431-luc-GFP flank tumor. (A) The PIT regimen incorporating repeated NIR light exposures is shown. (B) ex vivo GFP/IR700 fluorescence imaging and BLI of a flank tumor in response to PIT confirmed disappearance of both GFP fluorescence and bioluminescence.

FIGS. 24A-24C show target cell killing in 2D cell culture. (A) The PIT regimen incorporating repeated NIR light exposures is shown. (B) Repeated PIT completely eliminated target cells with no damage to non-target cells, until non-target cells became confluent. 100:10 ratio of A431-luc-GFP and Balb/3T3-RFP mixed cells were cultured Control group is demonstrated and the black line at edge is a marker to maintain consistent positioning. Bar=200 μm. (C) BLI of a 35 mm dish demonstrated that luciferase activity in A431-luc-GFP cells progressively decreased after repeated PIT eventually completely disappearing.

FIGS. 25A-25B show the characterization of mixed 3D spheroid. (A) The effect of PIT on a spheroid containing A431-luc-GFP cells while no damage is done to the spheroid containing Balb/3T3-RFP cells. Bar=200 μm. (B) Characterization of various ratios of mixed spheroid at day 7. Bar=200 μm.

FIGS. 26A-26D show target cell elimination in 3D cell spheroids. (A) PIT (2 J/cm2) regimen is shown. (B) Repeated PIT completely eliminated target cells with no harm to non-target cells, in a mixed 3D spheroid. Bar=200 µm. (C) Quantification of fluorescence ratios showed complete elimination of target cells and no effect on non-target cells. (n=10 spheroids in each group). (D) Quantification of luciferase activities (RLU ratio) demonstrated complete elimination of target cells (n=10 spheroids in each group).

FIGS. 27A-27C show target cell elimination in 3D mixed cell spheroid. (A) Treatment regimen is shown. (B) Repeated PIT completely eliminated target cells while not damaging non-target cells, in a mixed 3D cell culture. Control group (control and light only) microscopy is shown. Bar=200 µm. (C) BLI of a spheroid in a glass-bottom dish demonstrated reductions in luciferase activity in mixed 3D spheroids after PIT eventually leading to complete disappearance. Bar=5 mm. Macroscopic view of IR700 fluorescence was also demonstrated (Pearl Imager).

FIGS. 28A-28B show target cell (HER2 target and PSMA expressing cells) elimination in 3D spheroids. (A) Regimen of repeat PIT (2 J/cm2) is shown above the image. Repeated PIT completely eliminated HER2 expressing cells while not harming non-target cells. Bar=200 µm. (B) Regimen of repeat PIT (2 J/cm2) shown above the image. Repeat PIT completely eliminated PSMA targeted cells while not harming non-target cells. Bar=200 µm.

FIGS. 29A-29B show the characterization of in vivo tumor. (A) Regimen of repeat PIT is shown. (B) PIT had a response in the target tumor but no effect on the non-target tumor.

DETAILED DESCRIPTION OF SEVERAL EMBODIMENTS

Figure 1:
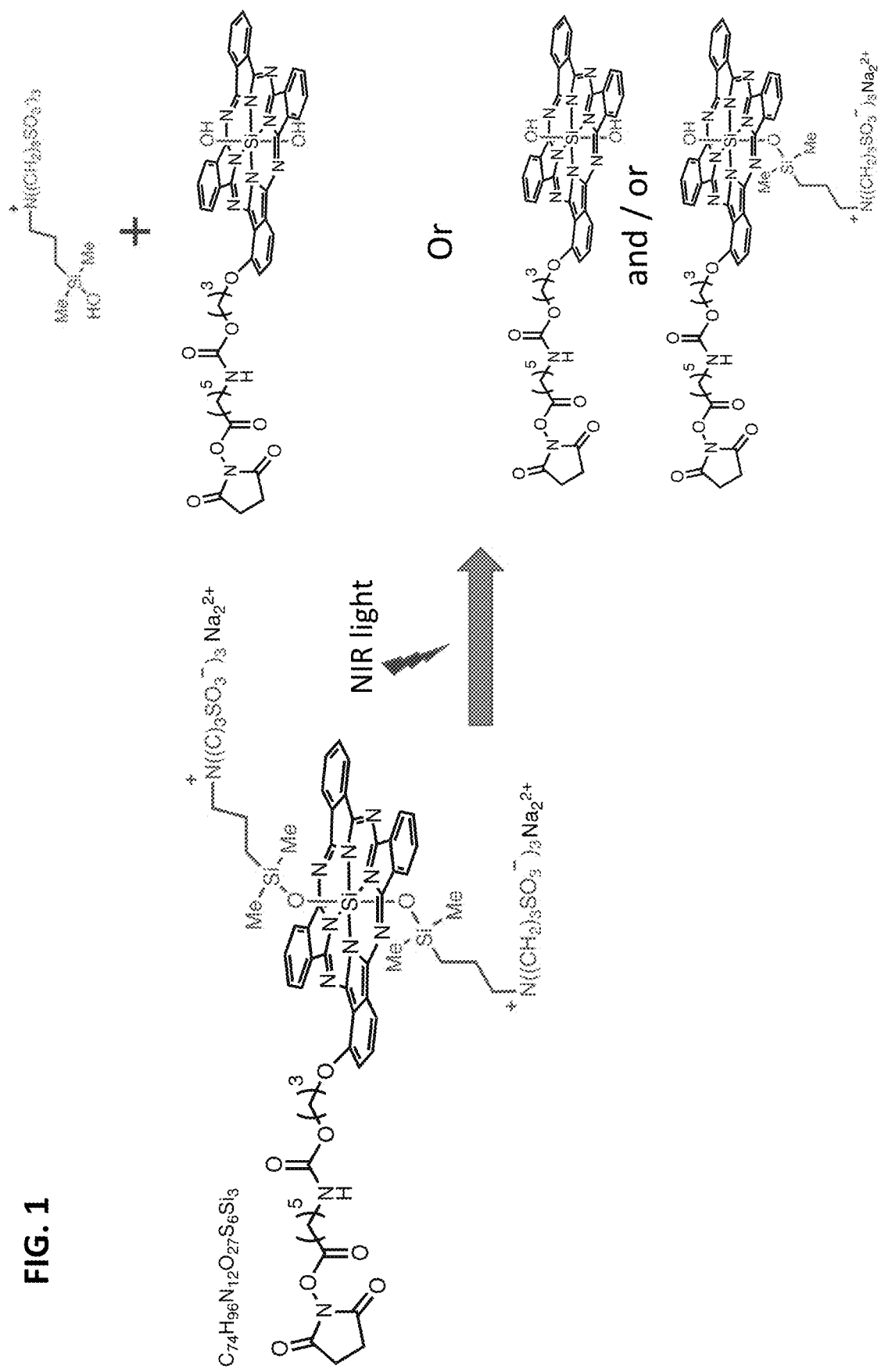
FIG. 1 is a schematic drawing showing the result of exposing IR700 to NIR light. Following this exposure, a portion of IR700 is cleaved. The remaining compound (the larger portion) is "superhydrophobic", which leads to its aggregation.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All references, including patents and patent applications, are herein incorporated by reference. In addition, the sequences associated with all GenBank® Accession numbers referenced herein are incorporated by reference for the sequence available on Aug. 8, 2014.

In order to facilitate review of the various embodiments of the disclosure, the following explanations of specific terms are provided:

Administration: To provide or give a subject an agent, such as an IR700-molecule conjugate, by any effective route. Exemplary routes of administration include, but are not limited to, topical, injection (such as subcutaneous, intramuscular, intradermal, intraperitoneal, intratumoral, intra-arterial, and intravenous), oral, ocular, sublingual, rectal, transdermal, intranasal, vaginal and inhalation routes. In some example, administration is achieved during a perfusion, such as an organ perfusion.

Antibody (Ab): Includes intact immunoglobulins (such as monoclonal antibodies, polyclonal antibodies), variants (such as chimeric antibodies), and portions of antibodies, such as an antigen binding fragment of a naturally occurring or recombinant antibody. Generally, an Ab is a polypeptide ligand comprising at least a light chain or heavy chain immunoglobulin variable region which specifically recognizes and binds an epitope of an antigen, such as a target protein. Each heavy chain and a light chain has a variable region, termed the variable heavy ($V_H$) region and the variable light ($V_L$) region. Together, the $V_H$ region and the $V_L$ region are responsible for binding the antigen recognized by the antibody. Antibodies can be conjugated to IR700 molecules using routine methods and used in the methods provided herein, for example to remove, isolate, or separate a target molecule in vitro or in vivo.

Antigen (Ag): A compound, composition, or substance that can stimulate the production of antibodies or a T cell response in an animal, including compositions (such as one that includes a tumor-specific protein) that are injected or absorbed into an animal. Examples of antigens include, but are not limited to, peptides, lipids, polysaccharides, and nucleic acids containing antigenic determinants, such as those recognized by an immune cell. In some examples, an antigen includes a tumor-specific peptide (such as one found on the surface of a cancer cell) or immunogenic fragment thereof.

An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

The binding of an antibody to a target antigen or epitope thereof can be used to remove the target using the methods provided herein.

Aptamer: Single stranded (ss) nucleic acid molecules (such as DNA or RNA) that bind a specific target agent (such as a protein or small organic molecule) with high affinity and specificity (e.g., as high as $10^{-14}$ M), and upon binding to the target, the ss nucleic acid molecule undergoes a conformational change and forms a tertiary structure. They are typically around 15 to 60 nucleotides (nt) in length, but some are longer (e.g., over 200 nt). Thus, in some examples, aptamers are at least 15 nt, at least 20 nt, at least 25 nt, at least 30 nt, at least 50 nt, at least 60 nt, at least 75 nt, at least 100 nt, at least 150 nt, at least 200 nt, such as 15 to 250 nt, 15 to 200 nt, or 20 to 50 nt. Aptamers can be conjugated to IR700 molecules using routine methods and used in the methods provided herein, for example to remove, isolate, or separate a target molecule in vitro or in vivo.

Aptamers are known and have been obtained through a combinatorial selection process called systematic evolution of ligands by exponential enrichment (SELEX) (see for example Ellington et al., Nature 1990, 346, 818-822; Tuerk and Gold Science 1990, 249, 505-510; Liu et al., Chem. Rev. 2009, 109, 1948-1998; Shamah et al., Acc. Chem. Res. 2008, 41, 130-138; Famulok, et al., Chem. Rev. 2007, 107, 3715-3743; Manimala et al., Recent Dev. Nucleic Acids Res. 2004, 1, 207-231; Famulok et al., Acc. Chem. Res. 2000, 33, 591-599; Hesselberth, et al., Rev. Mol. Biotech. 2000, 74, 15-25; Wilson et al., Annu. Rev. Biochem. 1999, 68, 611-647; Morris et al., Proc. Natl. Acad. Sci. U.S.A. 1998, 95, 2902-2907). In such a process, DNA or RNA molecules that are capable of binding a target molecule of interest are selected from a nucleic acid library consisting of $10^{14}$-$10^{15}$ different sequences through iterative steps of selection, amplification and mutation. Aptamers that are specific to a wide range of targets from small organic molecules such as adenosine, to proteins such as thrombin, and even viruses and cells have been identified (Liu et al., Chem. Rev. 2009, 109:1948-98; Lee et al., Nucleic Acids Res. 2004, 32, D95-D100; Navani and Li, Curr. Opin. Chem. Biol. 2006, 10, 272-281; Song et al., TrAC, Trends Anal. Chem. 2008, 27:108-17). The affinity of the aptamers towards their targets can rival that of antibodies, with dissociation constants as low as the picomolar range (Morris et al., Proc. Natl. Acad. Sci. U.S.A. 1998, 95:2902-7; Green et al., Biochemistry 1996, 35:14413-24).

Autoimmune disease: A disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosus, autoimmune thrombocytopenia purpura, Goodpasture's syndrome, Addison's disease, systemic sclerosis, polymyositis, dermatomyositis, autoimmune hemolytic anemia, pernicious anemia, and the like.

Binding: An association between two substances or molecules, such as the hybridization of one nucleic acid molecule to another (or itself), the association of an antibody, Affibody® molecule, hapten, or functional nucleic acid with a protein or small organic molecule, the association of a protein with another protein or nucleic acid molecule, the association of a lectin with a carbohydrate, or the association between a hapten and an antibody. Binding can be detected by any procedure known to one skilled in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorptionlionization time-of-flight mass spectrometry, microcytometry, microarray, microscopy, fluorescence activated cell sorting (FACS), and flow cytometry.

One molecule is said to "specifically bind" to another molecule when a particular agent (a "specific binding agent") can specifically react with a particular target, but not to unrelated molecules, for example to specifically immunoreact with a target, to specifically hybridize to a target, or to specifically bind to a target. For example, a lead-specific binding agent binds substantially only to lead in vitro or in vivo and a CD45-specific binding agent binds substantially only the CD45 protein in vitro or in vivo. The binding is a non-random binding reaction, for example between a specific binding agent (such as an antibody or functional fragment thereof, Affibody® molecule, hapten, lectin, protein, nucleic acid molecule or functional nucleic acid molecule) and a target (such as a cell, protein, carbohydrate, pathogen, small organic molecule, metal, DNA or RNA). Binding specificity can be determined from the reference point of the ability of the specific binding agent to differentially bind the target and an unrelated molecule, and therefore distinguish between two different molecules. For example, an oligonucleotide molecule binds or stably binds to a target nucleic acid molecule if a sufficient amount of the oligonucleotide molecule forms base pairs or is hybridized to its target nucleic acid molecule, to permit detection of that binding.

In some examples, a molecule (such as the molecule of an IR700-molecule conjugate) specifically binds to a target (such as a protein) with a binding constant that is at least $10^3$ $M^{-1}$ greater, $10^4$ $M^{-1}$ greater or $10^5$ $M^{-1}$ greater than a binding constant for other molecules in a sample or subject. In particular examples, two compounds are said to specifically bind when the binding constant for complex formation between the components is at least $10^4$ L/mol, for example, at least $10^6$ L/mol, at least $10^8$ L/mol, or at least $10^{10}$ L/mol. The binding constant for two components can be determined using methods that are well known in the art.

In particular examples, two compounds are said to specifically bind when the binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about 1.0×10$^{-8}$ M, at least about 1.3×10$^{-8}$ M at least about 1.5× 10$^{-8}$ M, at least about 2.0×10$^{-8}$ M, at least about 2.5×10$^{-8}$, at least about 3.0×10$^{-8}$, at least about 3.5×10$^{-8}$, at least about 4.0×10$^{-8}$, at least about 4.5×10$^{-8}$, or at least about 5.0×10$^{-8}$ M.

In certain embodiments, a specific binding agent that binds to target has a dissociation constant (Kd) of ≤104 nM, ≤100 nM, ≤10 nM, ≤1 nM, ≤0.1 nM, ≤0.01 nM, or ≤0.001 nM (e.g., 10$^{-8}$M or less, e.g., from 10$^{-8}$M to 10$^{-13}$M, e.g., from 10$^{-9}$ M to 10$^{-3}$ M). In one embodiment, Kd is measured by a radiolabeled antigen binding assay (RIA) performed with the Fab version of an antibody of interest and its antigen (see, e.g., Chen et al., *J. Mol. Biol.* 293:865-881, 1999). In another example, Kd is measured using surface plasmon resonance assays using a BIACORES-2000 or a BIACORES-3000 (BIAcore, Inc., Piscataway, N.J.) at 25° C. with immobilized antigen CM5 chips at about 10 response units (RU).

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system. In one example, a cell targeted for removal by the disclosed methods is a cancer cell.

Contact: Placement in direct physical association, including a solid or a liquid form. Contacting can occur in vitro or ex vivo, for example, by adding a reagent to a sample, or in vivo by administering to a subject.

Decrease: To reduce the quality, amount, or strength of something. In one example, the methods herein decrease an amount of target in a sample, source, or in a subject. For example, use of an IR700-molecule complex decreases an amount of a target, which can be the agent to which the IR700-molecule specifically binds, or can be the molecule of the IR700-molecule complex. In some examples, the decrease or reduction of the target is at least 20%, at least 50%, at least 75%, at least 90%, at least 95%, at least 98%, or at least 99%, relative to the amount of target observed if no IR700-molecule is added and no NIR light is applied. In other examples, decreases are expressed as a fold change, such as a decrease in the target of at least 2-fold, at least 3-fold, at least 4-fold, at least 5-fold, at least 8-fold, at least 10-fold, or even at least 15 or 20-fold, relative to the amount of target observed if no IR700-molecule is added and no NIR light is applied. Such decreases can be measured using routine methods in the art as well as the methods disclosed herein.

Detect: To determine if a particular agent (e.g., target) is present or absent, and in some example further includes semi-quantification or quantification of the agent if detected.

Deoxyribozyme (DNAzyme): Functional DNA molecules that display catalytic activity toward a specific target. Also referred to as catalytic DNAs. DNAzymes typically contain a substrate strand that includes a single RNA base and an enzyme strand. DNAzymes show high catalytic hydrolytic cleavage activities toward specific substrates (e.g., targets). In the presence of the specific target, the target will bind to the enzyme strand, resulting in a conformational change in the DNAzyme, and cleavage of the substrate strand at the RNA base. DNAzymes can be conjugated to IR700 molecules using routine methods and used in the methods provided herein, for example to remove, isolate, or separate a target molecule in vitro or in vivo.

DNAzymes are available that have high specificity toward various metal ions such as Pb$^{2+}$ (Breaker, and Joyce, *Chem. Biol.* 1994, 1:223-9; Li and Lu, *J. Am. Chem. Soc.* 2000, 122, 10466-7), Cu$^{2+}$ (Carmi et al., *Chem. Biol.* 1996, 3:1039-46; Cuenoud et al., *Nature* 1995, 375:611-14), Zn$^{2+}$ (Santoro et al., *J. Am. Chem. Soc.* 2000, 122, 2433-243; Li et al., *Nucleic Acids Res.* 2000, 28, 481-488), Co$^{2+}$ (Mei et al., *J. Am. Chem. Soc.* 2003, 125:412-20; Bruesehoff et al., *Comb. Chem. High Throughput Screening* 2002, 5:327-35), Mn$^{2+}$ (Wang et al., *J. Am. Chem. Soc.* 2003, 125, 6880-1), and UO$_2^{2+}$ (Liu et al., *Proc. Nat. Acad. Sci. U.S.A.* 2007, 104:2056-61).

Effective amount: An amount of a composition that alone, or together with an additional therapeutic agent(s) (such as a chemotherapeutic agent) sufficient to achieve a desired effect, for example in vitro, in vivo, or ex vivo. The effective amount of the agent (such as an IR700-molecule conjugate or NIR light) can be dependent on several factors, including, but not limited to the sample, source, subject, or cells being treated, the source applied, the severity and type of the condition being treated, the particular therapeutic agent (e.g., the particular IR700-molecule conjugate), and the manner of administration. Effective amounts also can be determined through various in vitro, in vivo or in situ immunoassays. The IR700-molecule conjugate and/or NIR light can be administered in a single dose, or in several doses, as needed to obtain the desired response.

In one example, an effective amount or concentration is one that is sufficient to remove or separate a target from a sample, source, or subject. In one example, a therapeutically effective amount or concentration is one that is sufficient to delay progression, or to cause regression of a disease, or which is capable of reducing symptoms caused by the disease, such as cancer. In one example, a therapeutically effective amount or concentration is one that is sufficient to increase the survival time of a patient with a tumor.

In one example, an effective amount or concentration is one that is sufficient to remove or separate a target from a sample, source, or subject. The one or more targets need not be completely eliminated for the method to be effective. For example, contacting or administering a composition containing an IR700-molecule conjugate with a sample or source or subject followed by irradiation with NIR light can substantially decrease the amount of the target present in the sample, source, or subject, such as a decrease of at least 20%, at least 50%, at least 80%, at least 90%, at least 95%, at least 98%, or even at least 100%, as compared to the amount of the target present prior to contact or administration of the IR700-molecule conjugate.

In one example, an effective amount or concentration is one that is sufficient to reduce or eliminate (and in some examples kill) a target cell from a mixed population of cells in vivo or in vitro. The one or more target cells need not be completely eliminated for the method to be effective. For example, contacting or administering a composition containing an IR700-molecule conjugate with a sample or source or subject followed by irradiation with NIR light can substantially decrease the amount of the target cell present in the cell mixture in a sample, source, or subject, such as a decrease of at least 20%, at least 50%, at least 80%, at least 90%, at least 95%, at least 98%, or even at least 100%, as compared to the amount of the target cells present prior to contact or administration of the IR700-molecule conjugate.

In one example, an effective amount or concentration is one that is sufficient to isolate or purify a target from a sample, source, or subject. The one or more targets need not be completely isolated or purified for the method to be effective. For example, contacting or administering a composition containing an IR700-molecule conjugate with a sample or source or subject followed by irradiation with NIR light can substantially increase the purity of the target, such as a purity of at least 20%, at least 50%, at least 80%, at least 90%, at least 95%, at least 98%, or even at least 100%, as compared to the amount of the purity of the target present prior to contact or administration of the IR700-molecule conjugate.

In one particular example, an effective amount or concentration is one that is sufficient to treat a disease or disorder in a subject, for example by reducing or inhibiting one or more symptoms associated with the disease or disorder. The one or more symptoms do not have to be completely eliminated for the composition to be effective. For example, administering a composition containing an IR700-molecule conjugate to a subject followed by irradiation with NIR light can substantially decrease one or more signs or symptoms of the disease or disorder by at least 20%, at least 50%, at least 60%, at least 70%, at least 80%, at least 90%, at least 95%, at least 98%, or even at least 100% as compared to the signs or symptoms prior to contact or administration of the IR700-molecule conjugate.

In particular examples, an effective amount of an IR700-molecule conjugate for in vitro or ex vivo purposes is at least 0.5 µg/m$^2$, such as at least 1 µg/m$^2$, at least 2 µg/m$^2$, at least 5 µg/m$^2$, at least 10 µg/m$^2$, at least 25 µg/m$^2$, at least 50 µg/m$^2$, at least 100 µg/m$^2$, at least 250 µg/m$^2$, or at least 500 µg/m$^2$, for example 0.5 µg/m$^2$ to 500 µg/m$^2$, 1 µg/m$^2$ to 500 µg/m$^2$, 1 µg/m$^2$ to 50 µg/m$^2$, or 2 µg/m$^2$ to 20 µg/m$^2$. However, one skilled in the art will recognize that higher or lower amounts also could be used, for example depending on the particular IR700-molecule conjugate or the sample.

In particular examples, an effective amount of IR700-molecule conjugate for in vivo purposes 0.5 milligram per 60 kilogram (mg/kg), at least 5 mg/60 kg, at least 10 mg/60 kg, at least 20 mg/60 kg, at least 30 mg/60 kg, at least 50 mg/60 kg, for example 0.5 to 50 mg/60 kg, such as a dose of 1 mg/60 kg, 2 mg/60 kg, 5 mg/60 kg, 20 mg/60 kg, or 50 mg/60 kg, for example when administered iv. In another example, an effective dose of an IR700-molecule conjugate is at least 10 µg/kg, such as at least 100 µg/kg, at least 500 µg/kg, or at least 500 µg/kg, for example 10 µg/kg to 1000 µg/kg, such as a dose of 100 µg/kg, 250 µg/kg, about 500 µg/kg, 750 µg/kg, or 1000 µg/kg, for example when administered intratumorally or ip. In one example, an effective dose of the IR700-molecule conjugate is at least 1 µg/ml, such as at least 5000 µg/ml, such as 20 µg/ml to 100 µg/ml, 100 µg/ml to 500 µg/ml, 100 µg/ml to 5000 µg/ml, such as 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 500 µg/ml, 1000 µg/ml, 2500 µg/ml, or 5000 µg/ml for example when administered as a topical solution. However, one skilled in the art will recognize that higher or lower dosages also could be used, for example depending on the particular IR700-molecule conjugate. In particular examples, such daily dosages are administered in one or more divided doses (such as 2, 3, or 4 doses) or in a single formulation. The disclosed IR700-molecule conjugates can be administered alone, in the presence of a pharmaceutically acceptable carrier, in the presence of other therapeutic agents (such as anti-neoplastic agents).

Generally a suitable dose of irradiation following contacting the IR700-molecule conjugate with a sample or source, or administration of the IR700-molecule conjugate to a subject, is at least 1 J cm$^{-2}$ at a wavelength of 660-710 nm, at least 2 J cm$^{-2}$ at a wavelength of 660-710 nm, at least 4 J cm$^{-2}$ at a wavelength of 660-710 nm, at least 8 J cm$^{-2}$ at a wavelength of 660-710 nm, at least 10 J cm$^2$ at a wavelength of 660-710 nm, at least 16 J cm$^{-2}$ at a wavelength of 660-710 nm, at least 50 J cm$^{-2}$ at a wavelength of 660-710 nm, or at least 100 J cm$^{-2}$ at a wavelength of 660-710 nm, for example 1 to 500 J cm$^{-2}$ at a wavelength of 660-710 nm. In some examples the wavelength is 680-690 nm. In particular examples, multiple irradiations are performed (such as at least 2, at least 3, or at least 4 irradiations, such as 2, 3, 4, 5, 6, 7, 8, 9 or 10 separate administrations), following contacting the IR700-molecule conjugate with a sample or source, or administration of the IR700-molecule conjugate to a subject.

Functional nucleic acids (FNAs): Nucleic acid molecules (such as DNA or RNA molecules) that can be used as enzymes (for catalysis), receptors (for binding to a target), or both. FNAs include ribozyme and DNAzymes (e.g., see Robertson and Joyce, *Nature* 1990, 344:467; Breaker and Joyce, *Chem. Biol.* 1994, 1, 223-229), aptamers (e.g., see Tuerk and Gold, *Science* 1990, 249, 505), aptazymes (e.g., see Breaker, *Curr. Opin. Biotechnol.* 2002, 13, 31), and aptamers. Additional examples are provided herein and are known in the art. FNAs can be conjugated to IR700 molecules using routine methods and used in the methods provided herein, for example to remove, isolate, or separate a target molecule in vitro or in vivo.

IR700 (IRDye® 700DX): A phthalocyanine dye having the following formula:

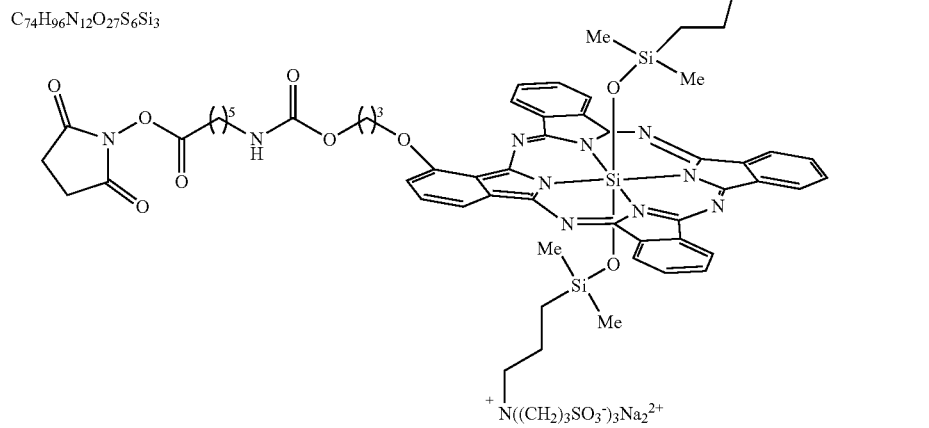

This compound is commercially available from LI-COR (Lincoln, NE). IR700 is a relatively hydrophilic dye and can be covalently conjugated with an antibody (or other protein) using the NHS ester of IR700, and can be conjugated with a nucleic acid molecule using other linker chemistry such as psoralen functionalized IR700 or click chemistry. IR700 also has more than 5-fold higher extinction coefficient ($2.1 \times 10^5$ $M^{-1}$ $cm^{-1}$ at the absorption maximum of 689 nm), than conventional photosensitizers such as the hematoporphyrin derivative Photofrin® ($1.2 \times 10^3$ $M^{-1}$ $cm^{-1}$ at 630 nm), meta-tetrahydroxyphenylchlorin; Foscan® ($2.2 \times 10^4$ $M^{-1}$ $cm^{-1}$ at 652 nm), and mono-L-aspartylchlorin e6; NPe6/Laserphyrin® ($4.0 \times 10^4$ $M^{-1}$ $cm^{-1}$ at 654 nm).

Figure 2:
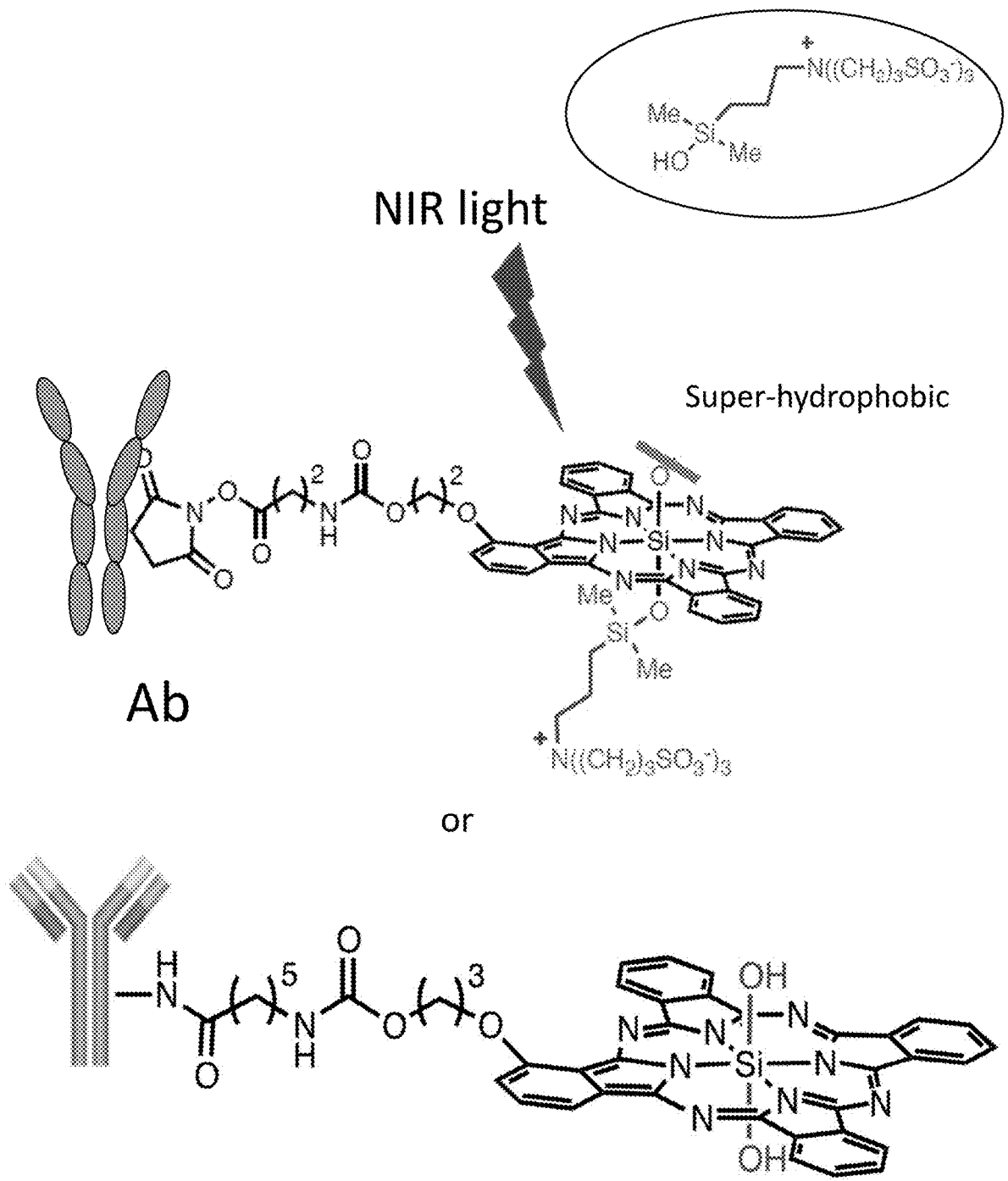
FIG. 2 is a schematic drawing showing IR700 labeled with an antibody (Ab), which when exposed to NIR light, the circled portion of IR700 is cleaved. The resulting compound (non-circled portion) is "superhydrophobic", which leads to aggregation of the antibody (and anything bound to the antibody). This aggregate does not dissociate after SDS treatment (see FIG. 9).

A cleaved or hydrophobic IR700 molecule is one that results after exposure to NIR light (see FIGS. 1 and 2). For example, exemplary cleaved or hydrophilic IR700 molecules include one or more of:

pharmaceutical agent) or specific binding agent (e.g., antibody or fragment thereof, Affibody® molecule, hapten, protein, lectin, nucleic acid molecule, functional nucleic acid, etc.). For example, an IR700-antibody conjugate is a molecule that includes an antibody or antibody fragment, such as a target-specific antibody, conjugated to IR700.

Isolated: An "isolated" agent (such as a protein or nucleic acid molecule) has been substantially separated, produced apart from, or purified away from other components in which the component occurs. For example, the agent, such as a target, can be separated from other components of a sample or source in which the component occurs (such as a biological sample, food sample/source, or environmental sample/source). For example, the agent, such as a target, can be separated from other components of a cell or biological sample (such as a blood sample), such as other chromosomal and extrachromosomal DNA and RNA, and proteins. In

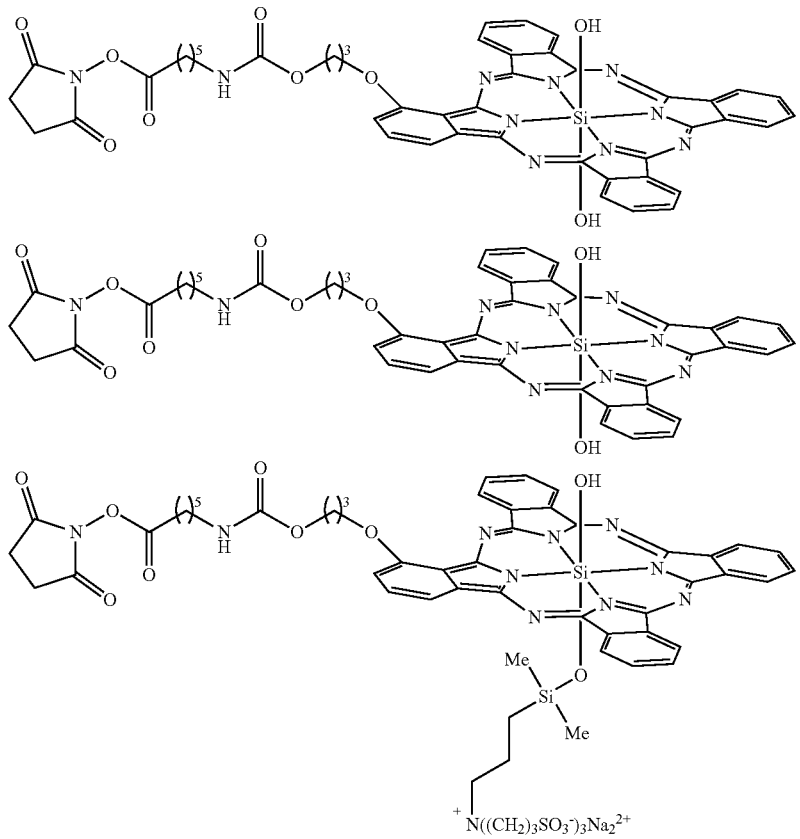

which can have a molecule conjugated to it (such as a molecule or a specific binding agent). The removed piece of IR700 following exposure to NIR light is

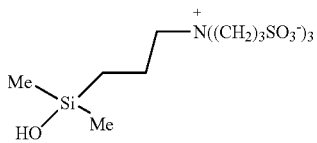

IR700-molecule conjugate: A molecule that includes both an IR700 dye, and another molecule, such as a drug (e.g., some examples, a purified or isolated cell, protein, or nucleic acid molecule can be at least 70%, at least 80%, at least 90%, at least 95%, at least 96%, at least 97%, at least 98%, or at least 99% pure.

Pharmaceutical agent or composition: A chemical compound or composition capable of inducing a desired therapeutic or prophylactic effect when properly administered to a subject in an effective amount. A pharmaceutical composition can include a therapeutic agent, such as one or more IR700-molecule conjugates (in some examples the molecule is a therapeutic agent, such as a chemotherapeutic agent). A therapeutic or pharmaceutical agent is one that alone or together with an additional compound induces the desired response (such as inducing a therapeutic or prophylactic effect when administered to a subject). In a particular example, a pharmaceutical composition includes a therapeutically effective amount of at least one IR700-molecule complex.

Pharmaceutically acceptable carriers: The pharmaceutically acceptable carriers (vehicles) useful in this disclosure are conventional. *Remington's Pharmaceutical Sciences*, by E. W. Martin, Mack Publishing Co., Easton, PA, 19th Edition (1995), describes compositions and formulations suitable for pharmaceutical delivery of one or more compounds, such as one or more IR700-molecule conjugates.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Photoimmunotherapy (PIT): A molecular targeted therapeutic that utilizes a target-specific photosensitizer based on a near infrared (NIR) phthalocyanine dye, IR700, conjugated to specific binding agents such as monoclonal antibodies (MAb) targeting cell surface receptors. In one example the cell surface receptor is one found specifically on a target cell in a mixed cell population, such as a target cell in a tumor, and thus PIT can be used to kill such cells. Cell death of the cells occurs when the antibody-IR700 molecule binds to the cells and the cells are irradiated with NIR, while cells that do not express the cell surface receptor recognized the IR700-molecule conjugate are not killed in significant numbers.

Remove or Separate: To divide or move apart, for example by taking something away.

Sample: Any biological, food, or environmental specimen (or source) that may contain (or is known to contain or is suspected of containing) a target agent can be used in the methods herein.

Subject or patient: A term that includes human and non-human mammals. In one example, the subject is a human or veterinary subject, such as a mouse, non-human primate, cat, dog, and the like. In some examples, the subject is a mammal (such as a human) who has cancer, or is being treated for cancer. In some examples, the subject is a mammal who has an undesired target, such as infection by a pathogen, exposure to a toxin, venom or spore, and the like. In some examples, the subject is a mammal who will receive a pharmacological agent.

Target (or target agent): In one example, it is a substance whose removal or separation is desired, including, but not limited to, a chemical compound, metal (such as a heavy metal), pathogen, toxin, venom, nucleic acid (such as DNA or RNA), or protein (such as a cytokine, hormone or antigen), as well as particular cells (such as a cancer cell, bacterial cell or specific cell in the blood), or spores. In one example, it is a substance whose pharmacokinetics is to be controlled, such as a therapeutic pharmaceutical agent, such as a chemotherapeutic agent.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated with the claimed methods include solid tumors, such as breast carcinomas (e.g. lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, and lymphatic tumors (including B-cell and T-cell malignant lymphoma). In one example, the tumor is an adenocarcinoma.

The methods can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), lymphomas (such as Hodgkin's lymphoma and non-Hodgkin's lymphoma), and myelomas).

Under conditions sufficient for (that permit): A phrase that is used to describe any environment that permits or allows the desired activity. In one example, "under conditions sufficient for" includes contacting an IR700-molecule conjugate with a sample, such as a biological, environmental or food sample, sufficient to allow the IR700-molecule conjugate to bind to one or more targets in the sample. In particular examples, the desired activity is forming an aggregate thereby allowing removal of a target agent, following exposing the sample to NIR light. In one example, "under conditions sufficient for" includes administering an IR700 molecule conjugate to a subject sufficient to allow the IR700-molecule conjugate to bind to a target in vivo. In particular examples, the desired activity is the removal of an undesired target to which the IR700-molecule conjugate is bound, following irradiation of the subject with NIR light. In one example, "under conditions sufficient for" includes administering an IR700 molecule conjugate to a subject sufficient to allow the IR700-molecule to have a therapeutic effect in vivo. In particular examples, the desired activity is the removal of the IR700-molecule conjugate following the treatment, by irradiating the subject with NIR light.

Untreated: A cell, sample, or subject that has not been contacted with a desired agent, such as an IR700-molecule conjugate. In an example, an untreated cell, sample, or subject is one that receives the vehicle or carrier in which the IR700-molecule conjugate was delivered.

Disclosure of certain specific examples is not meant to exclude other embodiments. In addition, any methods or treatments described herein are not necessarily exclusive of other methods, but can be combined with other bioactive agents or treatment modalities.

Overview of Technology

The dye IR700 is a photosensitizer, excited in the near infrared (NIR) range. The inventors have determined that exposure of IR700 dye to NIR light of the appropriate wavelength results in cleavage of the portion of the IR700 molecule (FIG. 1). This cleavage makes the one or more of the resulting "super-hydrophobic" IR700 compounds:

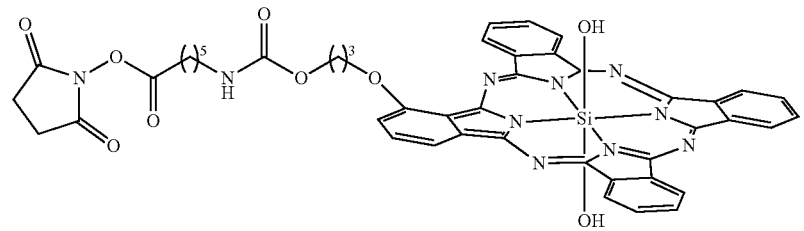

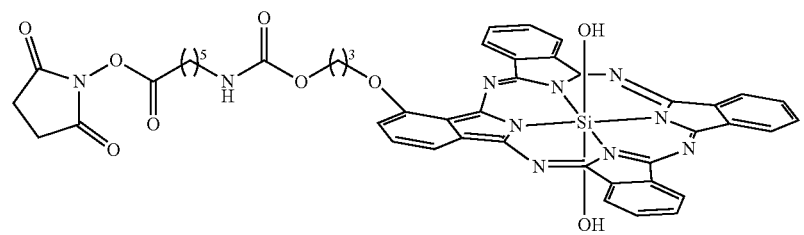

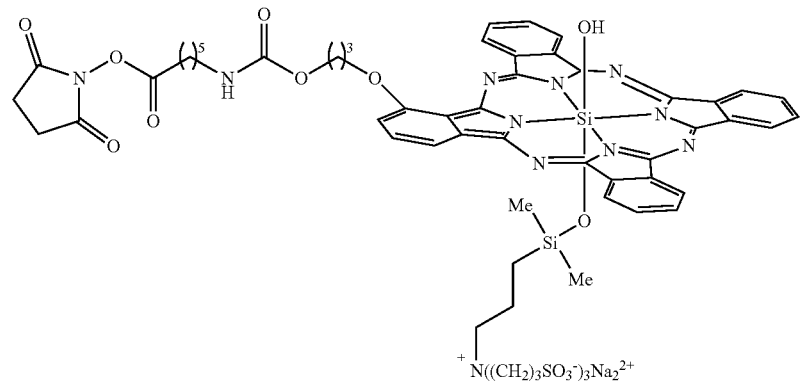

Figure 3:
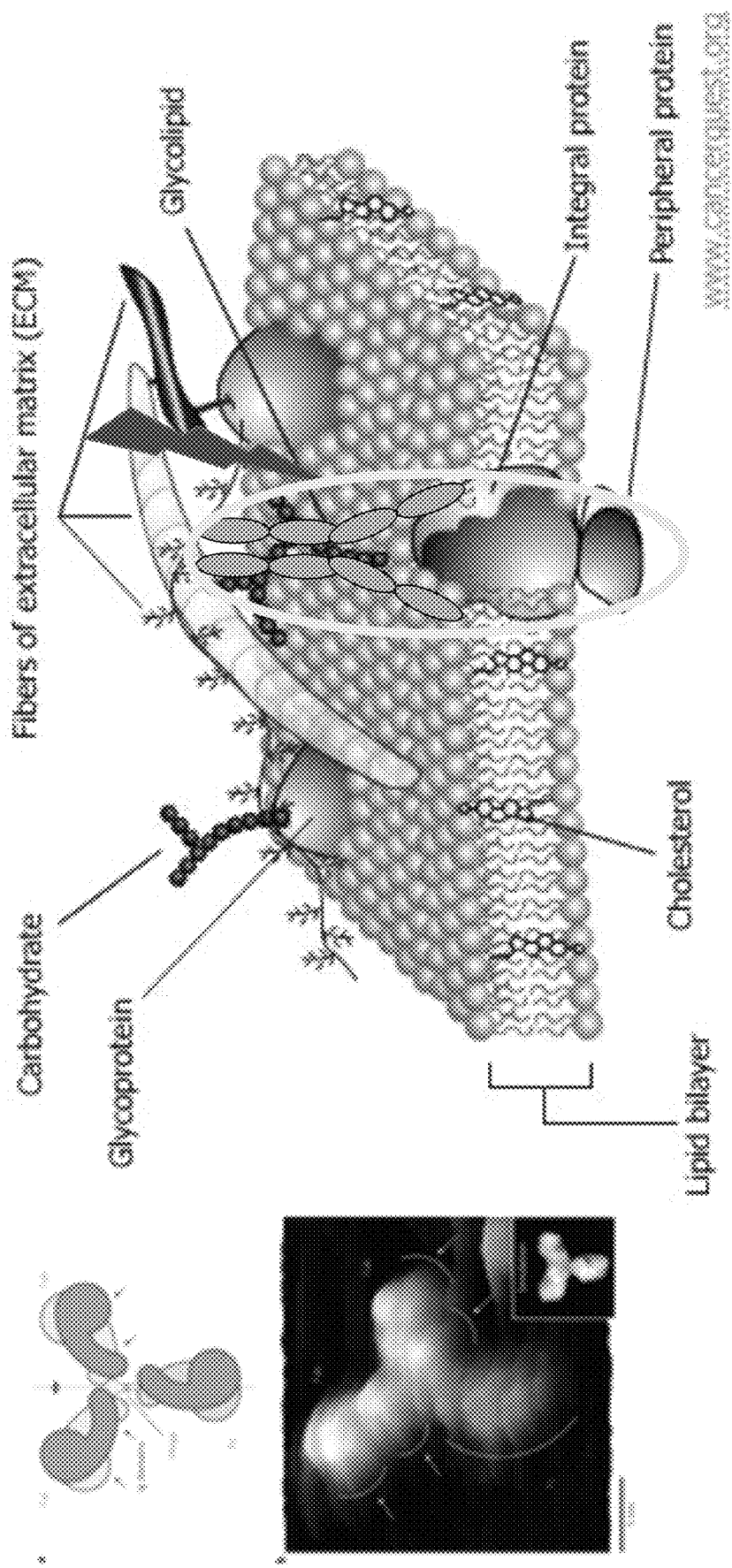
FIG. 3 is a schematic drawing showing a basic cell membrane, with an antibody complex bound to a surface protein. The antibody can be conjugated to IR700. Following exposure to NIR, the IR700 attached to the antibody are chemically changed inducing hydrophobicity, which destroys the integrity of the cell membrane leading to membrane damage.

This hydrophobicity leads to aggregation of the hydrophobic IR700 compound shown above, and any associated molecules. For example, as shown in FIG. 2, an antibody conjugated to IR700 (IR700-antibody conjugate) remains bound to the resulting hydrophobic IR700 compound. In addition, any protein specifically bound to the hydrophobic IR700-antibody conjugate would also remain bound. As shown in FIG. 3, if the IR700-antibody conjugate is bound to a protein on the cell surface, following exposure to NIR, the IR700 attached to the antibody is chemically changed inducing hydrophobicity, which destroys the integrity of the cell membrane leading to membrane damage and cell death. Hydrophilic derivatives of silica-phthalocyanine with similar structure based on silica-oxygen bonds will have a similar result to IR700, and thus can be used in place of IR700 herein. One example of such a compound is La Jolla Blue (see Peng and Braney, Fluorescence Labeling, 2004).

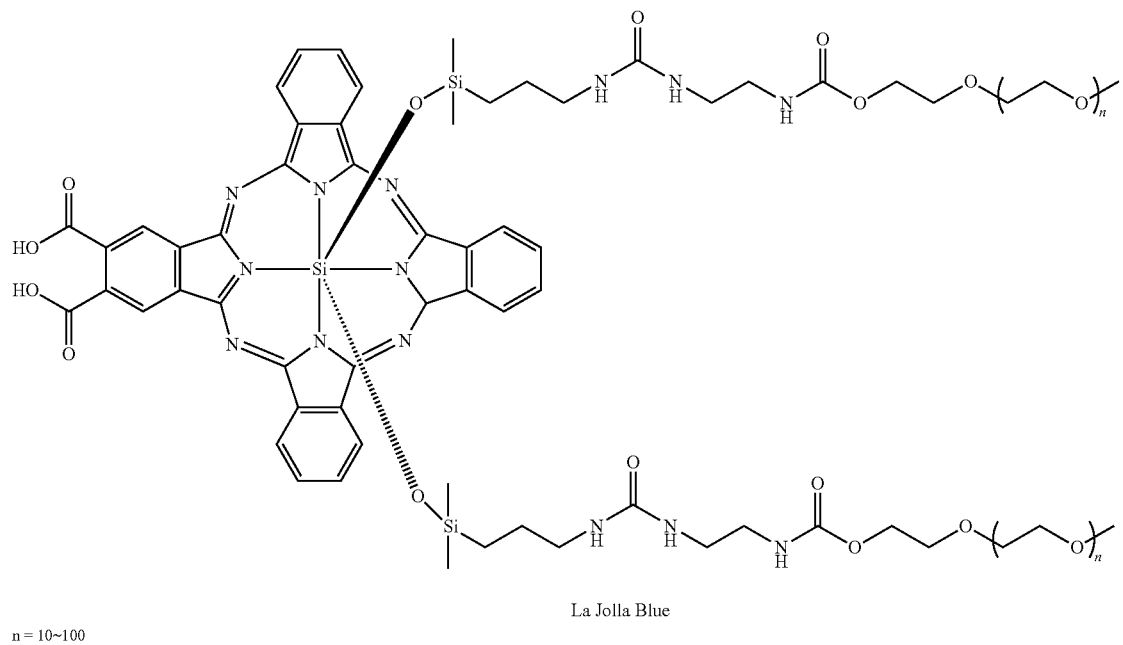

La Jolla Blue n = 10~100

Based on this observation, the present disclosure provides methods for removal (e.g., separation or isolation) of the resulting hydrophobic IR700 complex from solution (for example, by precipitation or centrifugation) or removal (e.g., separation or isolation) of the hydrophobic IR700 complex from the circulation in a subject, for example by trafficking of the hydrophobic IR700 complex to the liver and subsequent degradation of the complex by the liver.

Methods of Removing a Target From a Sample

Provided herein are methods of removing, such as isolating or separating, one or more target molecules or agents from a sample, such as a food sample (or source), environmental sample (or source), fermentation or reactor sample (or source), or sample obtained from a subject. For example, the method can be used to remove or isolate at least two different targets, such as at least 3, at least 4, or at least 5 different targets, such as 1, 2, 3, 4, 5, 6, 7, 8, 9 or 10 different targets from the sample. For example, at least 2, at least 3, at least 4, or at least 5 (such as 1, 2, 3, 4, 5, 6, 7, 8, 9 or 10) different IR700 molecule conjugates can be used on the same sample (e.g., simultaneously or contemporaneously), wherein each is specific for a different target. This permits removal of multiple targets from the sample. Exemplary targets that can be removed or separated from the sample include, but are not limited to proteins, peptides, lectins, carbohydrates, metals (such as heavy metals), nucleic acid molecules, small organic molecules, drugs, venom, pathogens (e.g., virus, parasite, bacterium, or fungus), or a cell (such as a target cell in a mixed population of cells). In some examples, the method also includes detecting the removed target.

In one example, such methods are used to remove unwanted agents (such as impurities, metals, pathogenic organisms, spores, toxins, drugs, cells, and the like), from a sample. For example, impurities can be removed or separated from a sample or source generated as part of a manufacturing process (such as a drug manufacturing process). In another example, pathogens, toxins, spores, metals, or other undesirable agents are removed from an environmental sample or source. In one example, pathogens, toxins, spores, antibiotics, or other undesirable agents are removed from a food sample or source. In one example, undesirable target cells are removed (and in some examples killed) from a tissue or organ culture that includes a plurality of different cell types.

In one example, such methods are used to remove desired agents (such as a target cell, pathogen, metal, spore, protein, nucleic acid molecule, and the like), from a sample. For example, such methods can be used to remove, separate, or isolate a desired cell from a patient, such as from a blood sample. For example, PBMCs or stem cells (such as human stem cells) can be removed from a blood sample using appropriate CD-specific antibodies (wherein the PBMCs or stem cells can be manipulated ex vivo if desired, and re-introduced into a subject, such as one receiving a transplant). In one example, such methods are used to remove a target from a sample (e.g., similar to an immunoprecipitation), which in some examples is further used to identify other agents that bind to the target (e.g., similar to a co-immunoprecipitation). Thus, for example, the methods can be used to remove a target protein, lectin, carbohydrate, pathogen, nucleic acid molecule, cell, or antibody from a sample, such as a sample in a laboratory. In some examples, other agents that bind to the target protein, lectin, carbohydrate, pathogen, nucleic acid molecule, cell, or antibody are identified. In some examples, such methods can be used to concentrate or enrich a target cell or reagent present in a sample, such as a target cell, pathogen, metal, spore, protein, venom, nucleic acid molecule, and the like (such as enriching or concentrating the target by at least 2-fold, at least 5-fold, at least 10-fold, at least 50-fold, at least 100-fold, or at least 500-fold). In some examples, unwanted contaminant or mutated cells in a cell culture, during for example, tissue regeneration applications, can be removed with using the disclosed methods.

Complete removal, isolation or separation of the target from the sample is not required for the method to be effective. For example, the method can include reducing an amount of target agent in the sample (or source) by at least 20%, at least 25%, at least 30%, at least 40%, at least 50%, at least 75%, at least 80%, at least 90%, at least 95%, at least 96%, at least 97%, at least 98%, at least 99%, at least 99.9% (and in some examples 100%), for example as compared to an amount of target present prior to adding an IR700-molecule conjugate to the sample and irradiation of the sample with NIR light. In some examples the method isolates or enriches or concentrates a target, such that the target is at least 20% pure, such as at least 25%, at least 30%, at least 40%, at least 50%, at least 75%, at least 80%, at least 90%, at least 95%, at least 96%, at least 97%, at least 98%, or at least 99% pure, for example as compared to the purity or concentration of the target without adding an IR700-molecule conjugate to the sample and irradiation of the sample with NIR light.

In particular examples, the method includes contacting the sample with an IR700-molecule conjugate. The molecule of the IR700-molecule conjugate can be a specific binding agent that has specificity for the target, and thus preferentially binds to the target relative to other molecules. Non-limiting examples of specific binding agents include antibodies and fragments thereof, Affibody® molecules, haptens, functional nucleic acid molecules (such as aptamers and DNAzymes), nucleic acid molecules (e.g., those having a sequence complementarity to a target nucleic acid molecule such that the nucleic acid molecules hybridize to one another), lectins (carbohydrate-binding proteins), proteins, and the like. If the target is present in the sample, this will result in the formation of an IR700-molecule conjugate-target complex. In particular examples, the IR700-molecule conjugate and the IR700-molecule conjugate-target complex are hydrophilic prior to exposure to NIR light.

The sample is irradiated with NIR, such as at a wavelength of 660 nm to 710 nm (such as 680 or 690 nm), for example at a dose of at least 1 J cm$^{-2}$, under conditions sufficient to cleave off (remove) a portion of the IR700 part of the IR700-molecule conjugate-target complex (e.g., see circled portion of FIG. 2), thereby generating a hydrophobic IR700-molecule conjugate-target complex. In some examples, the following is removed from the IR700-molecule conjugate-target complex following exposure to NIR light:

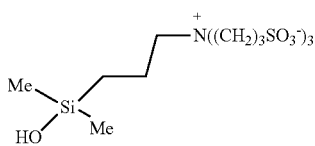

Figure 5:
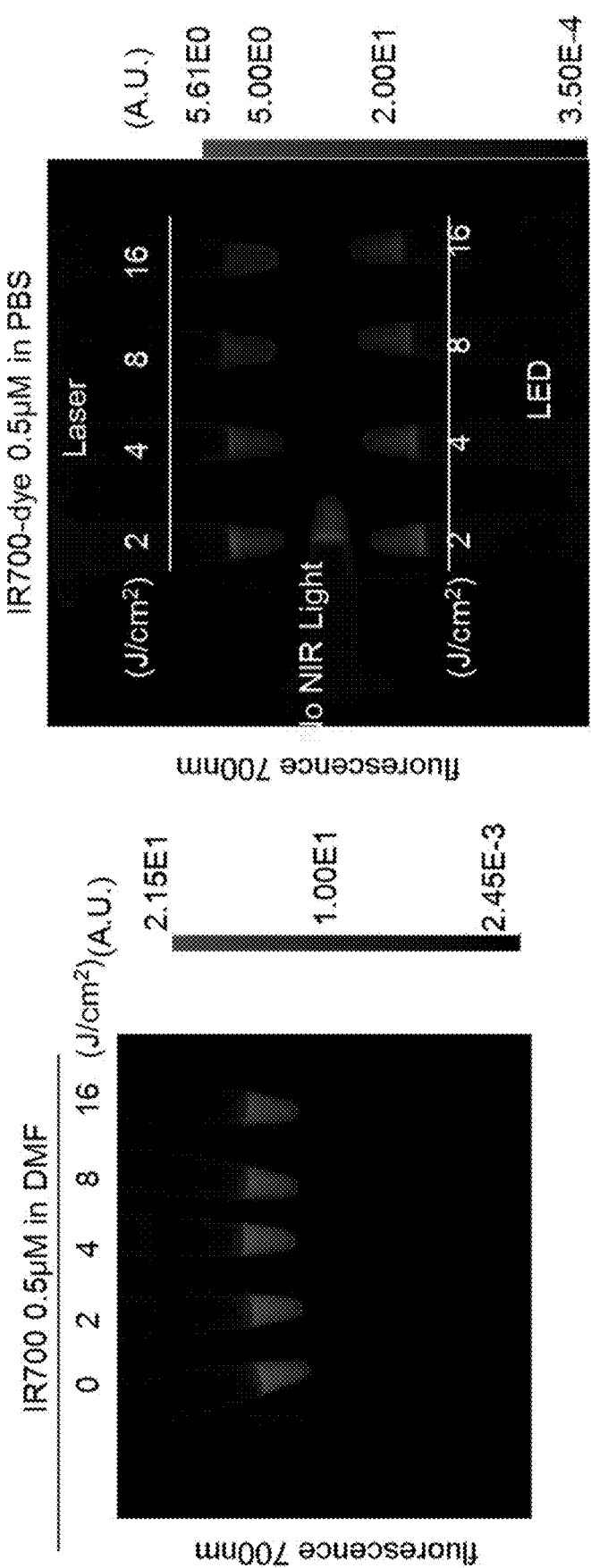
FIG. 5 provides digital fluorescent images showing that despite the cleavage of IR700 following exposure to NIR light, the fluorescent component of the molecule is not affected.

Thus, the IR700-molecule conjugate changes from a hydrophilic molecule to one that is hydrophobic, following exposure to NIR light. As a result, the IR700-molecule conjugate aggregates following exposure to NIR light, permitting separation or removal of the target from the sample (it is in the aggregate or precipitate). The solubility and aggregation properties of silicon phthalocyanines are highly influenced by the nature of the axial substituent (Dyes and Pigments, 2013, 99:59-66). Silicon phthalocyanines without axial substituents, for example the parent compound silicon phthalocyanine dihydroxide (CAS #19333-15-4), have no measurable solubility in a variety of solvents, including water (Yang et al., *J. Phys. Chem. A.,* 2011, 115:12474). As shown in FIG. 5, prior to exposure to NIR light, IR700 can dissolve in different aqueous and organic solvents (hydrophilic).

The resulting hydrophobic IR700-molecule conjugate-target complex can then be removed (e.g., isolated or separated) from the sample. For example, the sample can be incubated or reacted under conditions that permit the hydrophobic IR700-molecule conjugate-target molecule complex to aggregate or form a precipitate (e.g., form a solid in solution). Such conditions can include mixing the solution (e.g., by vortexing, mixing with a stir bar, rocking, or the like) containing the hydrophobic IR700-molecule conjugate-target. In some examples, the solution containing the hydrophobic IR700-molecule conjugate-target is simply allowed to sit at room temperature until the hydrophobic IR700-molecule conjugate-target forms an aggregate or precipitate (such as at least 30 seconds, at least 1 minute, at least 2 minutes, at least 5 minutes, at least 10 minutes, at least 15 minutes, or at least 30 minutes, such as 1 to 5 minutes, 1 to 2 minutes, 1 to 10 minutes, or 10 to 20 minutes). In some examples, the in vitro or ex vivo methods are performed at a temperature of at least 4° C., at least 20° C., at least 30° C., at least 35° C., at least 37° C., or at least 40° C., such as about 4° C. to 37° C., or 25° C. to 37° C.

The hydrophobic IR700-molecule conjugate-target is separated or removed from the sample, thereby isolating the target molecule from the sample. Methods for separating a precipitate or aggregate from a solution are known, and can include but are not limited to centrifugation (e.g., spinning), filtration, chromatography, allowing the precipitate to settle, or combinations thereof. For example, the sample can be centrifuged under conditions that permit the hydrophobic IR700-molecule conjugate-target to pellet to the bottom of a vessel or container, and the resulting supernatant (which is substantially free of the target) collected or removed. Thus, the resulting supernatant can be free (or substantially free) of an undesired target. In some examples, the resulting pellet is analyzed, for example to determine if the target was present in the sample, or to identify other agents bound to the target. As an alternative (or in addition to) centrifugation, in some examples, the sample can be filtered under conditions that permit the hydrophobic IR700-molecule conjugate-target to bind to or be trapped by the filter, and the resulting supernatant (which is free or substantially free of the target) collected. In some examples, the filter is analyzed, for example to determine if the target was present in the sample, or to identify other agents bound to the target. In some examples, the sample is simply allowed to sit or rest under conditions that permit the hydrophobic IR700-molecule conjugate-target to pellet or aggregate at the bottom of a container, and the resulting supernatant (which is substantially free of the target) collected. In some examples, the pellet is analyzed, for example to determine if the target was present in the sample, or to identify other agents bound to the target.

In some examples, the method involves treating the sample multiple times with the method, such as repeating one or more of the contacting with the IR700-molecule conjugate, irradiating with NIR light, aggregation of the hydrophobic IR700-molecule conjugate, and separating the hydrophobic IR700-molecule conjugate from the sample, at least two times, at least 3 times, at least 4 times, at least 5 times, at least 10 times, or at least 20 times.

In some examples, the method further includes measuring or detecting the target removed from the sample. Such measurements can be quantitative or qualitative.

In some examples, the method further includes detecting or measuring other molecules bound to the target. For example, the pellet or filter, or other material/vessel containing the target bound to hydrophobic IR700, can be analyzed. In some examples, the filer or other material is washed or otherwise treated to release any hydrophobic IR700-molecule conjugate-target bound or attached to the filter or other material. In some examples, the pellet, filter, or material released from the filter is analyzed using immunological methods to identify other proteins bound to the target, such as immunohistochemistry, western blotting, spectrometry (such as mass spectrometry, IR, Raman, or FT-IR), chromatography (such as liquid chromatography) and the like. In some examples, the pellet, filter, or material released from the filter is analyzed using hybridization or sequencing methods to identify nucleic acid molecules bound to the target, such as in situ hybridization, Northern blotting, Southern blotting, PCR, and the like.

Exemplary Samples

Any biological, food, or environmental specimen that may contain (or is known to contain or is suspected of containing) a target agent can be used in the methods herein. Samples can also include fermentation fluid, reaction fluids (such as those used to produce desired compounds, such as a pharmaceutical agent), and tissue or organ culture fluid.

Biological samples are usually obtained from a subject and can include genomic DNA, RNA (including mRNA), protein, cells, or combinations thereof. Examples include a tissue or tumor biopsy, fine needle aspirate, bronchoalveolar lavage, pleural fluid, spinal fluid, saliva, sputum, surgical specimen, lymph node fluid, ascites fluid, peripheral blood (such as serum or plasma), bone marrow, urine, saliva, buccal swab, and autopsy material. Techniques for acquisition of such samples are well known in the art (for example see Schluger et al. *J. Exp. Med.* 176:1327-33, 1992, for the collection of serum samples). Serum or other blood fractions can be prepared in the conventional manner. Thus, using the methods provided herein, target molecules in the body can be detected and/or can be removed (for example can be removed from the blood or bone marrow), such as a cell (e.g., PBMC, HSC, lymphocytes), protein, nucleic acid, carbohydrate, lectin, pathogen, toxin, metal, drug, or other target. In some examples, the methods are be used to remove normal cells from a sample (such as lymphocytes, monocytes, macrophages, dendritic cells and stem cells) that may cause disorders by amplifying or suppressing the normal immune response. By removing such cells, the normal immune response can be restored locally. Alternatively, cells can be removed so as to allow their replacement with other, exogenously administered cells as occurs in cell based therapies. The target cell-depleted sample can be returned to the same or a different subject if desired. In some examples, the sample is a tissue culture or organ culture containing at least two different cell types (such as at least 3, at least 4, at least 5, or at least 10 different cell types, wherein one of the cell types is the target cell to be removed.

Environmental samples include those obtained from an environmental media, such as water, air, soil, dust, wood, plants, or food (such as a swab of such a sample). In one example, the sample is a swab obtained from a surface, such as a surface found in a building or home. Thus, using the methods provided herein, harmful products found in the environment can be detected and can be removed (e.g., removed from an environmental source), such as a pathogen, toxin, metal, or other harmful product. In some examples, the disclosed methods detect and/or remove one or more pharmaceutical drug contaminants (e.g., those in an aquatic environment), such as antibiotics, hypertensive medication, antidepressants, analgesics, reproductive hormones, or other prescription drugs.

In one example the sample is a food sample, such as a meat, dairy, fruit, or vegetable sample. For example, using the methods provided herein, adulterants in food products can be detected and can be removed (e.g., removed from a food product), such as a pathogen or toxin or other harmful product. For example, beverages (such as milk, cream, soda, bottled water, flavored water, juice, and the like), and other liquid or semi-liquid products (such as yogurt) can be treated with the methods provided herein. In some examples, the liquid used to decontaminate a food article, such as meat, vegetables, or fruit, is treated with the disclosed methods to remove impurities or harmful agents from the used liquid.

In one example the sample is a sample from a chemical reaction, such as one used to produce desired compounds, such as a pharmaceutical agent. For example, using the methods provided herein, undesired agents generated during the chemical reaction, or contaminants, can be detected and can be removed. In some examples, such methods are used to further purify the end product. For example, heavy metal byproducts can be removed from such reactions using an IR-700-specific binding molecule conjugate, such as an IR700-molecule conjugate that includes a metal coordinating group (e.g., EDTA, DTPA, DOTA).

In other examples, a sample includes a control sample, such as a sample known to contain, or not contain, a particular amount of the target.

Once a sample has been obtained, the sample can be used directly, concentrated (for example by centrifugation or filtration), purified, liquefied, diluted in a fluid, or combinations thereof. In some examples, proteins, cells, nucleic acids, or pathogens are extracted from the sample, and the resulting preparation (such as one that includes isolated cells, pathogens, DNA, RNA, and/or proteins) analyzed using the methods provided herein.

Irradiation of Sample or Source

After the sample is contacted with one or more IR700-molecule conjugates, it is irradiated with NIR light. Methods of irradiation are known in the art. In some examples, a sample is irradiated in vitro, such as in a tissue culture dish, test tube, multi-well plate, fermentation reactor, eppendorf tube, petri dish, medical tubing and bags, and the like. In some examples, a food sample or product (such as a batch of milk, piece of fruit or a vegetable, or meat) is irradiated. In some examples, an environmental sample or area (such as an area of land, water, soil, or air) is irradiated. In some examples, a fermentation or other reaction solution (such as one producing a desired product) is irradiated.

In other examples, a sample is irradiated ex vivo, for example irradiating a sample obtained from a subject (such as a blood sample or fraction thereof). In some such examples that subject has previously been administered IR700-molecule conjugates, or the IR700-molecule conjugate is contacted or incubated with the sample after it is removed from the subject.

The sample is irradiated with a dose of radiation at a wavelength of 660 nm to 710 nm, such as 660 nm to 700 nm, 670 nm to 710 nm, 680 nm to 700 nm, 670 nm to 690 nm, for example, 680 nm or 690 nm. In specific examples, the sample is irradiated with a NIR using an LED or a laser, such as an LED at 690 nm+/−20 nm or a laser system at 690 nm+/−4 nm. In particular examples, the sample is irradiated at a dose of at least 1 J cm$^{-2}$, such as at least 2 J cm$^2$, at least 4 J cm$^{-2}$, at least 8 J cm$^{-2}$, at least 10 J cm$^{-2}$, at least 15 J cm$^{-2}$, at least 30 J cm$^2$, at least 50 J cm$^{-2}$, at least 100 J cm$^{-2}$, or at least 500 J cm$^2$, for example, 1 to 1000 J cm$^{-2}$, 1 to 500 J cm$^2$, 1 to 20 J cm$^{-2}$, 1 to 10 J cm$^2$, 30 to 50 J cm$^{-2}$, 10 to 100 J cm$^{-2}$, 4 to 8 J cm$^{-2}$, 5 to 10 J cm$^2$, or 10 to 50 J cm$^2$.

Samples can be irradiated one or more times. Thus, irradiation can be completed in a single day, or may be done repeatedly on multiple days with the same or a different dosage (such as irradiation at least 2 different times, 3 different times, 4 different times 5 different times or 10 different times). Repeated irradiations may be done on the same day, on successive days, or every 1-3 days, every 3-7 days, every 1-2 weeks, every 2-4 weeks, every 1-2 months, or at even longer intervals.

Methods for Removing a Target from a Subject

Methods similar to the in vitro methods described above can be performed in vivo. Provided herein are methods of removing, such as isolating or separating, one or more target molecules or agents from a subject, such as a mammal, such as a human, mouse, primate, cat, dog, or other veterinary subject. For example, the method can be used to remove or isolate at least two different targets, such as at least 3, at least 4 or at least 5 different targets, such as 1, 2, 3, 4, 5, 6, 7, 8, 9 or 10 different targets from the subject. For example, at least 2, at least 3, at least 4, or at least 5 (such as 1, 2, 3, 4, 5, 6, 7, 8, 9 or 10) different IR700 molecule conjugates can be used in the same subject (e.g., simultaneously or contemporaneously), wherein each is specific for a different target. This permits removal of multiple targets from the subject. Exemplary targets that can be removed, isolated, or separated from the subject include, but are not limited to proteins, peptides, lectins, carbohydrates, metals (such as heavy metals), nucleic acid molecules, small organic molecules, drugs (such as a recreational drug or a therapeutic/pharmacological drug), venom, pathogens (e.g., virus, bacterium, or fungus), or a cell (such as a cell in a mixed population of cells, such as a target cell in a tumor). In some examples, the method also includes detecting the removed target after it has been removed from the subject, detecting a reduction of the target in the subject after the treatment, or both.

In one example, such methods are used to remove unwanted agents (such as metals, pathogenic organisms, spores, toxins, venom, cells, recreational drugs, a therapeutic drug, proteins, nucleic acid molecules, and the like), from a subject. For example, unwanted agents can be removed from a subject by using an IR700-molecule conjugate, wherein the molecule of the conjugate is a specific binding agent for the target to be removed. In some examples, the unwanted agent that is removed from the subject is a metal that is toxic to the patient, such as a heavy metal, wherein the molecule of the IR700-molecule conjugate is a specific binding agent for the metal to be removed (e.g., binds to lead or mercury). In some examples, the unwanted agent that is removed from the subject is a pathogen, such as a virus, fungus, parasite, bacterial cell and the like, wherein the molecule of the IR700-molecule conjugate is a specific binding agent for the pathogen to be removed (e.g., binds to a specific pathogenic protein or nucleic acid). In some examples, the unwanted agent that is removed from the subject is a venom, for example from a subject that has been bitten or stung by a venomous animal (e.g., spider, scorpion, ant, snake, fish, bee, or wasp), wherein the molecule of the IR700-molecule conjugate is a specific binding agent for the venom to be removed (e.g., binds to snake venom). In some examples, the unwanted agent that is removed from the subject is a recreational drug, for example from a subject that has overdosed, wherein the molecule of the IR700-molecule conjugate is a specific binding agent for the drug to be removed (e.g., binds to cocaine or heroin).

In some examples, the unwanted agent is a plurality of toxins, such as smaller toxins not removed during kidney dialysis. Thus, the method can be used instead of, or in addition to, kidney dialysis, to remove toxins or other undesired agents from the blood (and thus can be used with subject in kidney failure).

In some examples, the unwanted agent that is removed from the subject is a protein or nucleic acid molecule (such as a protein or nucleic acid whose presence or increase causes or exacerbates a disease, such as an autoimmune disease or cancer), wherein the molecule of the IR700-molecule conjugate is a specific binding agent for the protein or nucleic acid molecule to be removed (e.g., binds to or hybridizes to the protein or nucleic acid molecule, respectively).

In some examples, the unwanted agent is a cell, such as a bacterial cell or other cell whose presence or increase causes or exacerbates a disease (e.g., allergy, autoimmune disease or cancer). Examples of such cells include but are not limited to lymphocytes, dendritic cells, macrophages, and the like, such as those immune cells in a tumor. In one example, activated T cells or other undesirable immune cells are removed from a subject having an autoimmune disease or an allergy. In another example, suppressor-type cells are removed from a subject having cancer. In one example, cancer stem cells are removed from (or depleted in, e.g., killed) a subject having cancer.

In some examples, target immune cells are removed (e.g., killed) from tumor tissue in vivo. Examples of such cells include, but are not limited to negative regulatory T-cells (such as a CD4$^+$CD25$^+$FoxP3$^+$). In one example, such cells are targeted by their expression of foxp3, CD25 (e.g., using the anti-CD25 antibody daclitumab or basiliximab), cytotoxic T-lymphocyte-associated protein 4 (CTLA4) (e.g., using the anti-CTLA4 antibody ipilimumab or tremelimumab), CD52 (e.g., using the anti-CD52 antibody alemtuzumab), CD132 or combinations thereof. Thus, the disclosed methods in some examples kill at least 10%, for example at least 20%, at least 40%, at least 50%, at least 80%, at least 90%, at least 95%, or at least 98%, of the treated CD4$^+$CD25$^+$Foxp3$^+$ Tregs (for example as a % of the total number of CD4$^+$CD25$^+$Foxp3$^+$ Tregs in a subject prior to treatment or a % of the total number of CD4$^+$CD25$^+$Foxp3$^+$ Tregs in the area of a tumor (such as an area that includes the tumor and at least 1 mm (such as at last 2 mm, at least 3 mm, at least 4 mm, or at least 5 mm) surrounding the tumor prior to treatment) relative to the absence of treatment with of one or more antibody-IR700 molecules and NIR. In one example, the two different antibody-IR700 molecules used are specific for two different proteins or antigens, such as one antibody specific for CTLA4, and another antibody specific for CD25. For example, the use of antibody-IR700 molecules in combination with NIR light can reduce the volume of a tumor, the size of a tumor, the weight of a tumor, the number of metastases, volume of a metastases, the size of a metastases, the weight of a metastases, or combinations thereof by at least 20%, at least 25%, at least 30%, at least 40%, at least 50%, at least 75%, at least 90%, or at least 95%, relative to the absence of treatment.

The methods can also be used to remove normal cells from a subject, such as lymphocytes, monocytes, macrophages, dendritic cells and stem cells, which may cause disorders by amplifying or suppressing the normal immune response. By removing such cells the normal immune response can be restored locally. Alternatively, cells can be removed so as to allow their replacement with other, exogenously administered cells as occurs in cell based therapies.

In some examples, unwanted agents can be removed from an organ in the subject, for example by perfusing the organ with one or more desired IR700-molecule conjugates.

In some examples, the unwanted agent that is removed from the subject is a pharmaceutical drug, such as a chemotherapeutic agent, biologic agent (e.g., mAb, antibody drug conjugates, such as those conjugated to toxins, and the like), antibiotic (e.g., penicillin, ampicillin, metronidazole, tetracycline, cipro, and the like), anti-hypertensive drugs (e.g., thiazide diuretics, ACE inhibitors, calcium channel blockers, beta blockers, and angiotensin II receptor antagonists), antidepressants (e.g., selective serotonin reuptake inhibitors (SSRIs), serotonin-norepinephrine reuptake inhibitors (SNRIs), tricyclic antidepressants (TCAs), monoamine oxidase inhibitors (MAOIs), buprenorphine, tryptophan, antipsychotics, St John's wort, for example prozac), analgesics (e.g., acetaminophen, non-steroidal anti-inflammatory drugs (NSAIDs), COX-2 inhibitors, and opioid drugs such as morphine, codeine, and oxycodone), reproductive hormones (e.g., estrogen, testosterone, and progesterone), blood thinners (e.g., warfarin), steroids (e.g., prednisone), statins to reduce cholesterol (e.g., Mevacor, Zocor, Pravachol), and other prescription drugs, wherein the molecule of the IR700-molecule conjugate is the target to be removed (e.g., is the chemotherapeutic agent). For example, such methods can be used to control the pharmacokinetics (e.g., half-life) of a pharmaceutical drug, for example to inactivate it and remove it from the subject after a desired period of time. By conjugating such drugs to the IR700, following irradiation with NIR light, the drug conjugated to the IR700 dye will aggregate and be targeted for removal from the body, for example via the liver and/or spleen. Thus, if the half-life of a drug is longer than desired (which can in some examples cause undesirable build-up of the drug in the body, or can cause undesirable side effects) it can be reduced by exposing the patient to NIR light after the desired period of time following administration of the IR700-drug conjugate, thereby inactivating the drug.

In one example, such methods are used to remove desired agents (such as a target cell, protein, nucleic acid molecule, and the like), from a subject. For example, such methods can be used to remove, separate, or isolate a desired cell from a patient, such as from a blood sample or bone marrow. In some examples, such a method is part of an apheresis procedure. For example, cells, such as PBMCs or stem cells (such as human stem cells) can be removed from a blood sample during or after an apheresis procedure. In one example, blood is removed from a subject, and the desired cells removed or isolated from the blood sample, for example using appropriate CD-specific antibodies. For example, if HSC are desired, the blood sample can be contacted with IR700-CD34 antibody conjugates, which will bind to the HSCs. If PBMCs are desired, the blood sample can be contacted with IR700-CD19 antibody conjugates, which will bind to the PBMCs. Cells removed from the patient can be manipulated ex vivo if desired (for example expanded, manipulated by gene therapy methods, and the like), and re-introduced into the same or a different subject, such as one receiving a transplant). In other examples, contaminating cells in a cell or organ culture can be removed. In some examples, immune cells that are stimulating disease (e.g., autoimmune disease or allergy) or cells inhibiting host response (e.g., as in immune tolerance in cancer) can be removed. In some examples, such methods can be used to remove, separate, or isolate a desired protein (e.g., antibody) or nucleic acid molecule from a subject (such as a human or laboratory animal), such as from a blood sample or bone marrow.

In some examples, the IR700-molecule conjugate and/or the NIR light is contacted with the biological sample after it is removed from the subject, and the sample (or a portion thereof) with the target removed (e.g., desirable targets or undesirable targets) returned to the same subject or a different subject. In some examples, the subject can be administered the IR700 molecule conjugate and exposed to NIR light, and then the resulting aggregates containing the target removed from the subject by removing them from a sample obtained from the subject (for example during an apheresis procure where blood is removed from the subject, aggregates from the blood removed, and the target-free (or substantially target-free) blood returned to the subject (or a different subject).

In one example, such methods are used to remove a target from a subject, which in some examples is further used to identify other agents that bind to the target. Thus, for example, the methods can be used to remove a target pathogen, toxin, drug, protein, lectin, carbohydrate, nucleic acid, antibody, cell, and the like from a subject. In some examples, other agents that bind to the target pathogen, toxin, drug, protein, lectin, carbohydrate, nucleic acid, antibody, cell, and the like are identified following removal from the subject.

Complete removal, isolation or separation of the target from the subject is not required for the method to be effective. For example, the method can include reducing an amount of target agent in the subject by at least 20%, at least 25%, at least 30%, at least 40%, at least 50%, at least 75%, at least 80%, at least 90%, at least 95%, at least 96%, at least 97%, at least 98%, or at least 99%, for example as compared to an amount of target present prior to administration of an IR700-molecule conjugate to the subject and irradiation of the subject with NIR light. In some examples the method isolates a target, such that the target is at least 20% pure, such as at least 25%, at least 30%, at least 40%, at least 50%, at least 75%, at least 80%, at least 90%, at least 95%, at least 96%, at least 97%, at least 98%, or at least 99% pure, for example as compared to the purity or concentration of the target without adding an IR700-molecule conjugate to the subject and irradiation of the subject with NIR light.

In particular examples, the method includes administering one or more IR700-molecule conjugates to a subject, wherein the molecule conjugated to the IR700 includes the target molecule or wherein the molecule conjugated to the IR700 comprises specifically binds to the target molecule (e.g., has specificity for the target, and thus preferentially binds to the target relative to other molecules). Non-limiting examples of specific binding agents include antibodies and fragments thereof, Affibody® molecules, haptens, functional nucleic acid molecules (such as aptamers and DNAzymes), nucleic acid molecules (e.g., those having a sequence complementarity to a target nucleic acid molecule such that the nucleic acid molecules hybridize to one another), lectins (carbohydrate-binding proteins), proteins, and the like. IR700-molecule conjugates can be administered to a subject in the presence of a pharmaceutically acceptable carrier, such as a pharmaceutically and physiologically acceptable fluid, for example under conditions that permit the IR700-molecule conjugates to specifically bind to a target (e.g., in cases wherein the molecule is a specific binding agent), or to have a therapeutic effect (e.g., in cases where the molecule is the target, such as a pharmaceutical drug). For example, the IR700-molecule conjugate can be present in a pharmaceutically effective carrier, such as water, physiological saline, balanced salt solutions (such as PBS/EDTA), aqueous dextrose, sesame oil, glycerol, ethanol, combinations thereof, or the like, as a vehicle. The carrier and composition can be sterile, and the formulation suits the mode of administration.

In cases wherein the molecule of the IR700-molecule conjugate is a specific binding agent, if the target is present in the subject, this will result in the formation of an IR700-molecule conjugate-target complex.

In particular examples, the IR700-molecule conjugate and the IR700-molecule conjugate-target complex are hydrophilic prior to exposure to NIR light. After contacting or administering the one or more IR700-molecule conjugates under conditions that allow the molecule of the IR700-molecule conjugate to bind to its target or that allow the molecule of the IR700-molecule conjugate to have a therapeutic effect, the subject is irradiated under conditions that permit cleavage of the IR700, for example with NIR light, such as at a wavelength of 660 nm to 710 nm (e.g., 680 nm to 690 nm), for example at a dose of at least 10 J cm$^{-2}$. Such conditions cleave off (remove) a portion of the IR700 part of the IR700-molecule conjugate or the IR700-molecule conjugate-target complex (e.g., see circled portion of FIG. 2), thereby generating a hydrophobic IR700-molecule conjugate or a hydrophobic IR700-molecule conjugate-target complex. In one example, there is at least 10 minutes, at least 30 minutes, at least 1 hour, at least 4 hours, at least 8 hours, at least 12 hours, at least 24 hours, at least 48 hours, at least 72 hours, at least 96 hours, at least 1 week, at least 2 weeks, at least 3 weeks, or at least 4 weeks, (such as 1 to 4 hours, 30 minutes to 1 hour, 10 minutes to 60 minutes, or 30 minutes to 8 hours) in between contacting the cell with the IR700-molecule conjugate and the irradiation. The NIR excitation light wavelength allows penetration of at least several centimeters into tissues. For example, by using fiber-coupled laser diodes with diffuser tips, NIR light can be delivered within several centimeters of areas located deep to the body surface. In addition, circulating targets can be targeted since they can be excited when they traverse superficial vessels (for example using the NIR LED wearable devices disclosed herein). In some examples, the subject is irradiated by use of a device worn by (or that covers) the subject, wherein the device includes NIR light emitting diode (LED). In some examples, the following is removed from the IR700-molecule conjugate or the IR700-molecule conjugate-target complex following exposure to NIR light:

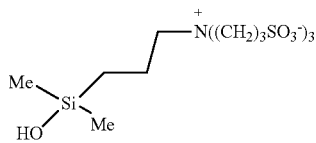

Thus, the IR700-molecule conjugate or the IR700-molecule conjugate-target complex changes from a hydrophilic molecule to one that is hydrophobic, following exposure to NIR light. As a result, the hydrophobic IR700-molecule conjugate or the hydrophobic IR700-molecule conjugate-target complex aggregates following exposure to NIR light, permitting separation or removal of the target from the subject. For example, such aggregates can reach the liver and/or spleen, where they are degraded and targeted for removal (e.g., excretion) from the body.

The resulting hydrophobic IR700-molecule conjugate or the hydrophobic IR700-molecule conjugate-target complex can then be removed (e.g., excreted) from the subject. The method can also include detecting a decrease in the amount of the target molecule in the subject (e.g., measuring an absolute or relative amount of the target in a blood sample obtained from the subject) or detecting an increase in the amount of the target molecule (or a degradation product thereof) excreted from the subject (for example following catabolism in the liver, the excreted target may be detected in the urine or bowel movement). Such measurements of the target can be quantitative or qualitative.

In some examples, the method further includes detecting or measuring other molecules bound to the target after it is removed from the body. For example, the excreted hydrophobic IR700-molecule conjugate or the hydrophobic IR700-molecule conjugate-target complex, can be analyzed, for example using immunological methods to identify other proteins bound to the target, such as immunohistochemistry, western blotting, spectrometry (such as mass spectrometry, IR, Raman, or FT-IR), chromatography (such as liquid chromatography) and the like. In some examples, the pellet, filter, or material released from the filter is analyzed using hybridization or sequencing methods to identify nucleic acid molecules bound to the target, such as in situ hybridization, Northern blotting, Southern blotting, PCR, and the like.

In some examples, the method involves treating the subject multiple times with the method, such as repeating one or more of the administering the IR700-molecule conjugate, irradiating with NIR light, aggregation of the hydrophobic IR700-molecule conjugate, and removal of the hydrophobic IR700-molecule conjugate from the subject, at least two times, at least 3 times, at least 4 times, at least 5 times, at least 10 times, or at least 20 times.

The disclosed methods can be used to remove target agents fixed in the body as well as targets in the circulation (e.g., leukemia cells, metastases, circulating tumor cells). However, circulating targets, by their nature, cannot be exposed to light for very long. Thus, if the target is one that is circulating throughout the body, the methods can be accomplished by using a device that can be worn, or that covers parts of the body. For example, such a device can be worn for extended time periods. Everyday wearable items (e.g., wristwatches, jewelry (such as a necklace or bracelet), blankets, clothing (e.g., underwear, socks, and shoe inserts) and other everyday wearable items) which incorporate NIR emitting light emitting diodes (LEDs) and/or a laser systems (e.g., an argon NIR laser), and a battery pack, can be used. Such devices produce light on the skin underlying the device over long periods leading to continual exposure of light to superficial vessels over prolonged periods. Circulating targets are exposed to the light as they transit thru the area underlying the device. As an example, a wristwatch or bracelet version of this device can include a series of NIR LEDs and/or a laser (e.g., an argon NIR laser), with battery power pack to be worn for most of the day.

For example, after administration of the one or more IR700-molecule conjugates (e.g., intravenously), if appropriate circulating targets (e.g., cells) bind the IR700-molecule conjugates. As these cells or other targets flow within the vessels adjacent to the LED and/or a laser (e.g., an argon NIR laser) present in the everyday wearable item (e.g., bracelet or wristwatch), they would be exposed to NIR light rendering the IR700 and molecule bound thereto susceptible to cleavage and aggregation. The dose of light may be adjustable according to diagnosis and target type.

In some examples, the method also includes administering one or more additional therapeutic agents or treatments. Examples of such additional agents include, but are not limited to: anti-neoplastic agents, such as chemotherapeutic and anti-angiogenic agents or therapies, such as radiation therapy.

Exemplary Subjects

In some examples the disclosed methods are used to remove a target from a subject. In one example, the IR700-molecule conjugate includes a specific binding agent that can bind to or hybridize to the target. Such IR700-molecule conjugates are useful for subjects having a disorder resulting from the presence or increased amount of the target, such as one who is infected with a target pathogen, one who has been bitten or stung by a venomous animal, one who has a disorder resulting from the presence of undesired cells (such as cancer or an autoimmune disorder or an allergy), one who has a disorder resulting from the presence of, or increased amounts of a target protein, cell or nucleic acid molecule, one who has had an overdose of a drug target, and the like. In one example, the subject is a human or laboratory animal, such as a rabbit or mouse, having a desired target antibody, protein, cell, or nucleic acid molecule, to be isolated.

In one example, the IR700-molecule conjugate includes a therapeutic drug. Such IR700-drug conjugates are useful for subjects or example a subject who has a disorder that would benefit from treatment with the target drug (e.g., a pharmacological drug).

In one example the subject has cancer, such as cancer of the breast, liver, kidney, uterus, colon, ovary, prostate, pancreas, brain, cervix, bone, skin, or lung.

The disclosed methods can be used in any mammalian subject, such as a human or veterinary subject. In some examples, the subject is one who has received other therapies, but those other therapies have not provided a desired therapeutic response. In some examples the method includes selecting a subject that will benefit from the disclosed therapies.

Administration of IR 700-Molecule Conjugates

IR700-molecule conjugates and additional therapeutic agents (such as anti-neoplastic agents) can be contacted with a sample in vitro, for example by adding the IR700-molecule conjugates to growth media in which the cells or growing, or can be contacted with a cell in vivo, for example by administering the IR700-molecule conjugates to the subject to be treated.

The IR700-molecule conjugates can be administered locally or systemically using any method known in the art. Although specific examples are provided, one skilled in the art will appreciate that alternative methods of administration of the disclosed IR700-molecule conjugates and additional therapeutic agents can be used. Such methods may include for example, the use of catheters or implantable pumps to provide continuous infusion over a period of several hours to several days into the subject in need of treatment.

In one example, the IR700-molecule conjugates are administered by parenteral means, including direct injection direct injection or infusion into a tumor (intratumorally). In addition, or alternatively, the disclosed IR700-molecule conjugates can be administered systemically, for example intravenously, intramuscularly, subcutaneously, intradermally, intraperitoneally, subcutaneously, or orally, to a subject having a tumor (such as cancer).

The dosage of the IR700-molecule conjugates to be administered to a subject are not subject to absolute limits, but will depend on the nature of the composition and its active ingredients and its unwanted side effects (e.g., immune response against a specific binding agent), the subject being treated and the type of condition being treated and the manner of administration. Generally the dose will be a therapeutically effective amount, such as an amount sufficient to achieve a desired biological effect, for example an amount that is effective to substantially remove the target from the subject (e.g., remove at least 20%, at least 30%, at least 40%, at least 50%, at least 60%, at least 70%, at least 80%, at least 90%, at least 95%, or at least 99%, such as 80 to 100%, 80 to 99.9%, 90 to 95%, or 90 to 99%). Dosages of additional therapeutic agents (such as antibiotics, antivirals, immunosuppressants, and the like) that can be used in combination with the disclosed methods are known in the art.

For intravenous administration of the IR700-molecule conjugates, exemplary dosages for administration to a subject for a single treatment can range from 0.5 to 100 mg/60 kg of body weight, 1 to 100 mg/60 kg of body weight, 1 to 50 mg/60 kg of body weight, 1 to 20 mg/60 kg of body weight, for example about 1 or 2 mg/60 kg of body weight. In yet another example, a therapeutically effective amount of ip or intratumoral administered IR700-molecule conjugates can vary from 10 μg to 5000 μg of IR700-molecule conjugates to 1 kg of body weight, such as 10 μg/kg to 1000 μg/kg, 10 μg/kg to 500 μg/kg, or 100 μg/kg to 1000 μg/kg.

In one example, the dose of an IR700-molecule conjugates administered to a human patient is at least 50 mg, such as at least 100 mg, at least 300 mg, at least 500 mg, at least 750 mg, or even 1 g.

Treatments with disclosed IR700-molecule conjugates (and additional therapeutic agents) can be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

Irradiation of Subjects or Cells

After the subjects and/or cells are contacted with one or more IR700-molecule conjugates, they are irradiated. Methods of irradiation are well known in the art. In some examples, cells are irradiated in vitro after removal from the subject, such as in a tissue culture dish or in a medical tube or bag (e.g., during apheresis). In other examples, a subject is irradiated in vivo, for example irradiating a subject who has previously been administered IR700-molecule conjugates. In some examples, a portion of the subject is irradiated, for example an organ or other area where the target is suspected to be (e.g., in the liver, heart, brain, or stomach for example) in the subject can be irradiated.

The subject or cells are irradiated with a therapeutic dose of radiation, such as at a wavelength of 660-710 nm, such as 660 nm-700 nm, 680 nm-700 nm, 670 nm-690 nm, for example, 680 nm or 690 nm. In particular examples, the cells or the subject is irradiated at a dose of at least 1 J cm$^{-2}$, at least 4 J cm$^{-2}$, such as at least 10 J cm$^{-2}$, at least 30 J cm$^{-2}$, at least 50 J cm$^{-2}$, at least 100 J cm$^{-2}$, or at least 500 J cm$^{-2}$, for example, 1-1000 J cm$^{-2}$, 1-500 J cm$^{-2}$, 30 to 50 J cm$^2$, 4-8 J cm$^2$, 10-100 J cm$^2$, or 10-50 J cm$^{-2}$.

Cells (or patients) can be irradiated one or more times. Thus, irradiation can be completed in a single day, or may be done repeatedly on multiple days with the same or a different dosage (such as irradiation at least 2 different times, 3 different times, 4 different times 5 different times or 10 different times). Repeated irradiations may be done on the same day, on successive days, or every 1-3 days, every 3-7 days, every 1-2 weeks, every 2-4 weeks, every 1-2 months, or at even longer intervals.

Exemplary Devices Containing NIR LEDs and/or Lasers

Any type of item that can be worn or placed on the body, and is amenable to the incorporation of NIR LEDs and/or a laser systems (e.g., an argon NIR laser), can be used in the methods described herein. In one example, the device is a chamber into which the patient is inserted. Such devices can be used to remove targets present in the body, such as those in the blood or lymph, or on the skin.

To adequately remove a sufficient amount of the target(s) in the body it may be necessary to wear the devices for an extended period of time, such as several weeks or months. Thus, these devices can be incorporated into every day clothing, jewelry and nightwear such as blankets. These devices make it possible to expose the patient to NIR light using portable everyday articles of clothing and jewelry so that treatment remains private and does not interfere with everyday activities. For instance, a necklace incorporating NIR LEDs and/or a laser (e.g., an argon NIR laser) can be customizable to the patient's tastes, and worn discreetly during the day for therapy (for example cleaving IR700-molecule conjugates that pass through the carotid artery and other vasculature in the neck). Multiple devices of a similar "everyday" nature (blankets, bracelets, necklaces, underwear, socks, shoe inserts and the like) could be worn by the same patient during the treatment period. For example while sleeping, a patient could use the NIR blanket. The devices can also include a power supply, such as a battery, and a cooling element to prevent overheating for such devices as blankets.

In one example, the device is jewelry, such as a ring, watch, bracelet, or necklace. In another example, the item is an article of clothing or accessory, such as a shirt, belt, pants, underwear, socks, coat, shoe insert, scarf, hat, wrist guard, gloves, and the like. In another example, the device is an article that can cover the body, such as a blanket or towel. In another example, the device is a whole body light chamber that exposes the skin directly (such a device could also include a power supply and/or cooling supply).

By wearing the device that incorporates one or more NIR LEDs (such as at least 2, at least 3, at least 4, at least 5, at least 10, at least 20, or at least 50 NIR LEDs) and/or a laser (e.g., an argon NIR laser), targets are present in the body (e.g., blood, lymph, or skin) become exposed to the light generated by the NIR LEDs or laser (such as an NIR LED or laser that emits at 660 to 710 nm, such as 670 to 710 nm or 680 to 700 nm). The light emitted from the NIR LED and/or a laser (e.g., an argon NIR laser) can penetrate the skin and blood vessels (such as the carotid artery or microvasculature in the skin), thus allowing the light to activate the IR700-molecule conjugate (which may include the target or be bound to the target), thus cleaving the IR700 and causing it (and any molecule bound thereto) to aggregate. The NIR LEDs and/or a laser (e.g., an argon NIR laser) can be arranged in the device to ensure that the skin or the blood vessels or lymphatic system are targeted.

NIR LED and/or and laser (e.g., an argon NIR laser) devices that can be used in the methods provided herein are commercially available. The applicable products from one manufacturer, Marubeni America, are listed below. The first product, a molded LED, has low power but it could be used over a longer exposure time. The other options have higher power and thus may benefit from provisions for additional cooling. Except for the last one, which is packaged in a 25 mm×18 mm metal case, the others are applicable to wearable devices such as bracelets, necklace, underwear, socks, gloves, hats and other wearable items. All are usable in blankets, handheld devices or chambers.

For example, Marubeni America Corporation (tech-led.com/index.shtml) provides the following NIR LEDs with lens options to set the irradiation pattern: Molded LED (www.tech-led.com/data/L680-AU.pdf) which is 5 mm in diameter, has a total radiated power of 4 mW, calculated power density of 5 mW cm$^2$ and a power requirement of 1.8V 20 mA; Surface Mount LED which is 3.5 mm×2.7 mm, has a total radiated power of 3 mW, calculated power density of 32 mW cm$^{-2}$, and a power requirement of 1.9V 50 mA; Super Beam (tech-led.com/Superbeam_LEDs.shtml) which is 7.6 mm×7.6 mm, has a total radiated power of 20-52 mW, calculated power density of 34-90 mW cm$^{-2}$, and a power requirement of 1.65V 100 mA; High Power Surface Mount (tech-led.com/SMB_BL_LEDs.shtml) which is 5 mm×5 mm or 7 mm diameter, has a total radiated power of 90 mW, calculated power density of 360 mW cm$^{-2}$ and a power requirement of 2.4V 500 mA; and High Power Illuminators (tech-led.com/High_Power_Illuminators.shtml) which is 25 mm×18 mm, has a total radiated power of 150 mW, a calculated power density of 33 mW cm$^{-2}$ and a power requirement of 10V 120 mA. Alternatively, such devices can be made that emit light at 690 nm with a similar power with short strong intermittent pulse.

During in vitro experimentation, NIR light with a power density of 2.2 mW cm$^2$ (or 2.2 mJ s$^{-1}$ cm$^{-2}$) induced cell death. Assuming an attenuation coefficient for tissue of 4 cm$^{-1}$, the intensity of the light would be down to 10% at 5.8 mm and 1% at 12 mm. This indicates that for in vivo applications, the power density required needs to be 10-100 times larger. That is, the dose of light emitted by the NIR LED device in some examples is at least 20 mW cm$^{-2}$, such as at least 50 mW cm$^{-2}$, at least 100 mW cm$^{-2}$, at least 150 mW cm$^{-2}$, at least 200 mW cm$^2$ or, at least 300 mW cm$^2$. Multiple NIR LEDs can be arranged in a two-dimensional array to cover larger areas. In one example, a laser is used as the NIR light source as an alternative to an LED.

The NIR LEDs and/or a laser (e.g., an argon NIR laser) can be powered by using a power supply (which may be directly or indirectly part of the device). The power supply requirement would depend on the number of LEDs and lasers in the device. For example, one or more batteries can be used to power the NIR LED. For some LEDs, 4 AA batteries can power 3 LEDs in series. An alkaline AA battery is rated at a maximum of 3000 mAh so this configuration provide powers for up to 150, 60, and 30 hr at 20, 50 and 100 mA.

In some examples, the device further includes a cooling device (which may be directly or indirectly part of the device). For example, heat sinks can be used for passive or active cooling. Another alternative is a thermoelectric effect (Peltier). This would draw additional power but it can be used in applications where the power requirements would need a plug-in AC adapter.

Another type of device that can be used with the disclosed methods is a flashlight-like device with NIR LEDs and/or a laser (e.g., an argon NIR laser). Such a device can be used for focal therapy during surgery, or incorporated into endoscopes to apply NIR light to body surfaces after the administration of the IR700-molecule conjugate. Such devices can be used by physicians or qualified health personnel to direct treatment to particular targets on the body.

Treatment Using Wearable NIR LEDs

As described herein, the disclosed methods can be used to remove targets in vivo. In some examples, in order to remove targets circulating in the body or present on the skin, the patient can wear a device that incorporates an NIR LED. In some examples the patient uses at least two devices, for example an article of clothing or jewelry during the day, and a blanket at night. In some example the patient uses at least two devices at the same time, for example two articles of clothing. These devices make it possible to expose the patient to NIR light using portable everyday articles of clothing and jewelry so that treatment remains private and does not interfere with everyday activities. In some examples, the device can be worn discreetly during the day for PIT therapy.

In one example, the patient is administered one or more IR700-molecule conjugates (e.g., one or more doses) using the methods described herein. The patient then wears a device that incorporates an NIR LED, permitting long-term therapy and removal of targets present in the blood or lymph or on the skin. In some examples, the dose is at least at least 1 J cm$^{-2}$, at least 10 J cm$^{-2}$, at least 20 J cm$^{-2}$, or at least 30 J cm$^{-2}$, such as 20 J cm$^{-2}$ or 30 J/cm$^{2}$. In some examples, administration of the IR700-molecule conjugates is repeated over a period of time (such as twice weekly, every other day, every other week, twice monthly, monthly or every other month), to ensure therapeutic/effective levels are present in the body.

In some examples, the patient wears or uses the device, or combination of devices, for at least 1 week, such as at least 2 weeks, at least 4 weeks, at least 8 weeks, at least 12 weeks, at least 4 months, at least 6 months, or even at least 1 year. In some examples, the patient wears or uses the device, or combination of devices, for at least 4 hours a day, such as at least 12 hours a day, at least 16 hours a day, at least 18 hours a day, or 24 hours a day. It is possible that multiple devices of a similar "everyday" nature (blankets, bracelets, necklaces, underwear, socks, shoe inserts) could be worn by the same patient during the treatment period. At night the patient can use the NIR LED blanket or other covering.

Exemplary Targets

The disclosed methods can be designed to remove or isolate any target agent of interest in vitro, ex vivo, or in vivo. Thus, the methods and IR700-molecule conjugates provided herein can be used to remove or isolate any target agent of interest, such as the specific examples provided herein. Exemplary target agents are provided below; however one skilled in the art will appreciate that other target agents can be removed with the disclosed methods and IR700-molecule conjugates. As described herein, selecting an appropriate specific binding agent that binds or hybridizes to the target agent, allows one to develop an IR700-specific binding agent conjugate to remove, separate, or isolate a particular target agent.

Metals

In one example the target agent is a metal (e.g., elements, compounds, or alloys that have high electrical conductivity), such as a heavy metal or a nutritional metal. Thus, the disclosed methods and IR700-molecule conjugates permit removal of metals in vivo, ex vivo, or in vitro. Metals occupy the bulk of the periodic table, while non-metallic elements can only be found on the right-hand-side of the Periodic Table of the Elements. A diagonal line drawn from boron (B) to polonium (Po) separates the metals from the nonmetals. Most elements on this line are metalloids, sometimes called semiconductors. Elements to the lower left of this division line are called metals, while elements to the upper right of the division line are called non-metals.

Target heavy metals include any metallic chemical element that has a relatively high density and is toxic, highly toxic or poisonous at low concentrations. Examples of target heavy metals include mercury (Hg), cadmium (Cd), arsenic (As), chromium (Cr), thallium (Tl), uranium (U), plutonium (Pu), and lead (Pb).

Target nutritional metal ions include those important in animal nutrition and may be necessary for particular biological functions, include calcium, iron, cobalt, magnesium, manganese, molybdenum, zinc, cadmium, sodium, potassium, lithium, and copper.

Antibodies specific for particular metals are known in the art, and such can be conjugated to IR700 and used for the methods provided herein. For example, Zhu et al. describe mAbs specific for chelated cadmium ions (*J. Agric. Food Chem.* 55:7648-53, 2007), Wylie et al. describe mAbs specific for mercuric ions (*PNAS* 89:4104-8, 1992), and Love et al. describe mAbs specific for inidium (*Biochem.* 32:10950-9, 1993). In addition, bifunctional derivatives of metal ion chelators (EDTA, DTPA, DOTA) can be covalently conjugated to proteins and loaded with the desired metal ion. These conjugates can be used to prepare hybridoma cell lines which synthesize metal-specific monoclonal antibodies. In addition, aptamers have been developed to recognize metal ions such as Zn(II) (Ciesiolka et al., *RNA* 1: 538-550, 1995) and Ni(II) (Hofmann et al., *RNA*, 3:1289-1300, 1997). Furthermore, DNAzymes specific for particular metal ions are known, such as lead, copper, uranium, zinc, mercury, cadmium and magnesium. Such molecules can be used to generate an IR700-molecule conjugate to remove a target metal.

Pathogens/Microbes

Any pathogen or microbe can be removed or isolated using the methods and IR700-molecule conjugates provided herein. In some examples, a particular microbial cell or organism is removed, a particular spore, or a particular virus. Exemplary target pathogens include, but are not limited to, viruses, bacteria, fungi, nematodes, and protozoa. A non-limiting list of pathogens that can be removed or isolated using the methods provided herein are provided below.

For example, target viruses include positive-strand RNA viruses and negative-strand RNA viruses. Exemplary target positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); Calciviridae (which includes Norovirus and Sapovirus); and Coronaviruses (examples of which include SARS coronaviruses, such as the Urbani strain). Exemplary negative-strand RNA viruses include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses).

Viruses also include DNA viruses. Target DNA viruses include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

Another group of viruses includes Retroviruses. Examples of target retroviruses include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

In one example, the virus detected with the disclosed methods or sensors is one or more of the following: HIV-1 (for example an HIV antibody, p24 antigen, or HIV genome); Hepatitis A virus (for example an Hepatitis A antibody, or Hepatitis A viral genome); Hepatitis B (HB) virus (for example an HB core antibody, HB surface antibody, HB surface antigen, or HB viral genome); Hepatitis C (HC) virus (for example an HC antibody, or HC viral genome); Hepatitis D (HD) virus (for example an HD antibody, or HD viral genome); Hepatitis E virus (for example a Hepatitis E antibody, or HE viral genome); a respiratory virus (such as influenza A & B, respiratory syncytial virus, human parainfluenza virus, or human metapneumovirus), or West Nile Virus.

Pathogens also include bacteria. Bacteria can be classified as gram-negative or gram-positive. Exemplary target gram-negative bacteria include, but are not limited to: *Escherichia coli* (e.g., K-12 and O157:H7), *Shigella dysenteriae*, and *Vibrio cholerae*. Exemplary target gram-positive bacteria include, but are not limited to: *Bacillus anthracis, Staphylococcus aureus, Listeria*, pneumococcus, gonococcus, and streptococcal meningitis. In one example, the bacteria removed with the disclosed methods and IR700-molecule conjugates is one or more of the following: Group A *Streptococcus*; Group B *Streptococcus; Helicobacter pylori*; Methicillin-resistant *Staphylococcus aureus*; vancomycin-resistant enterococci; *Clostridium difficile; E. coli* (e.g., Shiga toxin producing strains); *Listeria; Salmonella; Campylobacter; B. anthracis* (such as spores); *Chlamydia trachomatis*; Ebola, and *Neisseria gonorrhoeae*.

Protozoa, nemotodes, and fungi are also types of pathogens. Exemplary target protozoa include, but are not limited to, *Plasmodium* (e.g., *Plasmodium falciparum*: to diagnose malaria), *Leishmania, Acanthamoeba, Giardia, Entamoeba, Cryptosporidium, Isospora, Balantidium, Trichomonas, Trypanosoma* (e.g., *Trypanosoma brucei*), *Naegleria*, and *Toxoplasma*. Exemplary target fungi include, but are not limited to, *Coccidiodes immitis* and *Blastomyces dermatitidis*.

In one example, bacterial spores are removed. For example, the genus of *Bacillus* and *Clostridium* bacteria produce spores that can be detected. Thus, *C. botulinum, C. perfringens, B. cereus*, and *B. anthracis* spores can be detected (for example detecting anthrax spores). One will also recognize that spores from green plants can also be removed using the methods and IR700-molecule conjugates provided herein.

In some examples, intact microbes are removed, for example by binding to a target surface protein (such as a receptor) on the microbe using IR700-molecule conjugates that include, for example, antibodies, DNAzymes, or DNA aptamers specific for the target protein. For example, antibodies that can be used with the disclosed methods and IR700-molecule conjugates are available from commercial sources, such as Novus Biologicals (Littleton, CO) and ProSci Incorporated (Poway, CA) provide *E. coli*-specific antibodies; KPL (Gaithersburg, MD) provides *Listeria*-specific antibodies; Thermo Scientific/Pierce Antibodies (Rockford, IL) provides antibodies specific for several microbes, including bacteria and viruses, such as influenza A, HIV-1, HSV 1 and 2, *E. coli, Staphylococcus aureus, Bacillus anthracis* and spores thereof, *Plasmodium*, and *Cryptosporidium*. In addition, aptamers specific for microbial proteins can be used with the disclosed methods and IR700-molecule conjugates, such as those specific for HIV reverse transcriptase (Chaloin et al., *Nucleic Acids Research*, 30:4001-8, 2002) and hepatitis C virus RNA-dependent RNA polymerase (Biroccio et al., *J. Virol.* 76:3688-96, 2002); toxins such as cholera whole toxin and staphylococcal enterotoxin B (Bruno and Kiel, *BioTechniques*, 32: pp. 178-180 and 182-183, 2002); and bacterial spores such as anthrax (Bruno and Kiel, *Biosensors & Bioelectronics*, 14:457-464, 1999). In addition, DNAzymes specific for microbial proteins can be used with the disclosed methods and IR700-molecule conjugates, such as those specific for *Escherichia coli*-K12 (Ali et al., *Angewandte Chemie International Edition.* 50, 3751-4, 2011*; Li, Future Microbiol.* 6, 973-976, 2011; and Aguirre, et al., J. Visualized Experiments. 63, 3961, 2012). Such molecules can be used to generate an IR700-molecule conjugate to remove a target pathogen or spore.

Proteins/Peptides

The disclosed methods and IR700-molecule conjugates also permit removal or isolation of a variety of proteins and peptides, such as cell surface receptors, cytokines, antibodies, hormones, lectins, as well as toxins and venoms. In some examples, a target protein is selected that is associated with a disease or condition, such that removal or reduction of the target protein can be used to treat the disease or condition. In particular examples, the IR700-molecule conjugate can specifically bind to a protein or peptide target (such as an IR700-molecule conjugate that includes an antibody, functional antibody fragment, Affibody® molecule, nucleic acid molecule, hapten, or functional nucleic acid specific for the protein). For example, specific binding agents for particular proteins are known in the art. For example, such antibodies are available from commercial sources, such as Invitrogen, Santa Cruz Biotechnology (Santa Cruz, CA); ABCam (Cambridge, MA) and IBL International (Hamburg, Germany). Such molecules can be used to generate an IR700-molecule conjugate to remove a target protein.

In some examples where the target molecule is a protein, the sample to be tested can be treated with agents that permit disruption of cells or pathogens. The proteins can be extracted or isolated, and then exposed to an IR700-molecule conjugate disclosed herein, such as an IR700-molecule conjugate specific for the target protein, to permit isolation or removal of the target protein from the mixture of proteins.

In one example the target protein is a cytokine. Cytokines are small proteins secreted by immune cells that have effects on other cells. Examples of target cytokines include interleukins (IL) and interferons (IFN), and chemokines, such as IL-1, IL-2, IL-4, IL-6, IL-8, IL-10, IFN-γ, IFN-β, transforming growth factor (TGF-β), and tumor necrosis factor (TNF)-α.

In one example the target protein is a hormone. A hormone is a chemical messenger that transports a signal from one cell to another. Examples of target hormones include plant and animal hormones, such as endocrine hormones or exocrine hormones. Particular examples include follicle stimulating hormone (FSH), human chorionic gonadotropin (hCG), thyroid stimulating hormone (TSH), growth hormone, progesterone, and the like.

In one example the target protein is a toxin. Toxins are poisonous substances produced by cells or organisms, such as plants, animals, microorganisms (including, but not limited to, bacteria, viruses, fungi, rickettsiae or protozoa). Particular examples of target toxins include botulinum toxin, ricin, diphtheria toxin, Shiga toxin, Cholera toxin, Staphylococcal enterotoxin B, and anthrax toxin. In another example, the toxin is an environmental toxin. In one example the toxin is a mycotoxin, such as: aflatoxin, citrinin, ergot alkaloids, patulin, fusarium toxins, or ochratoxin A. In one example the target toxin is a cyanotoxin, such as: microcystins, nodularins, anatoxin-a, aplysiatoxins, cylindrospermopsins, lyngbyatoxin-a, and saxitoxins. In one example the target toxin is an endotoxin, hemotoxin, cardiotoxin, neurotoxin, necrotoxin, neurotoxin, or cytotoxin.

In one example the target protein is a venom (or a component in venom, such as a toxin), such as one produced by a wasp, ant, spider, scorpion, fish, snake, and the like. Examples include wasp venom proteins phospholipase A1 and B, neurotoxins, snake venom proteins such as metalloproteinase, phosphodiesterase, phospholipase A2, oxidase, protease, and hyaluronidase, and scorpion venom protein chlorotoxin.

In one example the target protein is a lectin. Lectins are proteins that recognize and bind to specific carbohydrates on the surfaces of cells. A lectin usually contains two or more binding sites for carbohydrate units. In animals, lectins regulate the cell adhesion to glycoprotein synthesis, control protein levels in blood, and bind soluble extracellular and intracellular glycoproteins. Also, in the immune system, lectins recognize carbohydrates found specifically on pathogens, or those that are not recognizable on host cells. Clinically, purified lectins can be used to identify glycolipids and glycoproteins on an individual's red blood cells for blood typing. Exemplary lectins include but are not limited to: concanavalin A, lentil lectin, snowdrop lectin (all which bind mannose); ricin, peanut agglutinin, jacalin, and hairy vetch lectin (all which bind galactose); wheat germ agglutinin (which binds N-acetylglucosamine); elderberry lectin, *Maackia amurensis* hemoagglutinin (all which bind N-acetylneuraminic acid); and *Ulex europaeus* agglutinin and *Aleuria aurantia* lectin (all which bind fucose).

In one example, the target protein is a tumor-associated or tumor-specific antigen, such as CA-125 (ovarian cancer marker), alphafetoprotein (AFP, liver cancer marker); carcinoembryonic antigen (CEA; bowel cancers), BRCA1 and 2 (breast cancer), and the like. Such proteins are useful for removing tumor cells.

In one example the target protein is a fertility-related biomarker, such as hCG, luteinizing hormone (LH), follicle-stimulating hormone (FSH), or fetal fibrinogen.

In one example the target protein is a diagnostic protein, such as prostate-specific antigen (PSA, for example GenBank® Accession No. NP_001025218), C reactive protein, cyclic citrullinate peptides (CCP, for example to diagnose rheumatoid arthritis) or glycated hemoglobin (Hb A1c). In another example, the protein is one found on the surface of a target microbe or cell, such as a bacterial cell, virus, spore, or tumor cell. Such proteins, such as receptors, may be specific for the microbe or cell (for example HER2, IGFIR, EGFR or other tumor-specific receptor noted below in "nucleic acids"). In one example the protein is prostate-specific antigen (PSA, for example GenBank® Accession No. NP_001025218), which can be targeted using an antibody or PSA-specific aptamer (e.g., see Savory et al., *Biosensors & Bioelectronics* 15:1386-91, 2010 and Jeong et al., *Biotechnology Letters* 32:378-85, 2010).

Nucleic Acid Molecules

The disclosed methods also permit removal or isolation of target nucleic acid molecules, such DNA or RNA (such as cDNA, genomic DNA, mRNA, miRNA, etc.), such as a DNA or RNA sequence that is specific for a particular pathogen or cell of interest. For example, pathogens can have conserved DNA or RNA sequences specific to that pathogen (for example conserved sequences are known in the art for HIV, bird flu and swine flu), and cells may have specific DNA or RNA sequences unique to that cell. In some examples, a target nucleic acid molecule is selected that is associated with a disease or condition, such that removal or reduction of the target nucleic acid molecule can be used to treat the disease or condition (for example to downregulate expression. In one example, the target nucleic acid molecule is one that dominates a sample, and thus can be removed from a sample to permit analysis (e.g., identification or cloning) of rarer nucleic acid molecules in the sample (such as a nucleic acid molecule from a rare organism in the sample).

In particular examples, the IR700-molecule conjugate can specifically bind to a nucleic acid molecule target (such as an IR700-molecule conjugate that includes a protein or nucleic acid molecule specific for the target nucleic acid molecule). For example, specific binding agents for particular nucleic acid molecules are known in the art, and can be designed using routine methods. For example a nucleic acid molecule having sufficient complementarity to hybridize to a target nucleic acid molecule (such as one having at least 80%, at least 90%, at least 95% or at least 99% sequence complementarity to the target) can be generated and conjugated to IR700. Such molecules can be used to generate an IR700-molecule conjugate to remove a target nucleic acid molecule.

In some examples where the target molecule is a nucleic acid molecule, the sample to be tested can be treated with agents that permit disruption of cells or pathogens. The nucleic acid molecules can be extracted or isolated, and then exposed to an IR700-molecule conjugate disclosed herein, such as a an IR700-molecule conjugate specific for the target nucleic acid molecule, to permit isolation or removal of the target nucleic acid molecule from the mixture of nucleic acid molecules.

In specific non-limiting examples, the target nucleic acid sequence is associated with a tumor (for example, a cancer). Numerous chromosome abnormalities (including translocations and other rearrangements, reduplication (amplification) or deletion) have been identified in neoplastic cells, especially in cancer cells, such as B cell and T cell leukemias, lymphomas, breast cancer, ovarian cancer, colon cancer, neurological cancers and the like.

Exemplary target nucleic acids include, but are not limited to: the SYT gene located in the breakpoint region of chromosome 18q11.2 (common among synovial sarcoma soft tissue tumors); HER2, also known as c-erbB2 or HER2/neu (a representative human HER2 genomic sequence is provided at GENBANK® Accession No. NC_000017, nucleotides 35097919-35138441) (HER2 is amplified in human breast, ovarian, gastric, and other cancers); p16 (including D9S1749, D9S1747, p16(INK4A), p14(ARF), D9S1748, p15(INK4B), and D9S1752) (deleted in certain bladder cancers); EGFR (7p12; e.g., GENBANK® Accession No. NC_000007, nucleotides 55054219-55242525), MET (7931; e.g., GENBANK® Accession No. NC_000007, nucleotides 116099695-116225676), C-MYC (8924.21; e.g., GENBANK® Accession No. NC_000008, nucleotides 128817498-128822856), IGFIR (15q26.3; e.g., GENBANK® Accession No. NC_000015, nucleotides 97010284-97325282), D5S271 (5p15.2), KRAS (12p12.1; e.g. GENBANK® Accession No. NC_000012, complement, nucleotides 25249447-25295121), TYMS (18p11.32; e.g., GENBANK™ Accession No. NC_000018, nucleotides 647651-663492), CDK4 (12q14; e.g., GENBANK® Accession No. NC 000012, nucleotides 58142003-58146164, complement), CCND1 (11q13, GENBANK® Accession No. NC_000011, nucleotides 69455873-69469242), MYB (6q22-q23, GENBANK® Accession No. NC_000006, nucleotides 135502453-135540311), lipoprotein lipase (LPL) (8p22; e.g., GENBANK® Accession No. NC_000008, nucleotides 19840862-19869050), RBI (13q14; e.g., GENBANK® Accession No. NC 000013, nucleotides 47775884-47954027), p53 (17p113.1; e.g., GENBANK® Accession No. NC_000017, complement, nucleotides 7512445-7531642), N-MYC (2p24; e.g., GENBANK® Accession No. NC_000002, complement, nucleotides 15998134-16004580), CHOP (12q13; e.g., GENBANK® Accession No. NC_000012, complement, nucleotides 56196638-56200567), FUS (16p11.2; e.g., GENBANK® Accession No. NC_000016, nucleotides 31098954-31110601), FKHR (13p14; e.g., GENBANK® Accession No. NC_000013, complement, nucleotides 40027817-40138734), aALK (2p23; e.g., GENBANK® Accession No. NC_000002, complement, nucleotides 29269144-29997936), Ig heavy chain, CCND1 (11q13; e.g., GENBANK® Accession No. NC_000011, nucleotides 69165054-69178423), BCL2 (18q21.3; e.g., GENBANK® Accession No. NC_000018, complement, nucleotides 58941559-59137593), BCL6 (3q27; e.g., GENBANK® Accession No. NC_000003, complement, nucleotides 188921859-188946169), AP1 (1p32-p31; e.g., GENBANK® Accession No. NC_000001, complement, nucleotides 59019051-59022373), TOP2A (17q21-q22; e.g., GENBANK® Accession No. NC_000017, complement, nucleotides 35798321-35827695), TMPRSS (21q22.3; e.g., GENBANK® Accession No. NC_000021, complement, nucleotides 41758351-41801948), ERG (21922.3; e.g., GENBANK® Accession No. NC_000021, complement, nucleotides 38675671-38955488); ETV1 (7p21.3; e.g., GENBANK® Accession No. NC_000007, complement, nucleotides 13897379-13995289), EWS (22q12.2; e.g., GENBANK™ Accession No. NC_000022, nucleotides 27994017-28026515); FLI1 (11q24.1-q24.3; e.g., GENBANK® Accession No. NC_000011, nucleotides 128069199-128187521), PAX3 (2q35-q37; e.g., GENBANK® Accession No. NC_000002, complement, nucleotides 222772851-222871944), PAX7 (1p36.2-p36.12; e.g., GENBANK® Accession No. NC_000001, nucleotides 18830087-18935219), PTEN (10q23.3; e.g., GENBANK® Accession No. NC_000010, nucleotides 89613175-89718512), AKT2 (19q13.1-q13.2; e.g., GENBANK® Accession No. NC_000019, complement, nucleotides 45428064-45483105), MYCL1 (1p34.2; e.g., GENBANK™ Accession No. NC_000001, complement, nucleotides 40133685-40140274), REL (2p13-p12; e.g., GENBANK® Accession No. NC_000002, nucleotides 60962256-61003682) and CSF1R (5q33-q35; e.g., GENBANK® Accession No. NC_000005, complement, nucleotides 149413051-149473128).

Carbohydrates

The disclosed methods and IR700-molecule conjugates also permit removal of a variety of carbohydrates (e.g., saccharide). Examples include monosaccharides and disaccharides. In particular examples, the specific binding agent that specifically binds to the carbohydrate target is a lectin. For example, concanavalin A, lentil lectin, and snowdrop lectin can be used to remove mannose; ricin, peanut agglutinin, jacalin, and hairy vetch lectin can be used to remove galactose; wheat germ agglutinin can be used to remove N-acetylglucosamine; elderberry lectin and *Maackia amurensis* hemoagglutinin can be used to remove N-acetyl-neuraminic acid); and *Ulex europaeus* agglutinin and *Aleuria aurantia* lectin can be used to remove fucose. Such molecules can be used to generate an IR700-molecule conjugate to remove a target carbohydrate.

Recreational Drugs

The disclosed methods and IR700-molecule conjugates also permit removal of a variety of recreational drugs. For example, such drugs can be removed from a subject who has overdosed on such drugs. Antibodies specific for particular drugs are known in the art. For example, antibodies to tetrahydrocannabinol, heroin, cocaine, caffeine, and methamphetamine are available from AbCam (Cambridge, MA). In particular examples, the specific binding agent that specifically binds to the drug target is a nucleic acid (such as a functional nucleic acid, such as an aptamer or DNAzyme). Such molecules can be used to generate an IR700-molecule conjugate to remove a target recreational drug.

For example, caffeine, cocaine, opiates and opioids (such as oxycodone), cannabis (for example by detecting tetrahydrocannabinol (THC)), heroin, methamphetamines, crack, ethanol, acetaminophen, benzodiazepines, methadone, phencyclidine, or tobacco (for example by detecting nicotine), can be removed or isolated using the disclosed methods and IR700-molecule conjugates.

Cells

Any target cell can be removed or isolated in vivo, in vitro, or ex vivo with the disclosed methods and IR700-molecule conjugates. The target cell to be removed or isolated from the subject can be a cell that is not desired or whose growth is not desired (e.g., tumor cell, cancer stem cell, diseased cell, or cell that causes or exacerbates a disease or disorder in a subject), or can be a cell that is desired, such as a PBMC or HSC. In some examples, cells are removed or isolated by using a specific binding agent that recognizes a surface protein, such as a receptor on the surface of the cell. For example, the target cell may express a cell surface protein that is not substantially found on the surface of other non-target cells, a specific binding agent can be selected that specifically recognizes such protein, and an IR700-molecule conjugate generated for that protein. For example, antibodies and functional nucleic acid molecules specific for particular cells and cell surface proteins are known in the art, and are available from commercial sources, such as AbCam and Santa Cruz Biotechnology.

In one example, the cell to be removed is a tumor cell, which can be either malignant or benign, solid or liquid (for example, hematogenous). In one example, the target cell is an undesired cell to be removed from a subject, such as a cancer cell in a patient with cancer. Exemplary cells that can be removed with the disclosed methods include cells of the following tumors: a liquid tumor such as a leukemia, including acute leukemia (such as acute lymphocytic leukemia, acute myelocytic leukemia, acute myelogenous leukemia, myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate-, and high-grade), multiple myeloma, Waldenstrdm's macroglobulinemia, heavy chain disease, myelodysplastic syndrome, mantle cell lymphoma and myelodysplasia. In another example the cell removed is from a solid tumor, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Thus, in some examples, cell surface protein is a tumor-specific protein (also known in the art as a tumor-specific antigen), and the IR700-molecule conjugate is an IR700-tumor specific protein binding agent conjugate. Examples of tumor-specific antigens include but are not limited to, members of the EGF receptor family (e.g., HER1, 2, 3, and 4) and cytokine receptors (e.g., CD20, CD25, IL-13R, CD5, CD52, etc.). For example HER2 is primarily found in breast cancers, while HER1 is primarily found in adenocarcinomas, which can be found in many organs, such as the pancreas, breast, prostate and colon. Exemplary tumor-specific proteins that can be found on a target cell (and to which a specific binding agent for that protein can be used to formulate an IR700-tumor specific protein binding agent conjugate), include but are not limited to: any of the various MAGEs (Melanoma-Associated Antigen E), including MAGE 1 (e.g., GenBank Accession Nos. M77481 and AAA03229), MAGE 2 (e.g., GenBank Accession Nos. L18920 and AAA17729), MAGE 3 (e.g., GenBank Accession Nos. U03735 and AAA17446), MAGE 4 (e.g., GenBank Accession Nos. D32075 and A06841.1), etc.; any of the various tyrosinases (e.g., GenBank Accession Nos. U01873 and AAB60319); mutant ras; mutant p53 (e.g., GenBank Accession Nos. X54156, CAA38095 and AA494311); p97 melanoma antigen (e.g., GenBank Accession Nos. M12154 and AAA59992); human milk fat globule (HMFG) associated with breast tumors (e.g., GenBank Accession Nos. S56151 and AAB19771); any of the various BAGEs (Human B melanoma-Associated Antigen E), including BAGE1 (e.g., GenBank Accession No. Q13072) and BAGE2 (e.g., GenBank Accession Nos. NM_182482 and NP_872288), any of the various GAGEs (G antigen), including GAGE1 (e.g., GenBank Accession No. Q13065) or any of GAGE2-6; various gangliosides, and CD25 (e.g., GenBank Accession Nos. NP_000408.1 and NM_000417.2). Other tumor-specific antigens include the HPV 16/18 and E6/E7 antigens associated with cervical cancers (e.g., GenBank Accession Nos. NC_001526, FJ952142.1, ADB94605, ADB94606, and U89349), mucin (MUC 1)-KLH antigen associated with breast carcinoma (e.g., GenBank Accession Nos. J03651 and AAA35756), CEA (carcinoembryonic antigen) associated with colorectal cancer (e.g., GenBank Accession Nos. X98311 and CAA66955), gp100 (e.g., GenBank Accession Nos. S73003 and AAC60634) associated with for example melanoma, MART1 antigens associated with melanoma (e.g., GenBank Accession No. NP_005502), cancer antigen 125 (CA125, also known as mucin 16 or MUC16) associated with ovarian and other cancers (e.g., GenBank Accession Nos. NM_024690 and NP_078966); alpha-fetoprotein (AFP) associated with liver cancer (e.g., GenBank Accession Nos. NM_001134 and NP_001125); Lewis Y antigen associated with colorectal, biliary, breast, small-cell lung, and other cancers; tumor-associated glycoprotein 72 (TAG72) associated with adenocarcinomas; and the PSA antigen associated with prostate cancer (e.g., GenBank Accession Nos. X14810 and CAA32915). Other exemplary tumor-specific proteins further include, but are not limited to, PMSA (prostate membrane specific antigen; e.g., GenBank Accession Nos. AAA60209 and AAB81971.1) associated with solid tumor neovasculature, as well prostate cancer; HER-2 (human epidermal growth factor receptor 2, e.g., GenBank Accession Nos. M16789.1, M16790.1, M16791.1, M16792.1 and AAA58637) associated with breast cancer, ovarian cancer, stomach cancer and uterine cancer, HER-1 (e.g., GenBank Accession Nos. NM_005228 and NP_005219) associated with lung cancer, anal cancer, and gliobastoma as well as adenocarcinomas; NY-ESO-1 (e.g. GenBank Accession Nos. U87459 and AA1349693) associated with melanoma, sarcomas, testicular carcinomas, and other cancers, hTERT (aka telomerase) (e.g., GenBank Accession. Nos. NM_198253 and NP_937983 (variant 1), NM_198255 and NP_937986 (variant 2)); proteinase 3 (e.g., GenBank Accession Nos. M29142, M75154, M96839, X55668, NM 00277, M96628, X56606, CAA39943 and AAA36342), and Wilms tumor 1 (WT-1, e.g. GenBank Accession Nos. NM_000378 and NP_000369 (variant A), NM_024424 and NP_077742 (variant B), NM_024425 and NP_077743 (variant C), and NM_024426 and NP_077744 (variant D)). In one example the tumor-specific protein is CD52 (e.g., GenBank Accession. Nos. AAH27495.1 and CAI15846.1) associated with chronic lymphocytic leukemia; CD33 (e.g., GenBank Accession. Nos. NM 023068 and CAD36509.1) associated with acute myelogenous leukemia; and CD20 (e.g., GenBank Accession. Nos. NP_068769 NP_031667) associated with Non-Hodgkin lymphoma.

In some examples the cell removed or isolated is one that negatively impacts an autoimmune disease, such as cell that expresses CD4, CD25, a T cell, and the like.

In some examples the cell removed or isolated is one that is desired, such as a cell in the blood or bone marrow. In one example, the cell removed or isolated is a peripheral blood mononuclear cell (PBMC). For example, IR700-CD19 specific binding agent can be used to isolate or remove PBMCs from a sample, such as a blood sample. The IR700-CD19 specific binding agent is incubated with the sample under conditions that allow the IR700-CD19 specific binding agent to bind to PBMCs in the sample, which is then irradiated with NIR light under conditions that allow the resulting IR700-CD19 specific binding agent-PBMC complex to aggregate. The resulting aggregate is collected, thereby isolating the PBMCs. PMBCs isolated from a sample in some examples are administered to a subject receiving a transplant.

In one example, the cell removed or isolated is a human stem cell (HSC). HSCs can be removed or isolated from umbilical cord, blood, and/or bone marrow. For example, an IR700-CD34 specific binding agent (such as catalog #ab8158 from abeam, or catalog #sc19587 from Santa Cruz Biotechnlogy) and/or an IR700-CD133 specific binding agent (such as catalog #MBS856765 from MyBioSource.com) can be used to isolate or remove HSCs from a sample, such as a blood sample. The IR700-CD34 specific binding agent and/or IR700-CD133 specific binding agent is incubated with the sample under conditions that allow the IR700-CD34 specific binding agent and/or IR700-CD133 specific binding agent to bind to HSCs in the sample, which is then irradiated with NIR light under conditions that allow the resulting IR700-CD34 specific binding agent-HSC and/ or IR700-CD133 specific binding agent-HSC complex to aggregate. The resulting aggregate is collected, thereby isolating the HSCs. HSCs isolated from a sample in some examples are administered to a subject receiving a transplant. In some examples, prior to removing or isolating HSCs, donor subjects are injected with a cytokine, such as granulocyte colony-stimulating factor (G-CSF), to induce cells to leave the bone marrow and circulate in the blood vessels. For example, the donor can be injected with G-CSF alone or in combination with a CXCR4 inhibitor (e.g., plerixafor) before the cell harvest. In one example, G-CSF (e.g., 10 µg/kg) is administered subcutaneously to donor subjects daily for four days and on the fifth day in addition to G-CSF, a CXCR4 inhibitor (e.g., plerixafor) (e.g., 240 µg/kg) is administered subcutaneously. A mobilized peripheral blood stem cell (PBSC) concentrate can then be collected by leukapheresis on day 5 twelve hours after the administration of plerixafor and 2 hours after the last dose of G-CSF. In another example, G-CSF (e.g., 10 µg/kg) is administered subcutaneously to donor subjects daily for five days and a mobilized PBSC concentrate can then be collected by leukapheresis on day 5. The PBSCs express CD34 and/or CD133. In one example, the method of Bloan et al. is used to obtain PBMCs (*Br. J. Haematol.* 120:801-7, 2003). The resulting PBMC sample can be used to isolate HSCs.

In one example, methods are used that deplete non-HSCs from the sample, thereby permitting enrichment of the HSCs (that is, negative selection). For example, IR700-molecule conjugates (e.g., those that include specific binding agents for CD2, CD3, CD11b, CD14, CD15, CD16, CD19, CD56, CD123, and CD235a (Glycophorin A)) can be used to substantially reduce the number of B cells, T cells, natural killer cells, dendritic cells, monocytes, granulocytes, and/or red blood cells. In one example, IR700-molecule conjugates specific for the undesired cells can be incubated with the sample, allowing the IR700-molecule conjugates to bind to the undesired cells. The sample is then irradiated with NIR light under conditions that allow the resulting IR700-molecule-target cell complex to aggregate. The resulting aggregate is collected, thereby removing undesired cells, and enriching the HSCs.

HSCs isolated from a sample in some examples are administered to a subject receiving a transplant. In some examples, the HSCs are obtained from the same subject to be treated (autologous, the donor and recipient are the same person). In other examples, the HSCs are obtained from a subject different from the one to be treated (allogeneic, the donor and recipient are different individuals, or syngeneic, the donor and recipient are identical twins).

In one example, methods are used that deplete CD25-expressing cells from the sample, for example to remove cells associated with transplant rejection. Thus, the sample can be obtained from a subject receiving a transplant, or donating an organ for transplant. For example, IR700-CD25 specific binding agent conjugates can be used to substantially reduce the number of CD25-expressing cells in a sample, such as using Basiliximab or Daclizumab which target the IL-2Ra receptor (CD25). In one example, IR700-CD25 specific binding agent conjugates can be incubated with the sample, allowing the IR700-CD25 specific binding agent conjugates to bind to the undesired cells. The sample is then irradiated with NIR light under conditions that allow the resulting IR700-CD25 specific binding agent —CD25 cell complex to aggregate. The resulting aggregate is collected, thereby removing undesired cells.

In one example, cancer stem cells (CSC) are removed (and in some examples killed) from a subject, such as a subject with cancer. In one example, the CSC is a bladder CSC and the specific binding agent of the IR700-molecule recognizes one or more of (or more than one IR700-molecule conjugate is used): aldehyde dehydrogenase 1-A1/ALDH1A1; CD47; CD44 and CEACAM-6/CD66c. In one example, the CSC is a breast CSC and the specific binding agent of the IR700-molecule recognizes one or more of (or more than one IR700-molecule conjugate is used): aldehyde dehydrogenase 1-A1/ALDH1A1, GLI-1, BMI-1, GLI-2, CD24, IL-1 alpha/IL-1F1, CD44, IL-6 R alpha, connexin 43/GJA1, CXCR1/IL-8 RA, CXCR4, Integrin alpha 6/CD49f, DLL4, PON1, EpCAM/TROP1, PTEN, and ErbB2/Her2. In one example, the CSC is a colon CSC and the specific binding agent of the IR700-molecule recognizes one or more of (or more than one IR700-molecule conjugate is used): ALCAM/CD166, EpCAM/TROP1, aldehyde dehydrogenase 1-A1/ALDH1A1, GLI-1, CD44, Lgr5/GPR49, DPPIV/CD26, and Musashi-L. In one example, the CSC is a gastric CSC and the specific binding agent of the IR700-molecule recognizes one or more of (or more than one IR700-molecule conjugate is used): CD44, Lgr5/GPR49, and DLL4. In one example, the CSC is a glioma/medulloblastoma CSC and the specific binding agent of the IR700-molecule recognizes one or more of (or more than one IR700-molecule conjugate is used): A20/TNFAIP3, IL-6 R alpha, ABCG2, Integrin alpha 6/CD49f, Aldehyde Dehydrogenase 1-A1/ALDH1A1, L1CAM, BMI-1, c-Maf, CD15/Lewis X, Musashi-1, CD44, c-Myc, CX3CL1/Fractalkine, Nestin, CX3CR1, Podoplanin, CXCR4, SOX2, and HIF-2 alpha/EPAS1. In one example, the CSC is a head and neck CSC and the specific binding agent of the IR700-molecule recognizes one or more of (or more than one IR700-molecule conjugate is used): ABCG2, CD44, aldehyde dehydrogenase 1-A I/ALDH1A1, HGF R/c-MET, BMI-1, and Lgr5/GPR49. In one example, the CSC is a leukemia CSC and the specific binding agent of the IR700-molecule recognizes one or more of (or more than one IR700-molecule conjugate is used): BMI-1, GLI-1, CD34, GLI-2, CD38, IL-3 R alpha/CD123, CD44, MICL/CLEC12A, CD47, Musashi-2, CD96, TIM-3, and CD117/c-kit. In one example, the CSC is a liver CSC and the specific binding agent of the IR700-molecule recognizes one or more of (or more than one IR700-molecule conjugate is used): alpha-Fetoprotein (AFP), CD90/Thy1, aminopeptidase N/CD13, NF2/Merlin, and CD45. In one example, the CSC is a lung CSC and the specific binding agent of the IR700-molecule recognizes one or more of (or more than one IR700-molecule conjugate is used): ABCG2, CD117/c-kit, Aldehyde Dehydrogenase 1-A1/ALDH1A1, EpCAM/TROP1, and CD90/Thy1. In one example, the CSC is a melanoma CSC and the specific binding agent of the IR700-molecule recognizes one or more of (or more than one IR700-molecule conjugate is used): ABCB5, MS4A1/CD20, ABCG2, Nestin, ALCAM/CD166, and NGF R/TNFRSF16. In one example, the CSC is a myeloma CSC and the specific binding agent of the IR700-molecule recognizes one or more of (or more than one IR700-molecule conjugate is used): ABCB5, CD38, CD19, MS4A1/CD20, CD27/TNFRSF7, and Syndecan-1/CD138. In one example, the CSC is an osteosarcoma CSC and the specific binding agent of the IR700-molecule recognizes one or more of (or more than one IR700-molecule conjugate is used): ABCG2, Nestin, CD44, STRO-1, and endoglin/CD105. In one example, the CSC is av ovarian CSC and the specific binding agent of the IR700-molecule recognizes one or more of (or more than one IR700-molecule conjugate is used): alpha-Methylacyl-CoA Racemase/AMACR, CD117/c-kit, CD44, Endoglin/CD105. In one example, the CSC is a pancreatic CSC and the specific binding agent of the IR700-molecule recognizes one or more of (or more than one IR700-molecule conjugate is used): Aldehyde Dehydrogenase 1-A1/ALDH1A1, CXCR4, BMI-1, EpCAM/TROP1, CD24, PON1, and CD44. In one example, the CSC is a prostate CSC and the specific binding agent of the IR700-molecule recognizes one or more of (or more than one IR700-molecule conjugate is used): ABCG2, CD44, ALCAM/CD166, CD151, Aldehyde Dehydrogenase 1-A1/ALDHIA1, c-Maf, alpha-Methylacyl-CoA Racemase/AMACR, c-Myc, BMI-1, and TRA-1-60 (R).

Pharmacological Drugs

In some examples, the target is a drug whose pharmacokinetics it to be controlled. For example, the drug can be a pharmacological drug (such as a prescription medication or those available from a pharmacy) that has a desired therapeutic effect, but whose prolonged presence in the body may be undesirable. The disclosed methods and IR700-drug conjugates permit removal of the conjugated pharmaceutical agents from the body after a desired amount of time, such as after the drug has had its desired therapeutic effect. For example, IR700-drug conjugates can be administered to a subject at an effective amount, for a time sufficient for the drug to have its desired effect. The subject is then irradiated with NIR light under conditions that allow the IR700-drug complex to aggregate. The resulting aggregate is removed or degraded by the body, for example by the liver, thereby removing the drug from the body (or rendering it inactive). In some examples, the subject receives multiple rounds of administration of the IR700-drug conjugates followed by exposure to NIR light, such as at least 2, at least 3, at least 4, at least 5, at least 6, at least 7, at least 8, at least 9, at least 10, or at least 20, or more, rounds of such treatment.

Exemplary drugs that can be conjugated to IR700 and used in the disclosed methods (which are administered at effective amounts) include, but are not limited to: antineoplastic chemotherapeutic agents, antibiotics, alkylating agents and antioxidants, kinase inhibitors, and other agents. Other examples include microtubule binding agents, DNA intercalators or cross-linkers, DNA synthesis inhibitors, DNA and/or RNA transcription inhibitors, antibodies, enzymes, enzyme inhibitors, and gene regulators. Such agents are known in the art. Exemplary chemotherapeutic agents are described in Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; and Fischer Knobf, and Durivage (eds): The Cancer Chemotherapy Handbook, 4th ed. St. Louis, Mosby-Year Book, 1993).

"Microtubule binding agent" refers to an agent that interacts with tubulin to stabilize or destabilize microtubule formation thereby inhibiting cell division. Examples of microtubule binding agents that can be used in conjunction with the—methods provided herein include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds can be conjugated to IR700 and used with the methods disclosed herein: DNA and/or RNA transcription regulators, including, without limitation, actinomycin D, daunorubicin, doxorubicin and derivatives and analogs thereof. DNA intercalators and cross-linking agents that can be used include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include Gleevac, Iressa, and Tarceva that prevent phosphorylation and activation of growth factors.

In one example, the chemotherapy drug is epirubicin, topotecan, irinotecan, gemcitabine, iazofurine, valspodar, mitoxantrone, or Doxil (liposome encapculated doxiorubicine). In one example the drug is adriamycin, apigenin, zebularine, cimetidine, theophylline, or a derivative or analogs thereof.

In one example, the drug is a biologic agent (e.g., mAb) or a small molecule, such as those shown in the table below:

| Tumor-Specific Antigen | Exemplary Tumors | Exemplary Antibody/Small Molecules |
| --- | --- | --- |
| HER1 | Adenocarcinoma (e.g., colorectal cancer, head and neck cancer) | Cetuximab, panitumamab, zalutumumab, nimotuzumab, matuzumab. Small molecule inhibitors gefitinib, erlotinib, and lapatinib can also be used. |
| HER2 | breast cancer, ovarian cancer, stomach cancer, uterine cancer | Trastuzumab (Herceptin ®), pertuzumab |
| CD20 | Non-Hodgkin lymphoma | Tositumomab (Bexxar ®); Rituximab (Rituxan, Mabthera); or Ibritumomab tiuxetan (Zevalin, for example in combination with yttrium-90 or indium-111 therapy) |

-continued

| Tumor-Specific Antigen | Exemplary Tumors | Exemplary Antibody/Small Molecules |
|---|---|---|
| CD25 | T-cell lymphoma | Daclizumab (Zenapax) |
| CD33 | Acute myelogenous leukemia | Gemtuzumab (Mylotarg, for example in combination with calicheamicin therapy) |
| CD52 | chronic lymphocytic leukemia | Alemtuzumab (Campath) |
| CEA | colorectal cancer, some gastric cancers, biliary cancer | CEA-scan (Fab fragment, approved by FDA), colo101 |
| Cancer antigen 125 (CA125) | ovarian cancer, mesothelioma, breast cancer | OC125 monoclonal antibody |
| Alpha-fetoprotein (AFP) | hepatocellular carcinoma | ab75705 (available from Abcam) and other commercially available AFP antibodies |
| Lewis Y | colorectal cancer, biliary cancer | B3 (Humanized) |
| TAG72 | adenocarcinomas including colorectal, pancreatic, gastric, ovarian, endometrial, mammary, and non-small cell lung cancer | B72.3 (FDA-approved monoclonal antibody) |
| Vascular endothelial growth factor | Colorectal cancer | Bevacizumab (Avastin ®) |

In one example, the drug is a biologic agent (e.g., mAb) or a small molecule, for treating rheumatoid arthritis, such as tocilizumab or rituximab.

In one example, the drug is one or more of the following: antibiotic (e.g., penicillin, ampicillin, metronidazole, tetracycline, chloramphenicol, tobramycin, cipro, and the like), anti-hypertensive drug (e.g., thiazide diuretics, ACE inhibitors, calcium channel blockers, beta blockers, and angiotensin II receptor antagonists), antidepressant (e.g., selective serotonin reuptake inhibitors (SSRIs), serotonin-norepinephrine reuptake inhibitors (SNRIs), tricyclic antidepressants (TCAs), monoamine oxidase inhibitors (MAOIs), buprenorphine, tryptophan, antipsychotics, and St John's wort, for example prozac), analgesics (e.g., acetaminophen, non-steroidal anti-inflammatory drugs (NSAIDs), COX-2 inhibitor, and opioid drugs such as morphine, codeine, and oxycodone), reproductive hormone (e.g., estrogen, testosterone, and progesterone), blood thinners (e.g., warfarin), steroid (e.g., prednisone), stain to reduce cholesterol (e.g., Mevacor, Zocor, Pravachol), immunosuppressant (e.g., rapamycin, ciclosporin, and methotrexate, azathioprine, rituximab, or a steroid), or cytokine (e.g., GM-CSF) and other prescription drugs.

Exemplary Specific Binding Agents

The molecule in an IR700-molecule complex can be a specific binding agent that permits selective binding between the specific binding agent and a target agent. Specific binding agents are known in the art, and non-limiting examples are provided below. For example, the IR700-molecule conjugate can be an IR700-antibody conjugate, IR700-antibody fragment conjugate, IR700-Affibody® molecule conjugate, IR700-hapten conjugate, IR700-lectin conjugate, IR700-protein conjugate, IR700-nucleic acid molecule conjugate, or IR700-functional nucleic acid conjugate wherein the antibody, antibody fragment, Affibody® molecule, hapten, lectin, protein, nucleic acid molecule, and the functional nucleic acid can specifically bind to the target molecule. Commercially available specific binding agents, and known methods for their generation, permit one to make any IR700-specific binding agent complexes. For example, antibodies (and functional fragments thereof), DNAzymes, and aptamers are available for numerous agents, such as proteins (e.g., cytokines, tumor antigens, etc.), metals, small organic compounds and nucleic acid molecules. In addition, methods of making antibodies, functional nucleic acids, and nucleic acid molecules that are specific for a particular target are well known in the art.

Methods for attaching a specific binding agent to IR700 are routine. For example, IR700 can be conjugated to a protein (such as antibody) by using the NHS ester of IR700. In addition, IR700 can be conjugated to a nucleic acid (such as a functional nucleic acid) by using linker chemistry such as psoralen functionalized IR700 or click chemistry.

Antibodies and Antibody Fragments

Antibodies and antibody fragments specific for various molecules are well known in the art. Thus, in some examples, the molecule in an IR700-molecule complex is an antibody or fragment thereof, permitting specific binding between the antibody or antibody fragment and a target (such as a target protein). Antibodies that can be used in the methods provided herein include intact immunoglobulins, variant immunoglobulins, and portions of antibodies, such as an antigen binding fragment of a naturally occurring or recombinant antibody.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "$V_H$" refer to the variable region of an immunoglobulin heavy chain, including that of an Fv, scFv, dsFv or Fab. References to "$V_L$" or "$V_L$" refer to the variable region of an immunoglobulin light chain, including that of an Fv, scFv, dsFv or Fab.

Specific, non-limiting examples of binding fragments encompassed within the term antibody include Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains.

In one example the Ab is a genetically engineered Ab, such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, IL); Kuby, J., *Immunology*, 3$^{rd}$ Ed., W. H. Freeman & Co., New York, 1997. A chimeric antibody has framework residues from one species, such as human, and CDRs (which generally confer antigen binding) from another species, such as a murine antibody that specifically binds human EGFR.

In one example the Ab is a humanized Ab or humanized immunoglobulin. A humanized immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

In one example the Ab is a human antibody (also called a fully human antibody), which includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

In one example the Ab is a monoclonal antibody (mAb). A mAb is an antibody produced by a single clone of B lymphocytes or by a cell into which the light and heavy chain genes of a single antibody have been transfected. mAbs are produced by methods known to those of skill in the art, for instance by making hybrid antibody-forming cells from a fusion of myeloma cells with immune spleen cells. mAbs include humanized mAbs.

As used herein, the term antibody also includes recombinant antibodies produced by expression of a nucleic acid that encodes one or more antibody chains in a cell (for example see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123: 793, 1979; Morrison et al., *Ann Rev. Immunol.* 2:239, 1984).

In a specific example, the antibody is a biologic used to treat cancer, such as one specific for a tumor protein. For example, the following conjugates can be used: IR700-Panitumumab conjugate, IR700-Trastuzumab conjugate, IR700-conjugate, IR700-Zenapax conjugate, IR700-Simitect conjugate, IR700-J591 conjugate, or IR700-Cetuximab conjugate.

Affibody® Molecules

Affibody® molecules specific for various targets are well known in the art (e.g., from Affibody, Sona, Sweden). Thus, in some examples, the molecule in an IR700-molecule complex is an Affibody® molecule, permitting specific binding between the Affibody® molecules and a target (such as a target protein). Affibody® molecules are small protein antibody mimetics of about 6 kDa. In some examples, an Affibody® molecule consists of three alpha helices with 58 amino acids. In contrast, a mAb is about 150 kDa, and a single-domain antibody about 12-15 kDa. Affibody® molecules with unique binding properties are typically generated by randomization of 13 amino acids located in two alpha-helices involved in the binding activity of the parent protein domain. In some examples, amino acids outside of the binding surface are substituted in the scaffold to create a surface entirely different from the ancestral protein A domain. Specific Affibody® molecules binding a target protein can be "fished out" from pools (libraries) containing billions of different variants, using phage display.

Haptens

A hapten is a small molecule that generally can only elicit an immune response when attached to a larger carrier (such as a protein). Haptens are known in the art as incomplete or partial antigens. But because like antibodies they can bind to target molecules, in some examples the molecule in an IR700-molecule complex is a hapten, permitting specific binding between the hapten and a target (such as a target protein).

Lectins

In one example the specific binding agent is a lectin. Lectins are proteins that recognize and bind to specific carbohydrates, for example on the cell surface. Thus, in some examples the molecule in an IR700-molecule complex is a lectin, permitting specific binding between the lectin and a target carbohydrate. Lectins can be modified to include a protein or peptide extension allowing conjugation/attachment to IR700.

Lectins are found in animals, plants, and microorganisms, and specific examples are known in the art. For example, as shown below, the plant lectins wheat germ agglutinin, peanut lectin, and phytohemagglutinin recognize different oligosaccharides.

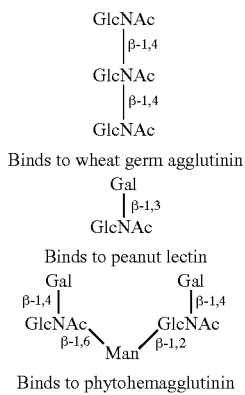

Exemplary lectins that can be used to remove a particular carbohydrate include but are not limited to: concanavalin A, lentil lectin, snowdrop lectin (all which bind mannose); ricin, peanut agglutinin, jacalin, and hairy vetch lectin (all which bind galactose); wheat germ agglutinin (which binds N-acetylglucosamine); elderberry lectin, *Maackia amurensis* hemoagglutinin (all which bind N-acetylneuraminic acid); and *Ulex europaeus* agglutinin and *Aleuria aurantia* lectin (all which bind fucose).

Proteins

In one example the specific binding agent is a protein. Proteins can be used that recognize and bind to specific proteins, nucleic acid molecules, and other binding partners. For example, a protein ligand can be used to bind to a specific receptor protein on a cell surface. Thus, in some examples the molecule in an IR700-molecule complex is a protein, permitting specific binding between the protein and a target protein, nucleic acid molecule, or other binding molecule, and removal of the molecule which binds to the protein (such as one that forms a covalent bond with the protein).

Protein-protein interactions are well known in the art, and include those involved in signal transduction, cellular transport, muscle function (actin/myosin). In addition, protein-nucleic acid molecule interactions are well known in the art, and include those that control the structure and function of the nucleic acid molecule (DNA or RNA), such as transcription, translation, DNA replication, repair and recombination and RNA processing and translocation.

Nucleic Acid Molecules

In one example the specific binding agent is a nucleic acid molecule. Nucleic acid molecules can be used that recognize and bind to specific proteins, nucleic acid molecules (via hybridization), and other binding partners. For example, a nucleic acid molecule that has sufficient complementarity to a target nucleic acid molecule can hybridize to the complementary sequence and remove the complementary sequence. Thus, in some examples the molecule in an IR700-molecule complex is a nucleic acid molecule, permitting specific binding between the nucleic acid molecule and a target protein, nucleic acid molecule, or other binding molecule, and removal of the molecule which binds to the nucleic acid molecule.

In one example, the target is a nucleic acid molecule, and the IR700-molecule conjugate includes nucleic acid molecule having a sequence of sufficient complementarity (sequence identity) to permit hybridization between the two nucleic acid molecules. For example, a nucleic acid molecule can have at least 80%, at least 90%, at least 91%, at least 92%, at least 93%, at least 94%, at least 95%, at least 96%, at least 97%, at least 98%, at least 99%, or 100% sequence identity to at least a portion of a target nucleic acid molecule, such as this level of sequence identity over at least 30 contiguous nucleotides of the target, at least 40, at least 50, at least 75, at least 100, at least 500, at least 1000, or at least 10,000 contiguous nucleotides of the target or more.

In addition, protein-nucleic acid molecule interactions are well known in the art, and include those that control the structure and function of the nucleic acid molecule (DNA or RNA), such as transcription, translation, DNA replication, repair and recombination and RNA processing and translocation.

Functional Nucleic Acids (FNAs)

In one example the specific binding agent is a functional nucleic acid molecule (FNA) (Liu et al, *Chem. Rev.* 2009, 109, 1948-1998). FNAs, including DNAzymes and DNA aptamers, are nucleic acid molecules (e.g., DNA or RNA) that recognize and bind to a wide range of targets with high affinity and specificities. Thus, in some examples the molecule in an IR700-molecule complex is a FNA, permitting specific binding between the FNA and a target, and removal of the target which binds to the FNA.

FNA sequences that can be modified or adapted to be used in the methods and IR700-molecule conjugates provided herein, are known in the art (e.g., see U.S. Pat. No. 8,058,415). One example of a FNA is a catalytic nucleic acid. The catalytic active nucleic acids can be catalytic DNA/RNA, also known as DNAzymes/RNAzymes, deoxyribozymes/ribozymes, DNA enzymes/RNA enzymes. Catalytic active nucleic acids can also contain modified nucleic acids. Aptazymes, RNAzymes, and DNAzymes become reactive upon binding an analyte by undergoing a chemical reaction (for example, cleaving a substrate strand of the FNA). In each instance, the outcome of the reactive polynucleotide becoming reactive is to cause disaggregation of the aggregate and the release of at least one oligonucleotide. Other example of a FNA is an aptamer, which undergoes a conformational change upon binding to the target. Aptamers become reactive upon binding an analyte by undergoing a conformational change.

FNAs can be selected from pools of DNA (usually 2~25 kDa) with ~$10^{15}$ random sequences via a process known as in vitro selection or Systematic Evolution of Ligands by EXponential enrichment (SELEX). DNAzymes and aptamers exhibit specific catalytic activity and strong binding affinity, respectively, to various targets. The targets can range from metal ions and small organic molecules to biomolecules and even viruses or cells.

Methods of identifying a FNA that is specific for a particular target agent are routine in the art and have been described in several patents. For example U.S. Pat. Nos. 7,192,708; 7,332,283; 7,485,419; 7,534,560; and 7,612,185, and US Patent Publication Nos. 20070037171 and 20060094026, describe methods of identifying functional DNA molecules that can bind to particular ions, such as lead and cobalt. In addition, specific examples are provided. Although some of the examples describe functional DNA molecules with fluorophores, such labels are not required for the methods described herein.

Aptamers are single stranded (ss) nucleic acids (such as DNA or RNA) that recognize targets with high affinity and specificity, which undergo a conformational change in the presence of their target. For example, the cocaine aptamer binds cocaine as its corresponding target. Thus, aptamers can be used as a specific binding agent. In vitro selection methods can be used to obtain aptamers for a wide range of target molecules with exceptionally high affinity, having dissociation constants as high as in the picomolar range (Brody and Gold, *J. Biotechnol.* 74: 5-13, 2000; Jayasena, *Clin. Chem.*, 45:1628-1650, 1999; Wilson and Szostak, *Annu. Rev. Biochem.* 68: 611-647, 1999). For example, aptamers have been developed to recognize metal ions such as Zn(II) (Ciesiolka et al., *RNA* 1: 538-550, 1995) and Ni(II) (Hofmann et al., *RNA*, 3:1289-1300, 1997); nucleotides such as adenosine triphosphate (ATP) (Huizenga and Szostak, *Biochemistry*, 34:656-665, 1995); and guanine (Kiga et al., *Nucleic Acids Research,* 26:1755-60, 1998); co-factors such as NAD (Kiga et al., *Nucleic Acids Research,* 26:1755-60, 1998) and flavin (Lauhon and Szostak, *J. Am. Chem. Soc.*, 117:1246-57, 1995); antibiotics such as viomycin (Wallis et al., *Chem. Biol.* 4: 357-366, 1997) and streptomycin (Wallace and Schroeder, RNA 4:112-123, 1998); proteins such as HIV reverse transcriptase (Chaloin et al., *Nucleic Acids Research,* 30:4001-8, 2002) and hepatitis C virus RNA-dependent RNA polymerase (Biroccio et al., *J. Virol.* 76:3688-96, 2002); toxins such as cholera whole toxin and staphylococcal enterotoxin B (Bruno and Kiel, *BioTechniques,* 32: pp. 178-180 and 182-183, 2002); and bacterial spores such as the anthrax (Bruno and Kiel, *Biosensors & Bioelectronics,* 14:457-464, 1999). Compared to antibodies, DNA/RNA based aptamers are easier to obtain and less expensive to produce because they are obtained in vitro in short time periods (days vs. months) and with limited cost. In addition, DNA/RNA aptamers can be denatured and renatured many times without losing their biorecognition ability.

DNA/RNAzymes typically contain a substrate strand that recognizes a target (and can include an RNA base) and a catalytic or enzyme domain. In some examples a co-factor, such as a metal ion, catalyzes substrate cleavage. For example, the lead DNAzyme binds lead as its corresponding target. Thus, DNA/RNAzymes can be used as specific binding agents. Aptazymes are the combination of aptamer and DNAzymes or ribozymes. Aptazymes work when the target binds to the aptamers which either triggers DNAzyme/ribozyme activities or inhibits DNAzyme/ribozyme activities. Thus, aptazymes can be used as specific binding agents.

Example 1

Synthesis of IRDye 700-Conjugated Trastuzumab (anti-Her2)

This example describes methods used to conjugate the monoclonal antibody Trastuzumab to the IRDye 700DX NHS Ester. On skilled in the art will recognize that any antibody, such as any monoclonal antibody specific for a target cell surface protein, can be conjugated to IRDye 700DX NHS Ester using similar methods.

Humanized anti-HER2 antibody, Trastuzumab (Tra; Genentech, San Francisco, CA) (1 mg, 6.8 nmol) was incubated with IRDye 700DX NHS Ester (IR700; LI-COR Bioscience, Lincoln, NE) (66.8 µg, 34.2 nmol, 5 mmol/L in DMSO) in 0.1 mol/L $Na_2HPO_4$ (pH 8.5) at room temperature for 30 to 120 min. Trastuzumab is a recombinant humanized monoclonal antibody (mAb) directed against the extracellular domain of the human epidermal growth factor receptor (EGFR) 2 (HER2) tyrosine kinase receptor. The mixture was purified with a Sephadex G50 column (PD-10; GE Healthcare, Piscataway, NJ). The protein concentration was determined with Coomassie Plus protein assay kit (Pierce Biotechnology, Rockford, IL) by measuring the absorption at 595 nm with a UV-Vis system (8453 Value System; Agilent Technologies, Palo Alto, CA). The concentration of IR700 was measured by absorption with the UV-Vis system to confirm the number of fluorophore molecules conjugated to each Trastuzumab molecule. The number of IR700 per Trastuzumab was about 3.

The purity of the Tra-IR700 conjugate was confirmed by analytical size-exclusion HPLC (SE-HPLC) and sodium dodecyl sulfate polyacrylamidegel elctrophoresis (SDS-PAGE). SE-HPLC was performed using a Beckman System Gold (Fullerton, CA) equipped with model 126 solvent delivery module, a model 168 UV detector, and a JASCO fluorescence detector (excitation 689 nm and emission at 700 nm) controlled by 32 Karat software. SE chromatography was performed on a TSKgel G2000SWxl (Tosoh Bioscience LLC, Montgomeryville, PA) eluted for 45 minutes using phosphate buffered saline (PBS) at 0.5 mL/min. SDS-PAGE was performed with a 4% to 20% gradient polyacrylamide gel (Invitrogen, Carlsbad, CA). Just after separating the proteins, fluorescence intensity was analyzed with a Fujifilm FLA-5100 fluorescence scanner (Valhalla, NY) with an internal laser of 670 nm for excitation and 705 nm long pass filter for emission. The fluorescence intensity of each band was analyzed with Multigage software (Fujifilm). The gels were then stained with Colloidal Blue Staining Kit (Invitrogen), and digitally scanned. The protein concentration in each band was analyzed with ImageJ software. The trastuzumab-1R700 (Tra-1R700) and panitumumab-1R700 (Pan-1R700; see Example 8) preparations demonstrated strong association and contained no detectable MAb aggregates as determined by high performance liquid chromatography (HPLC) and sodium dodecyl sulfate polyacrylamide-gel eletrophoresis SDS-PAGE.

To determine the in vitro binding characteristics of IR700 conjugates $^{125}I$ labeling of the conjugates using the Indo-Gen procedure was performed. The specific activities of the radiolabeled antibodies were 8.52 mCi/mg for Trastuzumab and 7.84 mCi/mg for panitumumab (see Example 8 below). It was observed that 73.38±0.39% ($^{125}I$-Tra-IR700) and 78.61±0.89% ($^{125}I$-Pan-IR700) of binding was achieved with each MAb conjugate respectively and the specificity of binding was confirmed by blocking with excess native unconjugated MAb (less than 1.4%). Since immunoreactivity of $^{125}I$-Tra and $^{125}I$-Pan measured with the same method were 78±2%, and 82±3%, respectively, minimal loss of MAbs with IR700 conjugation was confirmed. Immunoreactivity assay was performed as described previously. Briefly, after trypsinization, $2\times10^6$ of 3T3/HER2 or A431 cells were resuspended in PBS containing 1% bovine serum albumin (BSA). $^{125}I$-Tra-IR700 or $^{125}I$-Pan-IR700 (1 mCi, 0.2 µg) was added and incubated for 1 h on ice. Cells were washed, pelleted, the supernatant decanted, and counted in a 2470 Wizard² γ-counter (Perkin Elmer, Shelton, CT). Nonspecific binding to the cells was examined under conditions of antibody excess (200 µg of nonlabeled trastuzumab or panitumumab).

Example 2

Synthesis of IRDye 700-Conjugated Vectibix® (anti-HER1)

Panitumumab (Vectibix®), a fully humanized IgG$_2$ MAb directed against the human EGFR was purchased from Amgen (Thousand Oaks, CA) and conjugated to IR700 using the methods described in Example 1. This compound is referred to as Panitumumab-IR700 or Pan-IR700. The number of IR700 per Panitumumab was about 3.

Example 3

Synthesis of IRDye 700-Conjugated HuJ591

J591, a fully humanized IgG$_2$ MAb directed against human PSMA was obtained from Prof. Neil Bander, Cornell Univ and conjugated to IR700 using the methods described in Example 1. This compound is referred to as J591-IR700. The number of IR700 per J591 was about 2.

Example 4

Synthesis of IRDye 700-Conjugated Cetuximab

Cetuximab (Erbitux®), a chimeric (mouse/human) MAb directed against the human EGFR was purchased from Bristol-Myers Squibb (Princeton, NJ) and conjugated to IR700 using the methods described in Example 1. This compound is referred to as Cetuximab-IR700 or Cet-IR700. The number of IR700 per Cetuximab was about 3.

Example 5

Cleavage of IR700 After Exposure to NIR

Pan-IR700 was generated as described in Example 2. Pan-IR700 (2 µg) was suspended in PBS and exposed to NIR light (690 nm+/−20 nm for LED; 690 nm+/−4 nm for laser) using an LED or laser at 2, 4, 8 or 16 J/cm². The resulting solution was run on a 4-20% polyacrylamide gel, and stained with Comassie blue and visualized with light or fluorescence at 700 nm. Some samples were not exposed to NIR light.

Figure 4:
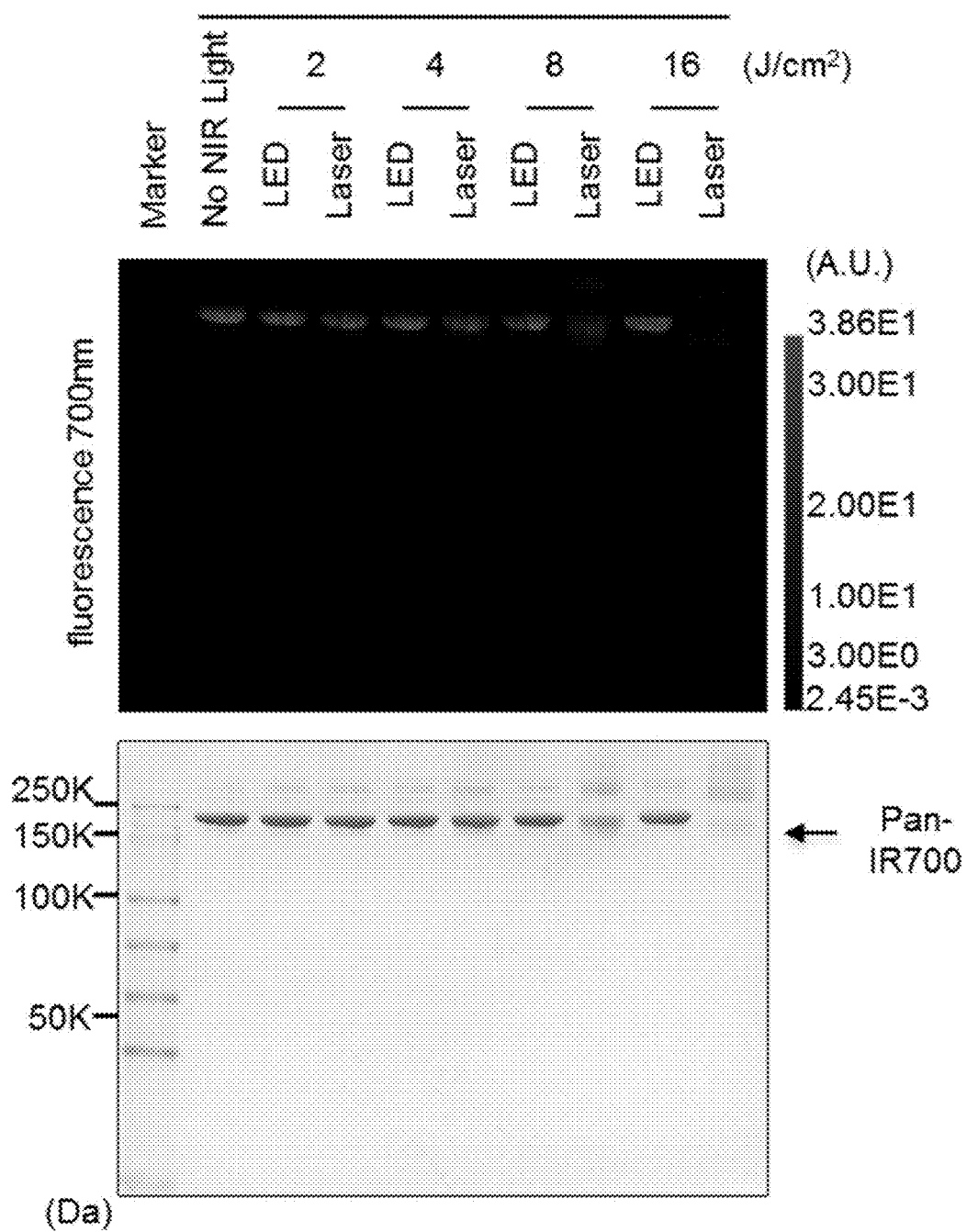
FIG. 4 is a digital image of a fluorescence image of a SDS-PAGE electrophoresis gel (top) and a Commassie blue gel (below). Both show the Pan-IR700 conjugate before (no NIR light) and after exposure to NIR light. As shown in the top gel, Pan-IR700 conjugates formed aggregates and fluorescence quenched, but no fluorescence was shown other than protein (no release of IR700 as small molecule). The blue Pan-IR700 band shows that the there is breakdown of the Pan-IR700 complex after exposure to NIR light (LED or laser).

The Commassie gel on the bottom of FIG. 4 shows that the Pan IR700 (blue band) was broken down or cleaved after exposure to NIR light (LED or laser). Similarly, the blurred bands in the top gel indicate that the Pan IR700 was cleaved. The top gel shows that the laser worked better than LED with the same light dose due to better efficient absorption of Laser emitting light that indicated absorbed light induced this photo-chemical reaction dose-dependently.

This aggregation of the cleaved Pan-IR700 complex can fall out of solution so that any molecule to which the Pan-IR700 complex is bound can be removed from the solution.

Example 6

IR700 Does Not Loose Fluorescence After Exposure to NIR

IR700 (0.5 µM) was suspended in DMF or PBS and exposed to NIR light with a laser (690 nm+/−4) at 2, 4, 8 or 16 J/cm². The resulting solution was visualized (in an eppendorf tube) with fluorescence at 700 nm. Some samples were not exposed to NIR light.

As shown in FIG. 5, the IR700 is still fluorescent even after exposure to strong NIR light. Thus, IR700 does not photobleach even though a significant degradation product is released after exposure to NIR light.

Example 7

IR700 Can Be Cleaved by NIR in the Absence of Oxygen

Pan-IR700 was generated as described in Example 2. Pan-IR700 (2 µg) was suspended in PBS and exposed to NIR light (690 nm+/−20 nm for LED; 690 nm+/−4 nm for laser) using an LED or laser at 0, 8 or 16 J/cm². Some examples contained NaN$_3$ (sodium azide), a reactive oxygen scavenger, or no oxygen (using an argon gas flash for 20 minutes). The resulting solution was run on a SCS-PAGE gel, and stained with Comassie blue and visualized with light or fluorescence at 700 nm. Some samples were not exposed to NIR light.

Figure 6:
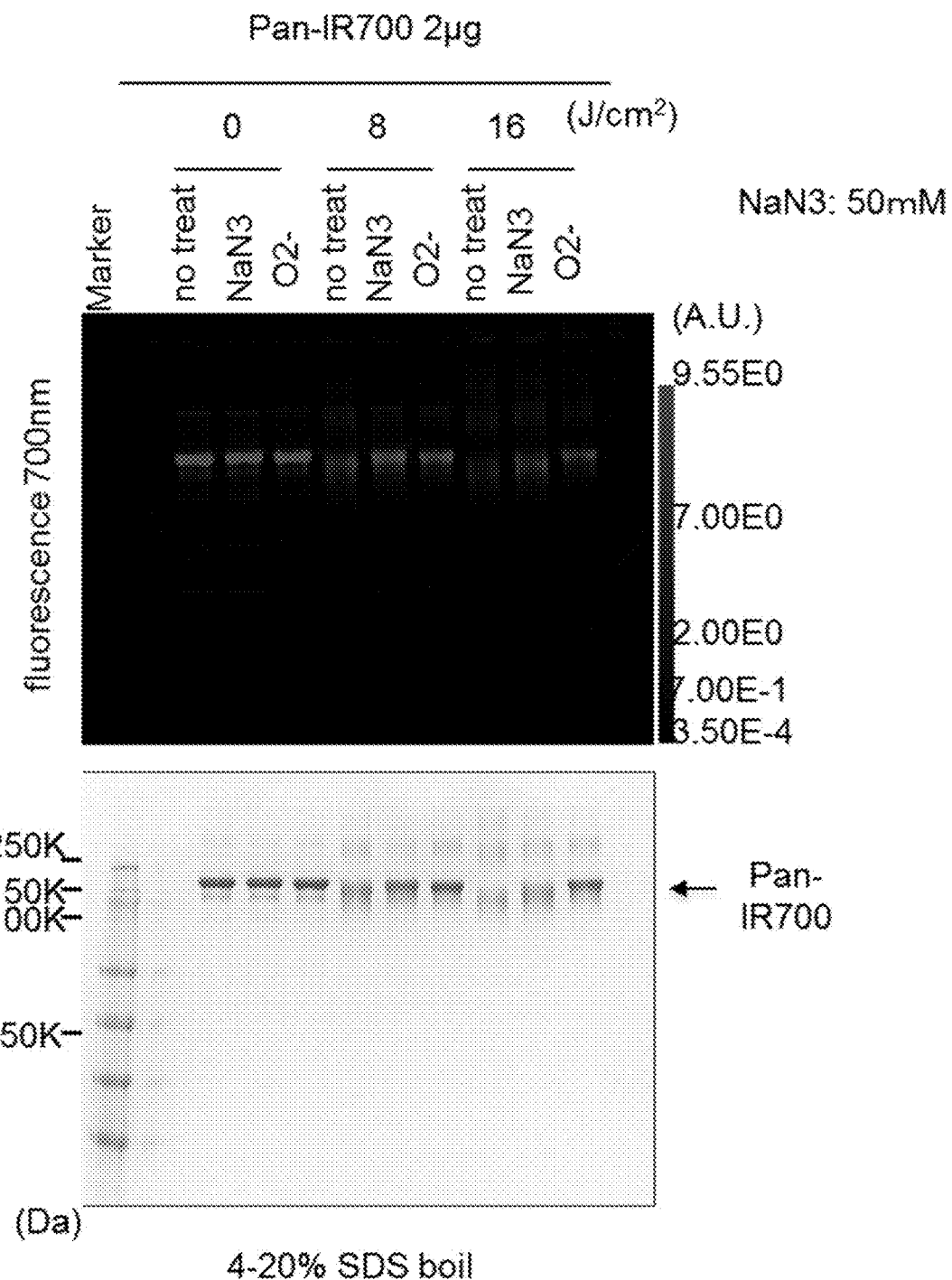
FIG. 6 is a digital image of a fluorescence image of a SDS-PAGE electrophoresis gel (top) and a Commassie blue gel (below). Both show the Pan-IR700 conjugate before and after exposure to NIR light, with (no treatment) or without (NaN$_3$ or O2-) oxygen.
Figure 7:
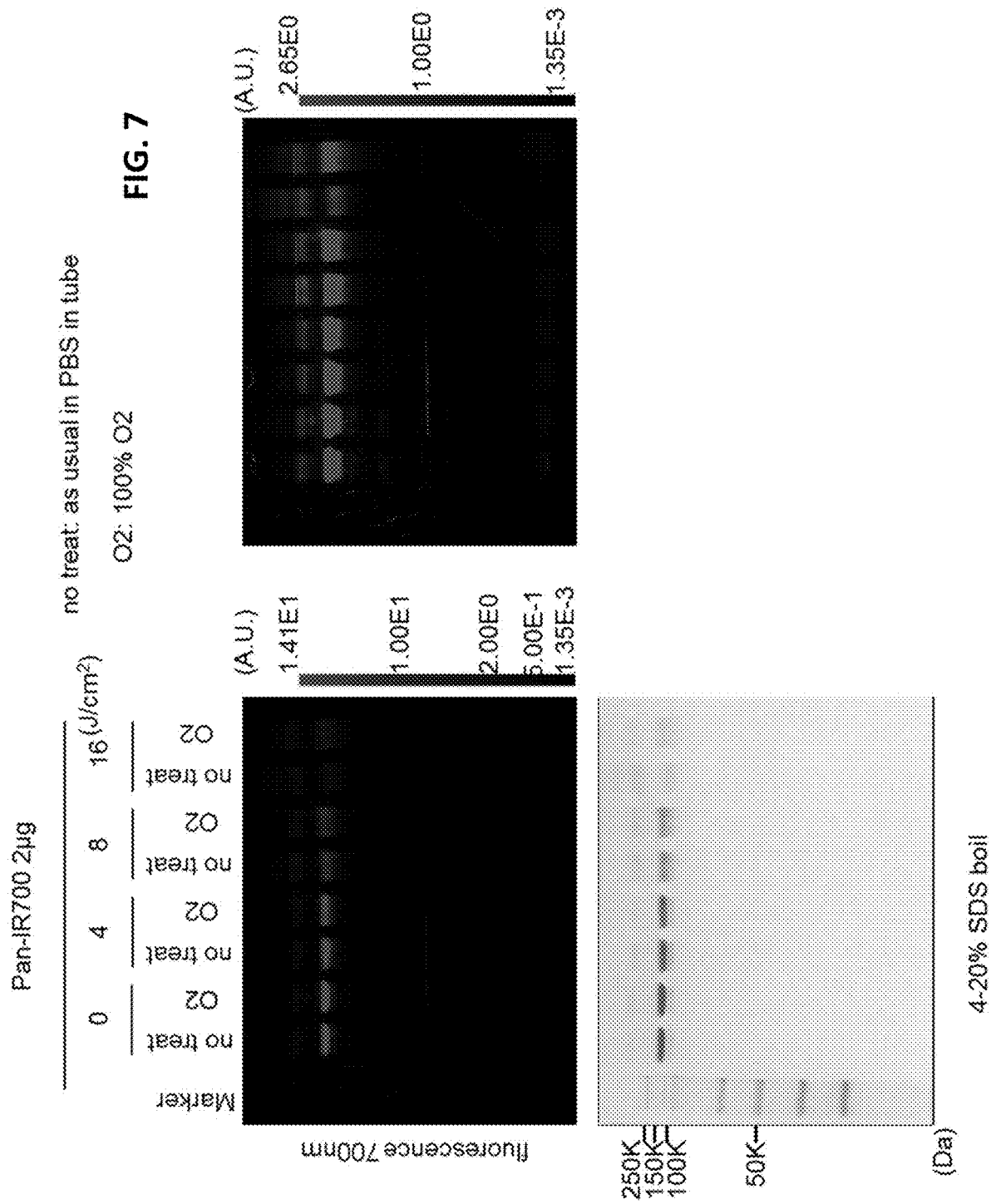
FIG. 7 is a digital image of a fluorescence image of a SDS-PAGE electrophoresis gel (top) and a Commassie blue gel (bottom). All show the Pan-IR700 conjugate before and after exposure to NIR light, with or without excess oxygen. The level and window setting is different to better show amount of aggregation. With 100% $O_2$, aggregation, aggregate formation is less efficient. This supports the chemical reaction shown in FIGS. 1 and 2.

As shown in FIG. 6, a strong Pan IR700 band is observed in the first three lanes (no NIR). Lanes 4-6 are at 8 J/cm² of NIR and show blurring of the Pan-IR700 band even with no oxygen (O2-). This is also seen in lanes 7-9 at 16 J/cm² of NIR. Thus, cleavage of IR700 occurs at normal oxygen (no treatment), with a ROS scavenger (NaN$_3$) and in hypoxia conditions, indicating the process is oxygen independent.

Example 8

Oxygen Saturation Can Reduce Cleavage of IR700 by NIR

Pan-IR700 was generated as described in Example 2. Pan-IR700 (2 µg) was suspended in PBS and exposed to NIR light (690 nm+/−20 nm for LED; 690 nm+/−4 nm for laser) using an LED or laser at 0, 4, 8 or 16 J/cm². Some examples contained excess oxygen (using 100% oxygen gas flash for 20 minutes). The resulting solution was run on a 4-20% SDS-PAGE gel, and stained with Comassie blue and visualized with light or fluorescence at 700 nm. Some samples were not exposed to NIR light.

As shown in FIG. 6, the presence of excess oxygen (100%) resulted in less degradation of the Pan1R700, indicating that oxygen saturation reduces or inhibits the cleavage of IR700 in the presence of NIR. The gel on the show different level and window settings to better show the amount of aggregation. With 100% O$_2$, aggregation formation is less efficient that supports the chemical reaction shown in FIGS. 1 and 2.

Example 9

In Vivo Trafficking of Cleaved IR700

$^{111}$In-DTPA-IR700-Pan was generated as described in Example 2, except that SCN-Bz-PTPA was conjugated to Pan-IR700. SCN-Bz-DTPA was solved in Pan-IR700 in borate buffer pH 8.5. Purification was performed by gel filtration with G25 gel.

$^{111}$In-DTPA-IR700-Pan was exposed to NIR light ex vivo (before injection, laser), or in vivo following injection (expose large part of abdomen, belly). $^{111}$In-DTPA-IR700-Pan (100 μg/mouse) was injected into A431-bearing mice. One hour following NIR exposed $^{111}$In-DTPA-IR700-Pan administration or NIR exposure to the belly, organs were harvested and analyzed as follows. Mice were sacrificed and dissected to separate all major organs. Organs were harvested, weighed and counted with a gamma counter (Wizard 2') to quantify the radioactivity in the organs.

Figure 8:
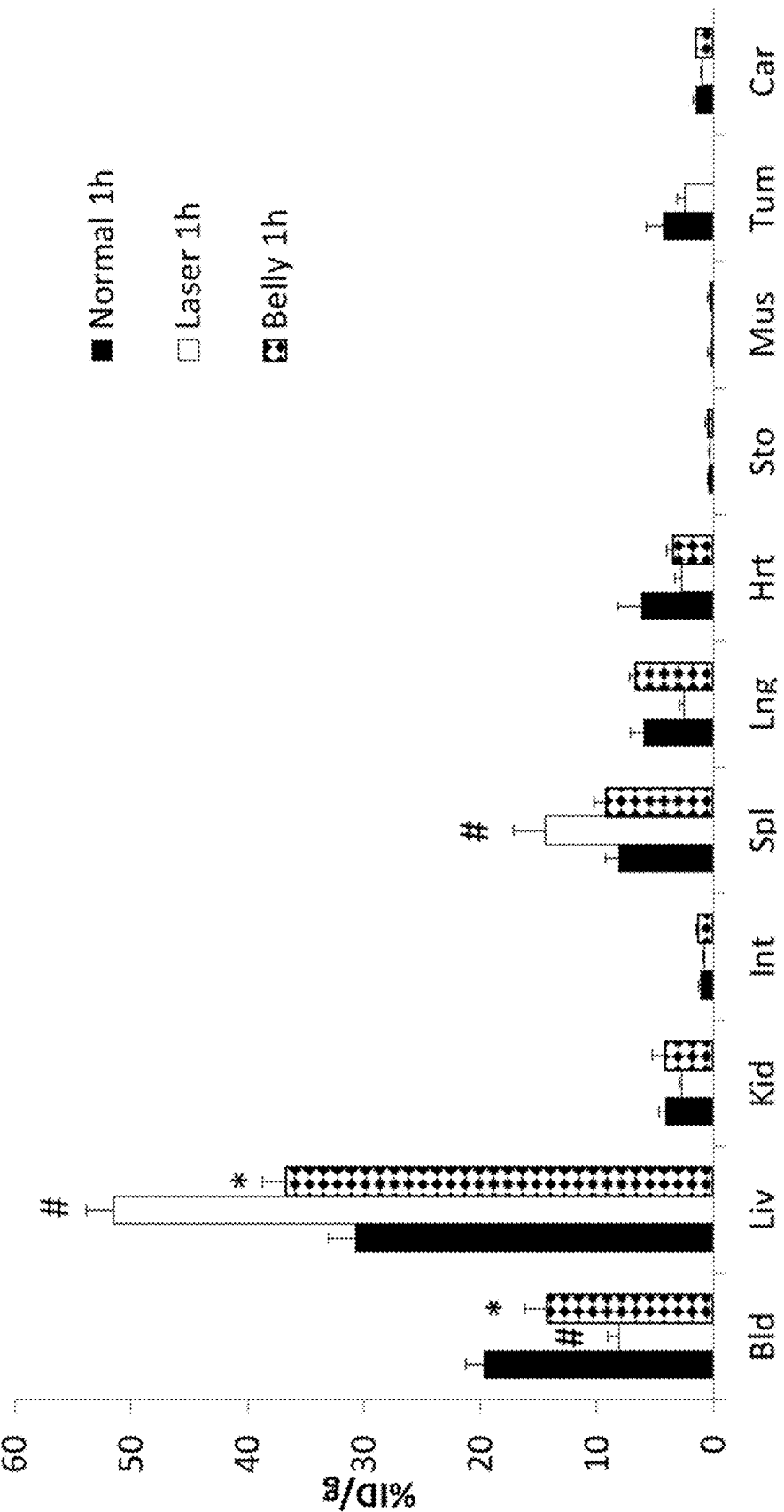
FIG. 8 is a bar graph showing what happens to Pan-IR700 following administration to a mouse with an EGFR-expressing tumor. The graph shows the biodistribution of the radiolabeled Pan-IR700 following exposure to NIR light ex vivo (before injection, laser), or in vivo (expose large part of abdomen, belly) in the organs removed from the body after treatment. Normal (n=5): without laser, Laser (n=5): 16 J laser, Belly (n=4): 30 J laser irradiate to belly. * p<0.05 and #p<0.01 compared to normal.

As shown in FIG. 8, after exposing to NIR light ex vivo (before injection) or in vivo (expose large part of abdomen), $^{111}$In-DTPA-IR700-Pan redirected to the liver and spleen. This indicates that an aggregate was formed and trapped by macrophages in the reticuloendothelial system. In the absence of NIR, there is accumulation of the cleaved conjugate in the liver. However, following NIR exposure, the amount of the cleaved conjugate in the liver dramatically increases, even if the NIR is delivered to the belly of the mouse (not where the tumor is). The same thing is observed in the spleen. This is consistent with aggregation of the Pan-IR700 that is taken up by the liver and spleen, indicating an increase in hydrophobicity of the complex after light therapy.

Thus, conjugation of IR700 to a drug or specific binding agent can be used to control the pharmacokinetics of the drug or of the specific binding agent, by clearing these to the liver and spleen. Such methods are useful in "clearing" or "chasing" a drug or specific binding agent from the body, for example to avoid toxicity or, in effect "turn it off". Such methods can also be used to remove agents that bind to the drug or the specific binding agent from the body, by clearing these to the liver and spleen.

Example 10

Figure 9:
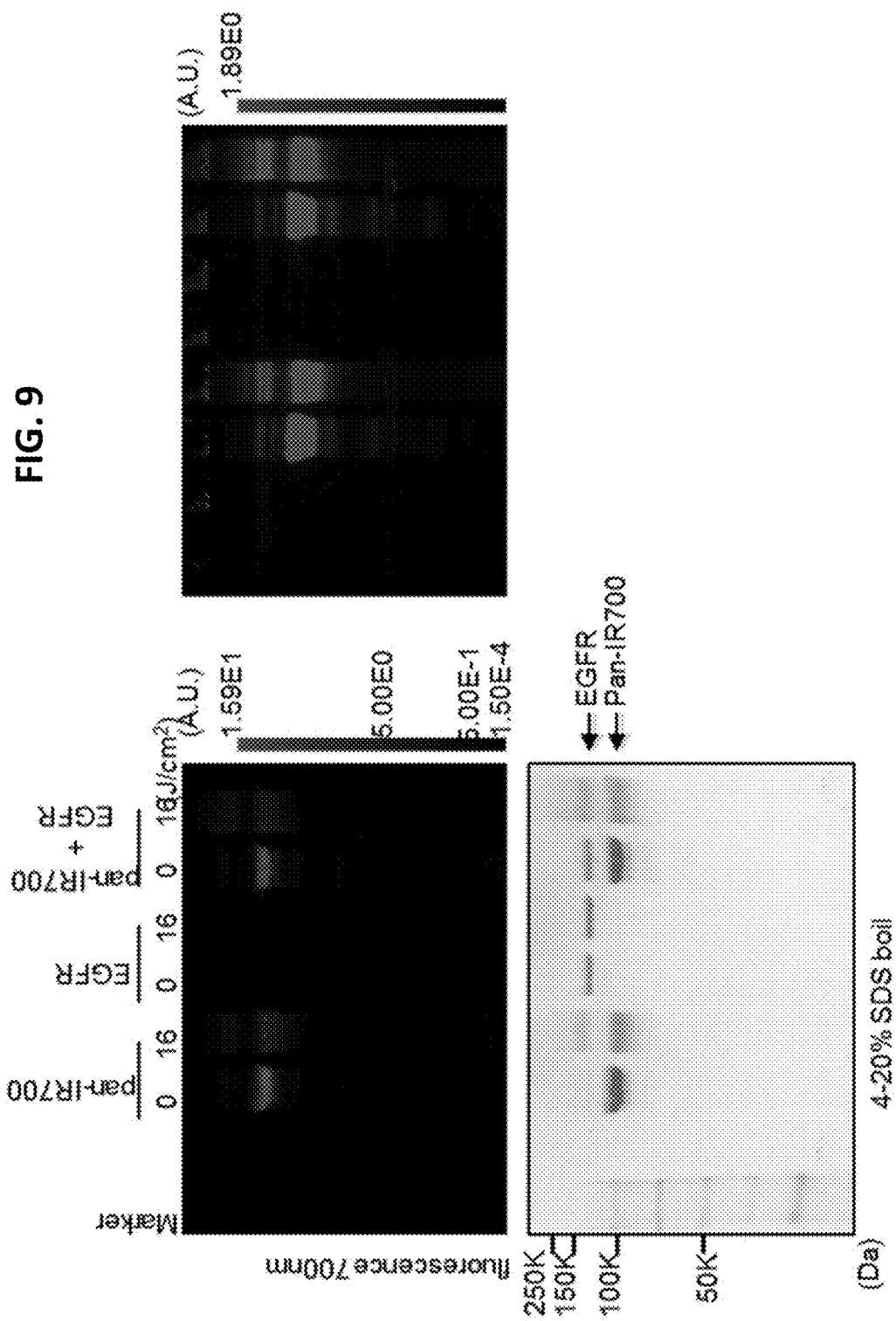
FIG. 9 is a digital image of fluorescence images of SDS-PAGE electrophoresis gels (top) and a Commassie blue gel (bottom). The Commassie blue gel shows that with exposure of 16 J/cm$^2$ NIR light, the EGFR band disappeared and incorporated into bands of Pan-IR700 aggregation (larger molecular weight band, see also Pan-IR700 only with 16 J/cm$^2$).

Panitumumab-IR700 was mixed with soluble EGFR at molar ratio 4:1, with or without irradiation of NIR (16 J/cm$^2$ with 690 nm laser). As shown in FIG. 9, EGFR molecules aggregate with antibody following NIR, and thus can be eliminated from solution (confirmed by SDS-PAGE). Once fully formed aggregates, the completion of aggregation formation was determined by shutting down the IR700 fluorescence.

Example 11

Materials and Methods

This example provides the materials and methods for the results described in Example 12.

Reagents

Water soluble, silicon-phthalocyanine derivative, IRDye 700DX NHS ester was from LI-COR Bioscience (Lincoln, NE, USA). Panitumumab, a fully humanized IgG2 mAb directed against EGFR, was from Amgen (Thousand Oaks, CA, USA). Trastuzumab, 95% humanized IgG1 mAb directed against HER2, was from Genentech (South San Francisco, CA, USA). All other chemicals were of reagent grade.

Synthesis of IR 700-Conjugated Trastuzumab, Panitumumab, or Anti-PSMA Antibody

Conjugation of dyes with mAbs was performed according to previous reports (Mitsunaga et al., *Nat. Med.* 17, 1685-1691, 2011; Sato et al., *Mol. Oncol.* 8, 620-632, 2014). Briefly, panitumumab, trastuzumab or anti-PSMA ab (1 mg, 6.8 nmol) was incubated with IR700 NHS ester (60.2 μg, 30.8 nmol) in 0.1 mol/L Na2HPO4 (pH 8.6) at room temperature for 1 hr. The mixture was purified with a Sephadex G50 column (PD-10; GE Healthcare, Piscataway, NJ, USA). The protein concentration was determined with Coomassie Plus protein assay kit (Thermo Fisher Scientific Inc, Rockford, IL, USA) by measuring the absorption at 595 nm with spectroscopy (8453 Value System; Agilent Technologies, Santa Clara, CA, USA). The concentration of IR700 was measured by absorption at 689 nm with spectroscopy to confirm the number of IR700 molecules conjugated to each mAb. The synthesis was controlled so that an average of four IR700 molecules were bound to a single antibody. SDS-PAGE was used as a quality control for each conjugate as previously reported (Sano et al., *ACS Nano* 7, 717-724, 2013). IR700 conjugated to trastuzumab is abbreviated as Tra-IR700, to panitumumab as Pan-IR700 and to anti-PSMA antibody as PSMA-IR700.

Cell Culture

GFP and luciferase stably expressed A431, 3T3/HER2 (HER2 stably expressed Balb/3T3 cells) or PC3-PIP (PSMA stably expressed PC3 cells) cells were established with a transfection of RediFect Red-FLuc-GFP (PerkinElmer, Waltham, MA, USA). High GFP and luciferase expression was confirmed with 10 passages. RFP stably expressed Balb/3T3 cells were established with transfection by RFP (EFIa)-Puro lentiviral particles (AMSBIO, Cambridge, MA, USA). High RFP expression was confirmed in the absence of a selection agent with 10 passages. These cells are abbreviated as A431-luc-GFP, 3T3/Her2-luc-GFP, PC3-PIP-luc-GFP, Balb/3T3-RFP, respectively. Cells were grown in RPMI 1640 (Life Technologies, Gaithersburg, MD, USA) supplemented with 10% fetal bovine serum and 1% penicillin/streptomycin (Life Technologies) in tissue culture flasks in a humidified incubator at 37° C. at an atmosphere of 95% air and 5% carbon dioxide.

3D Spheroid Culture

Spheroids were generated by the hanging drop method in which five thousand cells were suspended in 50 μL medium and then were dispensed into 96 well plates (3D Biomatrix Inc, Ann Arbor, MI, USA) following manufacturer's instructions (Sato et al., *Mol. Oncol.* 8, 620-632, 2014). Mixed spheroids were made with 5,000 cells of Balb/3T3-RFP and 500 cells of A431-luc-GFP (100:10)). After observation or treatment, spheroids were again incubated with the hanging drop plates containing new media. The volume of the spheroids was calculated with the formula: spheroid volume=$4/3$ π×radius$^3$ Flow Cytometry Fluorescence arising from the cells after incubation with APC agents was measured using a flow cytometer (FACS Calibur, BD BioSciences, San Jose, CA, USA) and Cell-Quest software (BD BioSciences). Cells (1×10$^5$) were incubated with each APC for 6 hr at 37° C. To validate the specific binding of the conjugated antibody, excess antibody (50 μg) was used to block 0.5 μg of dye-antibody conjugates (Sato et al., *Mol. Oncol.* 8, 620-632, 2014).

Fluorescence Microscopy

To detect the antigen specific localization of IR700 conjugates, fluorescence microscopy was performed (IX61 or IX81; Olympus America, Melville, NY, USA). Ten thousand cells were seeded on cover-glass-bottomed dishes and incubated for 24 hr. APC was then added to the culture medium at 10 μg/mL and incubated at 37° C. for 6 hr. The cells were then washed with PBS; Propidium Iodide (PI)(1:2000)(Life Technologies) and Cytox Blue (1:500)(Life Technologies), were used to detect dead cells. These were added to the media 30 min before observation. The cells were then exposed to NIR light and serial images were obtained. The filter was set to detect IR700 fluorescence with a 590-650 nm excitation filter, and a 665-740 nm band pass emission filter.

3D reconstructions of the spheroids were obtained with a confocal laser microscope (LSM5 meta, Carl Zeiss, Jena, Germany) after incubation for 30 min with Hoechst 33342 (1:500)(Life Technologies). Sections of spheroids were first fixed with 3.7% formaldehyde in PBS for 10 min at room temperature followed by embedding with OCT (SAKURA, Tokyo, Japan). Then, they were frozen at −80° C., and sliced at 10 μm with a cryotome (LEICA CM3050 S, Leica microsystems, Wetzlar, Germany). Analysis of the images was performed with ImageJ software (http://rsb.info.nih.gov/ij/).

In Vitro PIT

Two hundred thousand A431-luc-GFP cells were seeded into 24 well plates or twenty million cells were seeded onto a 10 cm dish and incubated for 24 hr. Medium was replaced with fresh culture medium containing 10 μg/mL of tra-IR700 which was incubated for 6 hr at 37° C. After washing with PBS, phenol red free culture medium was added. Then, cells were irradiated with a NIR laser, which emits light at 670 to 710 nm wavelength (L690-66-60; Marubeni America Co., Santa Clara, CA, USA). The actual power density (mW/cm2) was measured with an optical power meter (PM 100, Thorlabs, Newton, NJ, USA).

Cytotoxicity/Phototoxicity Assay

The cytotoxic effects of PIT with APC were determined by the luciferase activity and flow cytometric PI staining or GFP. For luciferase activity, 150 μg/mL of D-luciferin-containing media (Gold Biotechnology, St Louis, MO, USA) was administered to PBS-washed cells 1 hr after PIT, and analyzed on a bioluminescence imaging (BLI) system (Photon Imager; Biospace Lab, Paris, France). For the flow cytometric assay, cells were trypsinized 1 hr after treatment and washed with PBS. PI was added to the cell suspension (final 2 μg/mL) and incubated at room temperature for 30 min, prior to flow cytometry.

Estimation of GFP/RFP fluorescence Intensity In Vitro

Two hundred thousand cells were seeded on cover-glass-bottomed dishes and incubated for 12 hr. APC was then added to the culture medium (phenol red free) at 10 μg/mL and incubated at 37° C. for 6 hr. The cells were washed with PBS and media was replaced with a new, phenol red free culture medium and the under side of the cover glass was marked (to determine the position of observation). 1 hr after PIT, the cells were again observed. The GFP/RFP intensity was evaluated with total pixels with the same threshold in the same field of each spheroid20. Analysis of the images was performed with ImageJ software (http://rsb.info.nih.gov/ij/). Fluorescence from treated cells was also measured using a flow cytometer (FACS Calibur).

Animal and Tumor Models

All in vivo procedures were conducted in compliance with the Guide for the Care and Use of Laboratory Animal Resources (1996), US National Research Council, and approved by the local Animal Care and Use Committee. Six- to eight-week-old female homozygote athymic nude mice were purchased from Charles River (NCI-Frederick). During procedures, mice were anesthetized with isoflurane.

Four million A431-luc-GFP cells were injected subcutaneously in both (right and left symmetrically) flanks of the mice, for the monoculture tumor model. For the mixed tumor model, mixed cells of $4\times10^6$ A431-luc-GFP cells and $4\times10^5$ Balb/3T3-RFP cells (100:10) were injected subcutaneously in the both (right and left symmetrically) flanks.

In Vivo PIT

Mice were injected with 100 μg of pan-IR700 or irradiated as follows: (1) NIR light was administered at 50 J/cm2 on day 1 after injection and 100 J/cm2 on day 2 to the right tumor (2) no NIR light was administered to the left tumor that served as the control and was shield. Controls included (1) only NIR light exposure at 50 J/cm2 on day 1 and 100 J/cm2 on day 2 to the right tumor; (2) no treatment for the left tumor. These therapies were performed only once at day 7 after cell implantation. Mice were monitored daily, and serial image analysis was performed.

In Vivo Fluorescence Imaging

In vivo fluorescence images were obtained with a Pearl Imager (LI-COR Bioscience) for detecting IR700 fluorescence, and a Maestro Imager (CRi, Woburn, MA, USA) for GFP/RFP. For GFP/RFP, a band-pass filter from 445 to 490 nm (excitation) and a long-pass blue filter over 515 nm (emission) for GFP, 503 to 555 nm (excitation) and a long-pass green filter over 580 nm (emission) for RFP were respectively used. The tunable emission filter was automatically stepped in 10 nm increments from 515 to 580 nm at constant exposure (800 msec). The spectral fluorescence images consist of autofluorescence spectra and the spectra from GFP/RFP (tumor), which were then unmixed, based on the characteristic spectral pattern of GFP, using Maestro software (CRi). Regions of interest (ROIs) were manually drawn either on the flank tumor or over the abdominal region as appropriate to the model and fluorescence intensity was measured.

In Vivo Bioluminescence Imaging

For BLI, D-luciferin (15 mg/mL, 200 μL) was injected intraperitoneally and the mice were analyzed with a Photon Imager for luciferase activity at day 6. Mice were selected for further study based on tumor size and bioluminescence. For quantifying luciferase activities, ROI of similar size were placed over the entire tumor.

Statistical Analysis

Data are expressed as means±s.e.m. from a minimum of four experiments, unless otherwise indicated. Statistical analyses were carried out using a statistics program (Graph-Pad Prism; GraphPad Software, La Jolla, CA, USA).

Example 12

Selective Killing of Cell Subpopulations

Cell cultures and tissues often contain cellular subpopulations that potentially interfere with or contaminate other cells of interest. However, it is difficult to eliminate unwanted cells without damaging the very cell population one is seeking to protect. This example demonstrates that the disclosed methods can be used to significantly reduce or eliminate a specific subpopulation of cells from a mixed 2D or 3D cell culture and a mixed-population in vivo tumor model by using the near infrared photoimmunotherapy (PIT).

For both scientific and practical reasons, elimination of a particular type of cell from a cell culture or from in vivo tissue is often desirable, however, it is difficult to achieve without damaging adjacent cells or the entire organism. When a cell culture is contaminated with bacteria, it is relatively straightforward to eliminate them with antibiotics, however, when the contamination is with another eukaryotic cell type, selective elimination is more difficult. For example, tissue cultures based on stem cells (e.g., embryonic stem cells: ES, or induced pluripotent stem cell: iPS) play a key role in the field of regenerative medicine, and clinical trials are about to launch (Yamanaka, *Cell Stem Cell* 10, 678-84, 2012; Yamanaka & Blau, *Nature* 465, 704-12, 2010; Birchall & Seifalian, *Lancet* 6736, 11-12, 2014; Kamao et al., *Stem cell reports* 2, 205-18, 2014; and Klimanskaya et al., *Nat. Rev. Drug Discov.* 7, 131-42, 2008). During tissue regeneration, a potential concern is contamination with transformed cells leading to neoplasms (Okita, et al., *Nature* 448, 313-7, 2007; Ohnishi et al., *Cell* 156, 663-77, 2014; Ben-David & Benvenisty, *Nat. Rev. Cancer* 11, 268-77, 2011; and Knoepfler, *Stem Cells* 27, 1050-6, 2009). It would be highly desirable to selectively remove these transformed cells to maintain the integrity of the tissue graft.

An additional example of desirable selective cell elimination is the removal of specific immune cells from a tumor or inflammation for favorably altering immune cell networks with resulting effects on the overall growth rate of the tumor or the degree of inflammation. In this manner, host immunity could be intentionally modulated (Pardoll, *Nat. Rev. Cancer* 12, 252-64, 2012). Similarly, eliminating cancer stem cells from a tumor could prevent relapse (Valent et al., *Nat. Rev. Cancer* 12, 767-75, 2012). Although several groups investigated technologies for eliminating target cells from an established tissue or after transplantation, no clear practical method has been reported that does not also damage other cells in the same milieu (Miura et al., *Nat. Biotechnol.* 27, 743-5, 2009; Ben-David et al., *Nat. Commun.* 4, 1992, 2013; Lee et al., *Proc. Natl. Acad. Sci. U.S.A* 110, E3281-90, 2013; and Tang et al., *Nat. Biotechnol.* 29, 829-34, 2011).

Photoimmunotherapy (PIT) uses an antibody-photosensitizer conjugate (APC), composed of a monoclonal antibody (mAb) (or other specific binding agent) conjugated to a phthalocyanine-based photosensitizer (IR700). When exposed to near infrared (NIR) light, cytotoxicity is induced only in APC-bound target cells (Mitsunaga et al., *Bioconjug. Chem.* 23, 604-609, 2012).

The results below show the feasibility of using PIT for selectively eliminating a set of target cells. A mixed 2D and 3D (spheroid) cell culture, as well as a mixed tumor xenograft model, were used. Using the optical reporters, RFP, GFP and luciferase, different populations of cells were selectively eliminated by PIT. Thus, the disclosed methods can be used to eliminate or substantially reduce (such as reduce by at least 50%, at least 60%, at least 75%, at least 80%, at least 90%, at least 95%, at least 98%, at least 99%, or at least 99.9%, target cells from cell culture or tissue in vivo.

Figure 11A:
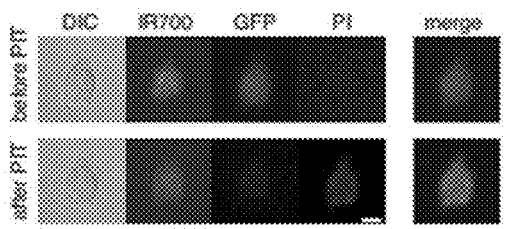
FIGS. 11A-11C show the observation and quantification of PIT effect on 2D cultures of A431-luc-GFP cells. (A) A431-luc-GFP cells were incubated with Pan-IR700 for 6 hr, and observed with a microscope before and after irradiation of NIR light (2 J/cm2). Necrotic cell death was observed after exposure to NIR light (1 hr after PIT). Bar=10 μm Membrane damage and necrosis induced by PIT was confirmed by dead cell PI staining. (B) Membrane damage and necrosis induced by PIT was measured by dead cell count using PI staining on FACS. (C) Cell killing increased in a NIR-light dose-dependent manner.
Figure 11C:
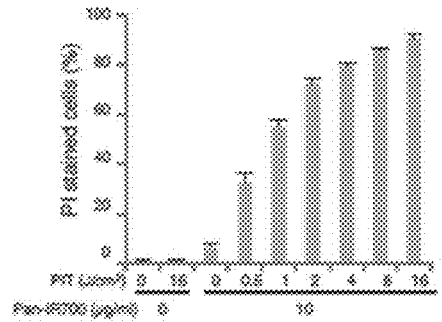
Figure 11B:
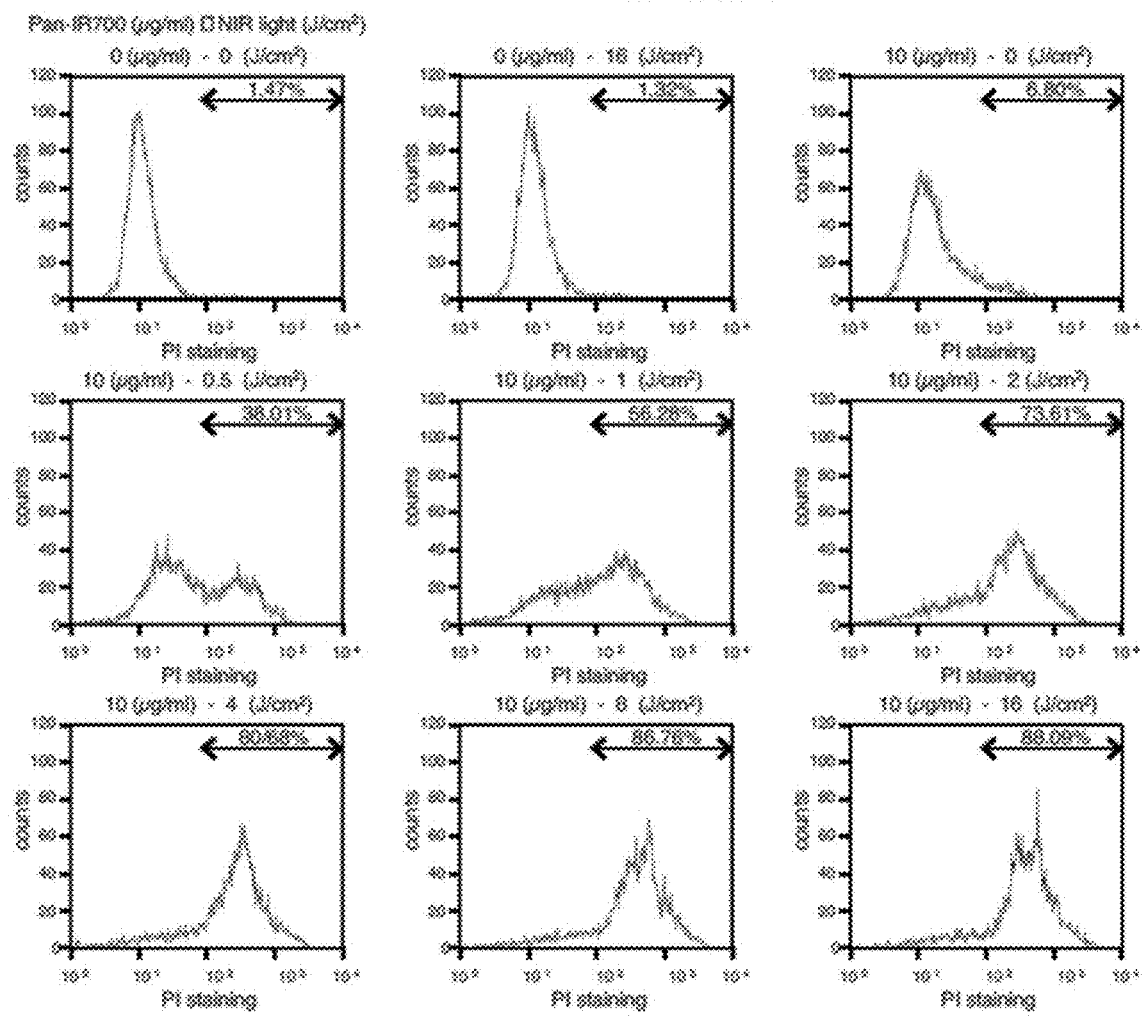
Figures 13A, 13B:
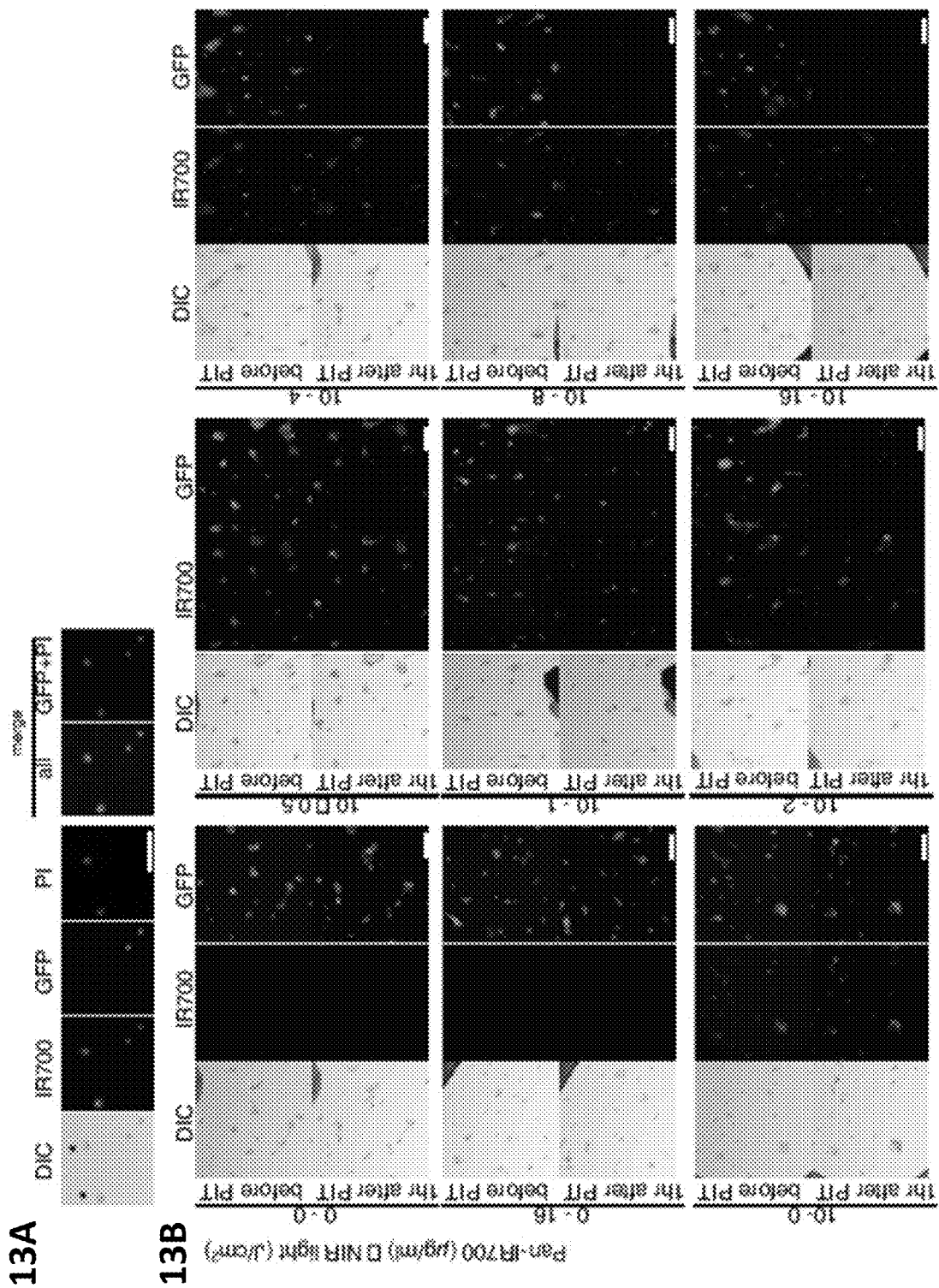
FIGS. 13A-13C show that GFP-fluorescence decreased at 1 hr after PIT in 2D cell culture. (A) A431-luc-GFP cells were incubated with Pan-IR700 for 6 hr and irradiated with NIR-light (0.5 J/cm2). GFP-fluorescence intensity decreased in dead cells (*) but was unchanged in living cells at 1 hr after PIT. Bar=50 m. (B) Diminishing GFP-fluorescence intensity at 1 hr after PIT occurred in a NIR-light dose-dependent manner. The black line at the right upper corner was the marker to ensure observation took place consistently. (C) Quantification of GFP-fluorescence intensity showed a decrease in a NIR-light dose-dependent manner (total pixel of GFP fluorescence in the same field) (n=12 fields).
Figures 13C, 14B:
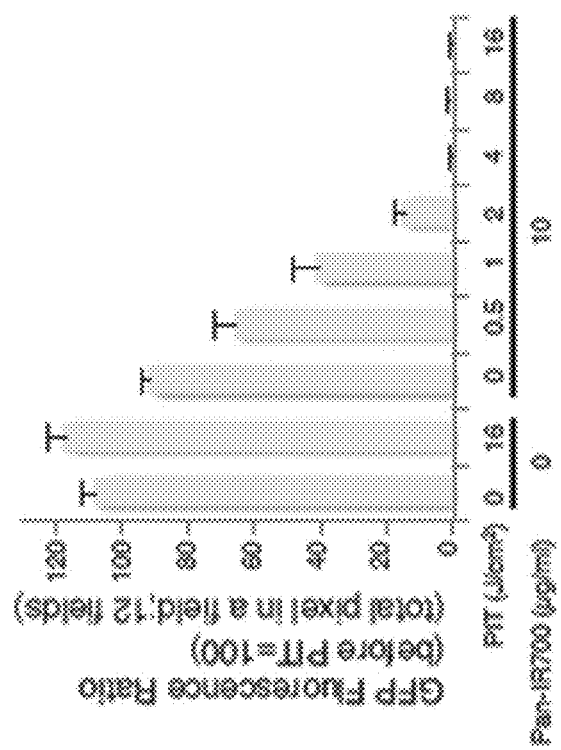
FIGS. 14A-14B show the decrease in GFP-fluorescence at 1 hr after PIT evaluated with flow cytometry. (A, B) GFP fluorescence intensity decreased after PIT in a NIR-light dose-dependent manner as measured by FACS.
Figure 14A:
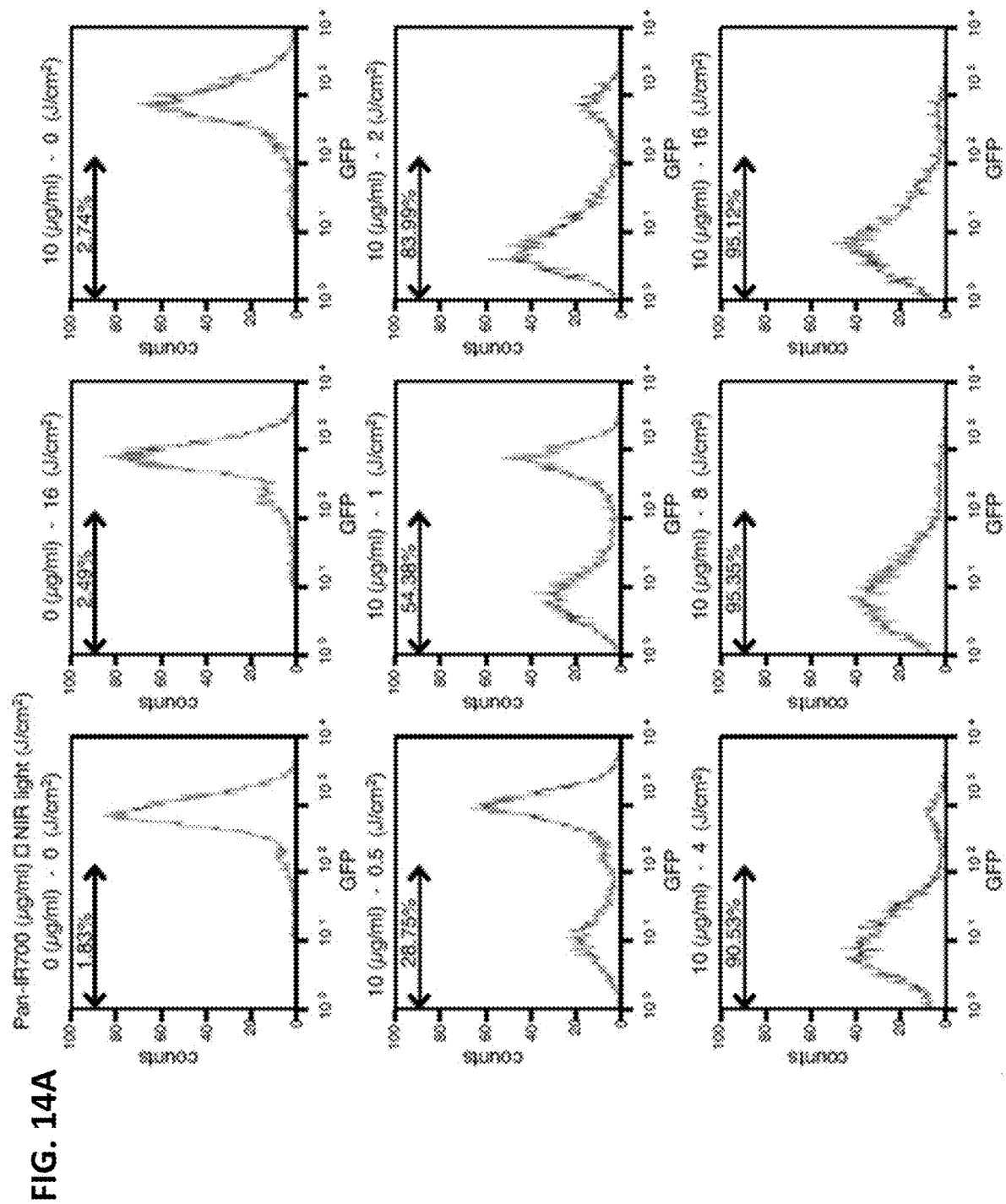

Two cell populations were used in these experiments, one tumor cell line expressing EGFR (A431) and the other control cell line, negative for EGFR (Balb/3T3). The A431 model was genetically modified to express GFP and luciferase (luc) while, Balb/3T3 was modified to express RFP (FIGS. 10A-0B). Specific binding of panitumumab-IR700 (Pan-IR700) to the target-expressing A431-luc-GFP cells was demonstrated, while no binding was shown for Balb/3T3-RFP cells (FIG. 10C). The killing efficacy of PIT on newly established A431-luc-GFP cells with Pan-IR700 was evaluated with dead PI staining in 2D cell culture in vitro (FIGS. 11A-11C). A431-luc-GFP cells were killed in a light-dose dependent manner. PIT induced a decrease in bioluminescence (BLI) and GFP fluorescence intensity also in a light-dose dependent manner (FIGS. 12A-C, FIGS. 13A-13C, and FIGS. 14A-14B), which was consistent with PI dead staining. These data indicated that PIT could be monitored with GFP fluorescence and BLI.

Next, the efficacy of PIT on 3D spheroids consisting of A431-luc-GFP or Balb/3T3-RFP was evaluated (FIG. 15A). These cells formed spheroids as large as approximately 500 µm in diameter (FIG. 15B). Three-dimensional confocal microscopy showed that these spheroids were indeed spherical (FIG. 15C). Fluorescence images of frozen sections revealed that cells were evenly dispersed throughout the spheroid (FIG. 15D). Pan-IR700 gradually permeated into spheroids from the perimeter as depicted on IR700-fluorescence microscopy; the stained area gradually spread toward the center of the spheroid in a time dependent manner (FIG. 15E).

Figure 16:
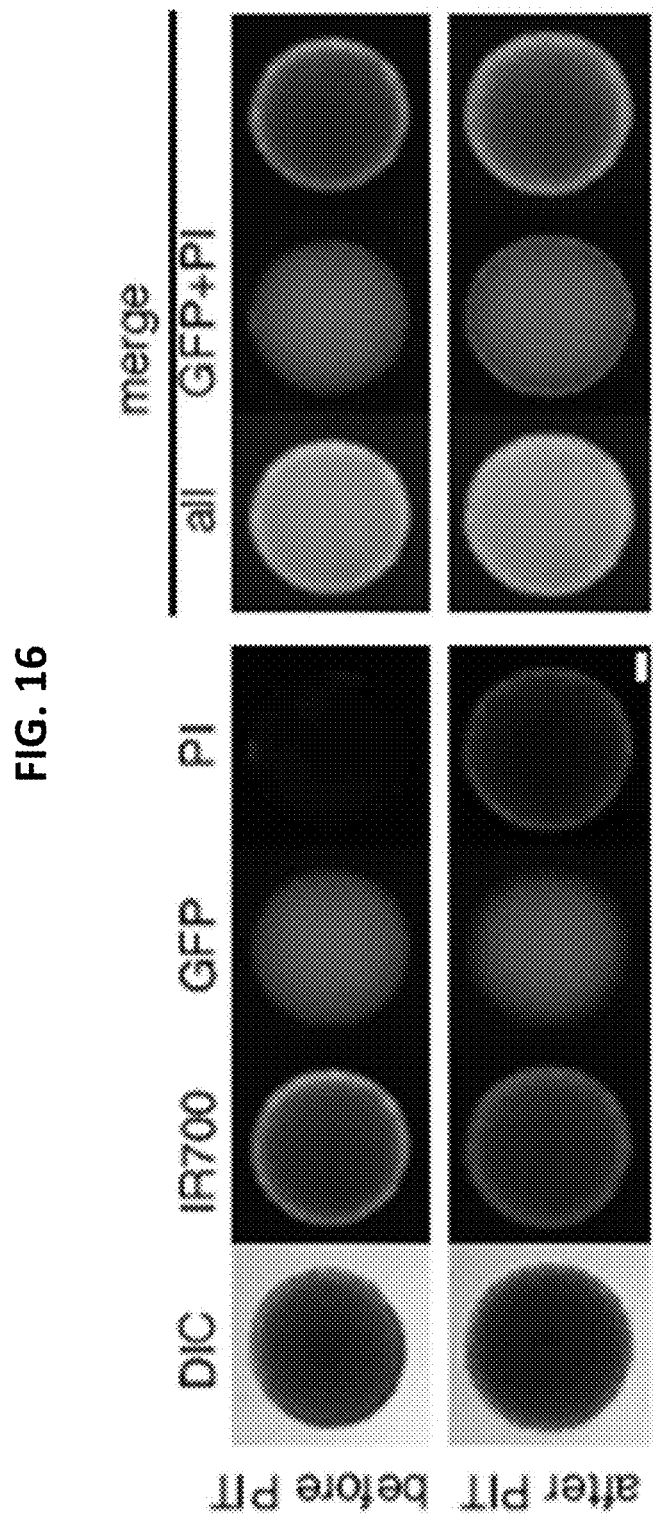
FIG. 16 shows the observation of PIT effect on 3D spheroids. 3D spheroid at day 7 after 6 hr incubation with Pan-IR700, before and 1 hr after irradiation of NIR light (2 J/cm2). Necrotic cell death was observed 1 hr after NIR light. Bar=100 m. Regions of decreased GFP fluorescence co-localize with PI staining.
Figures 17A, 17B:
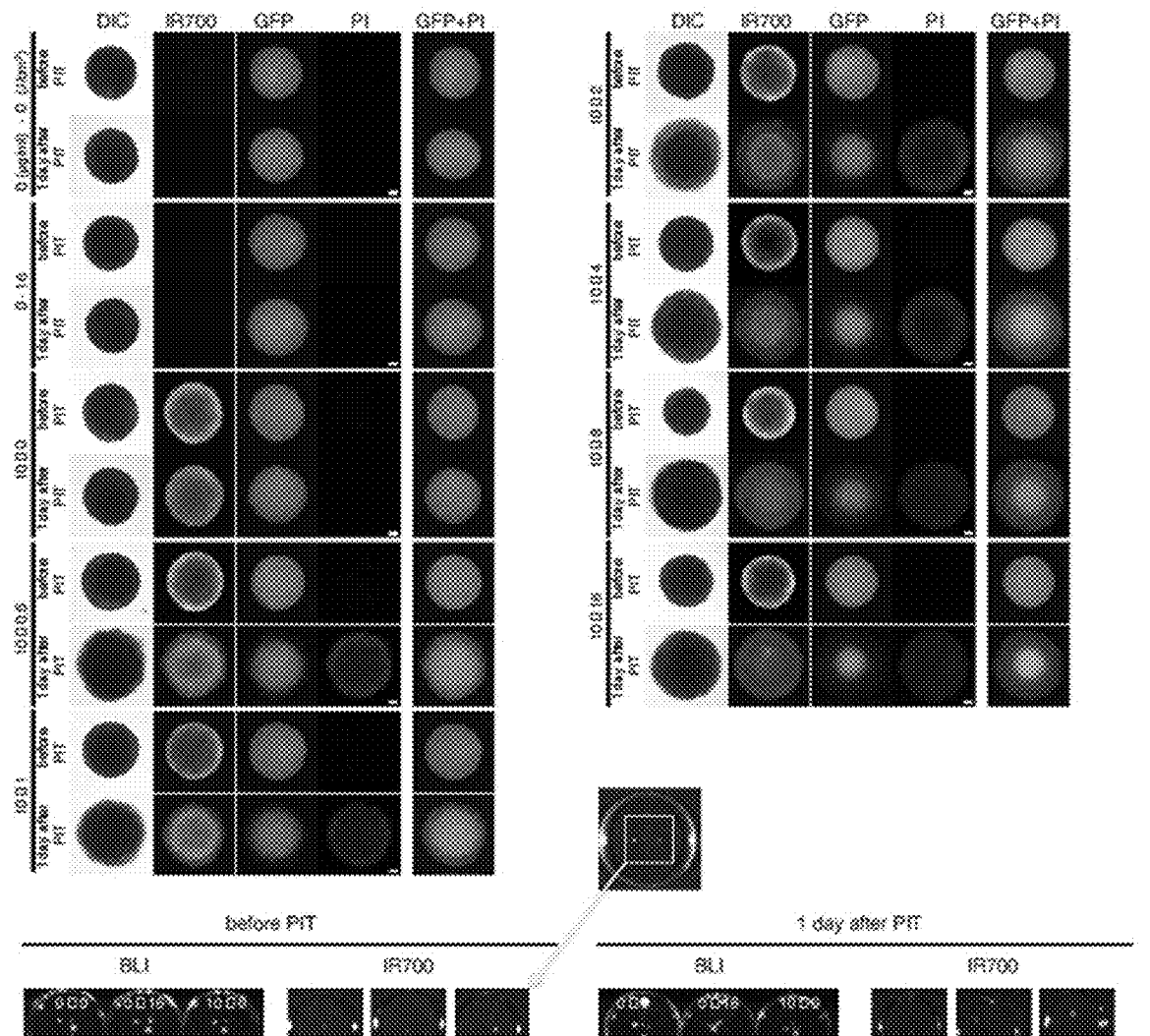
FIGS. 17A-17E show the evaluation of PIT effect on in vitro 3D spheroids. (A) Day 7 3D spheroid at after 6 hr incubation with Pan-IR700, before and 1 day after irradiation of NIR light. Necrotic cell death was observed 1 day after NIR light (stained by PI). Bar=100 μm. GFP-fluorescence intensity decreased and the spheroid decreased in size ("peeling") in a light dose dependent manner. (B) Bioluminescence imaging (BLI) of a spheroid in glass-bottom dish demonstrated that luciferase activity in A431-luc-GFP 3D spheroids decreased in a NIR-light dose-dependent manner at 1 day after PIT. Bar=5 mm. Macroscopic view of IR700 fluorescence was also demonstrated (Pearl Imager). (C) Quantification of GFP-fluorescence demonstrated a NIR-light dose-dependent decrease in intensity (total pixel of GFP fluorescence in the same spheroid) (n=10). (D) Bioluminescence in A431-luc-GFP 3D spheroids was measured as relative light units (RLU), and decreased in a NIR-light dose-dependent manner (n=10). (E) The volume of A431-luc-GFP 3D spheroids also decreased in a NIR-light dose-dependent manner (n=10).
Figure 17C:
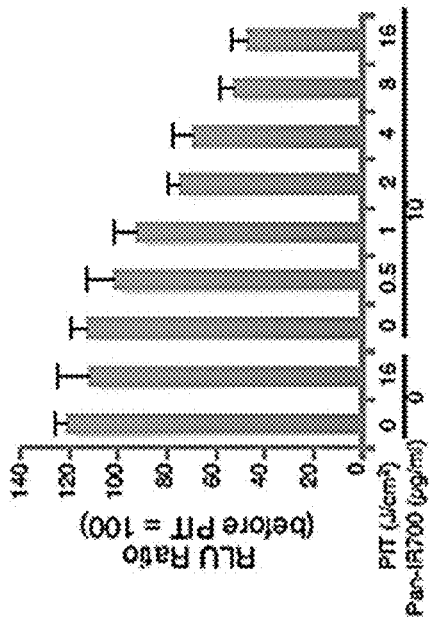
Figure 17D:
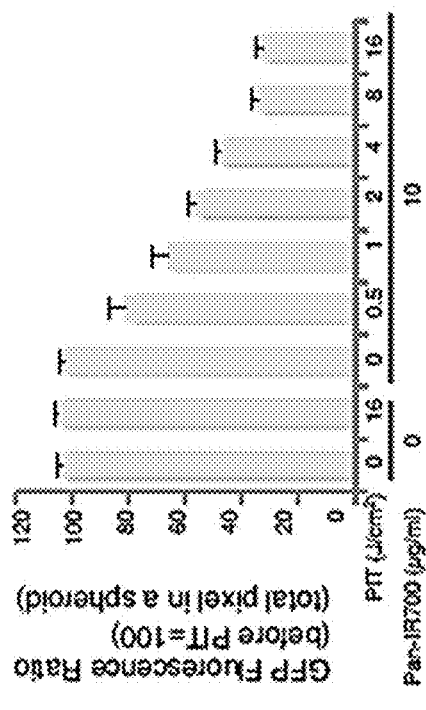
Figure 17E:
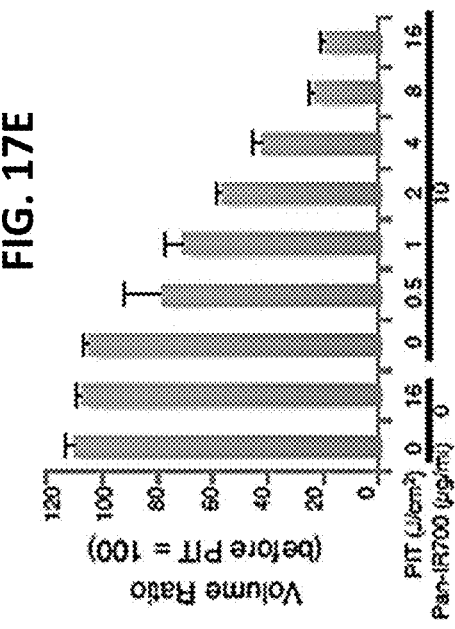
Figures 18A, 18B:
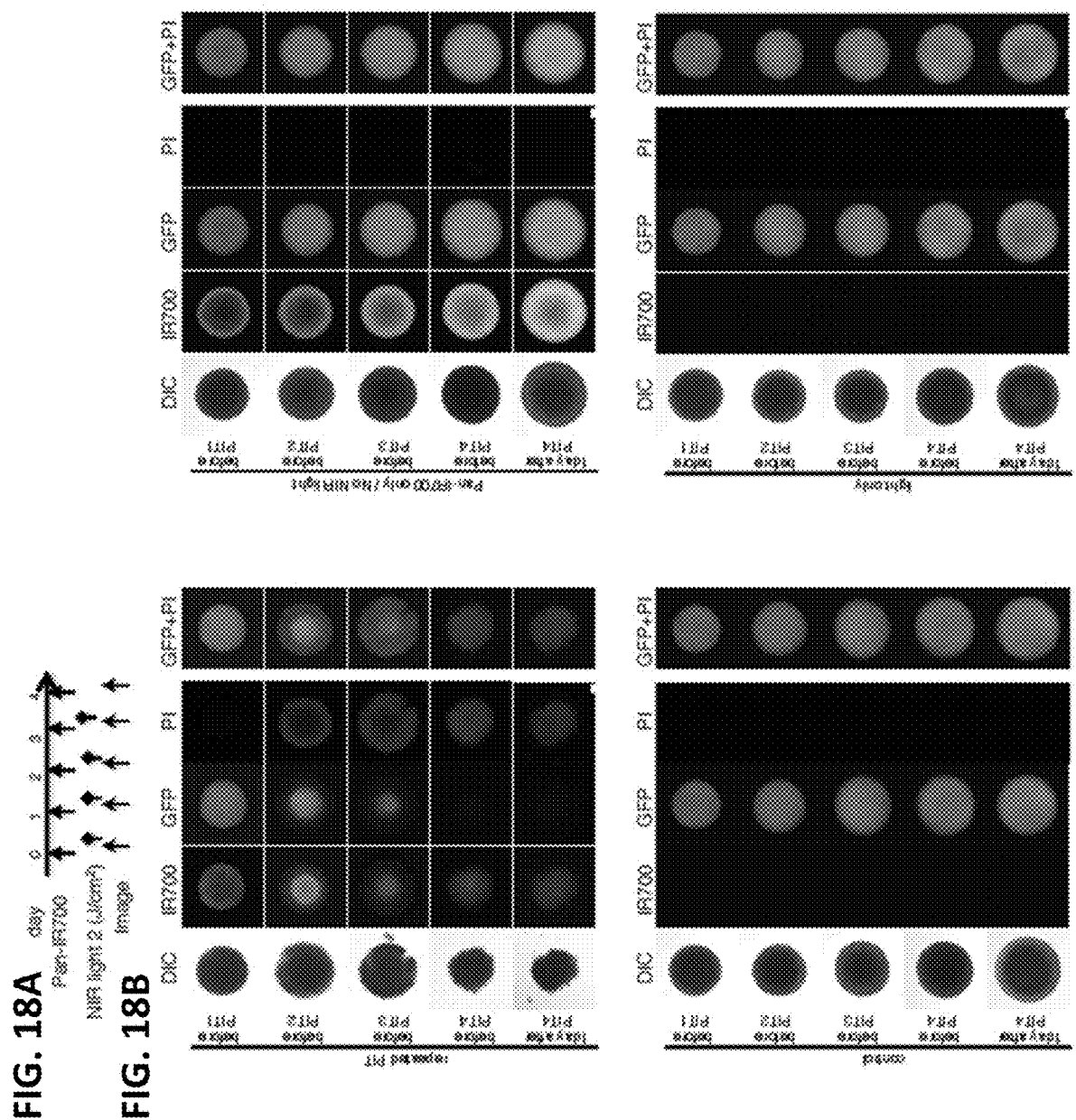
Figure 19A:
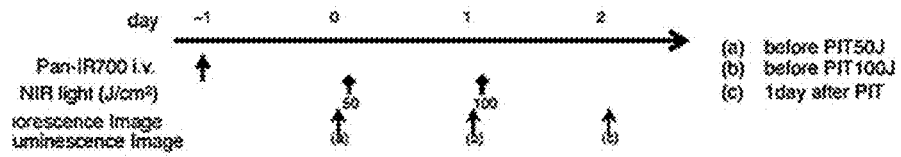
FIGS. 19A-19D show the evaluation of PIT on an in vivo A431-luc-GFP flank tumor. (A) The PIT regimen incorporating repeated NIR light exposures is shown. (B) in vivo GFP/IR700 fluorescence imaging and BLI of bilateral flank tumors in response to PIT. The tumor treated with PIT demonstrated loss of GFP fluorescence and bioluminescence. (C) Quantification of GFP-fluorescence showed a progressive decrease in intensity after repeated PIT eventually resulting in complete loss of signal (n=10 in each group). (D) Bioluminescence was measured as relative light units (RLU), and decreased progressively after PIT eventually resulting in complete loss of RLU (n=10).
Figure 19B:
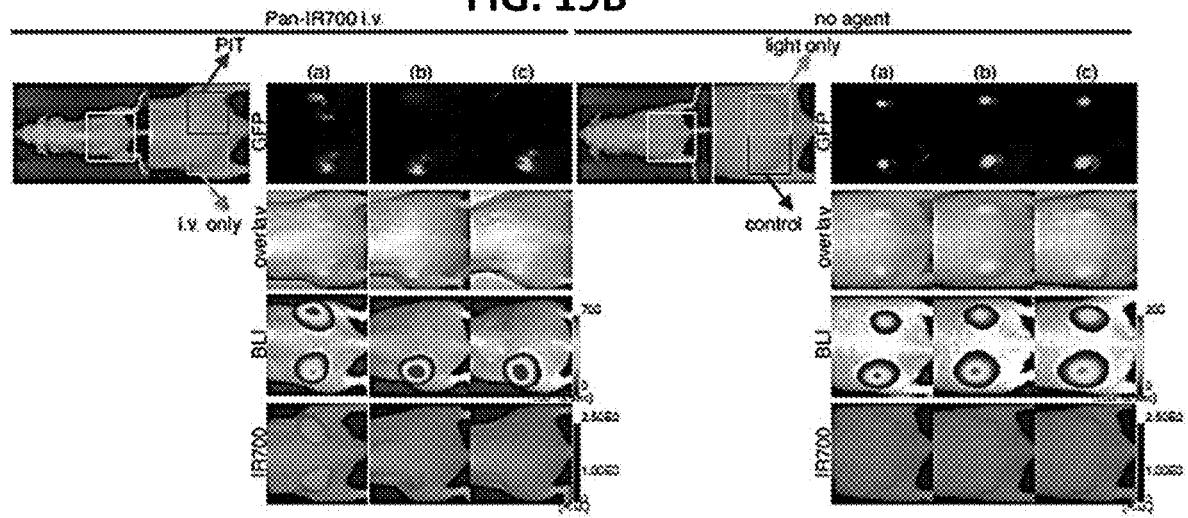
Figure 19C:
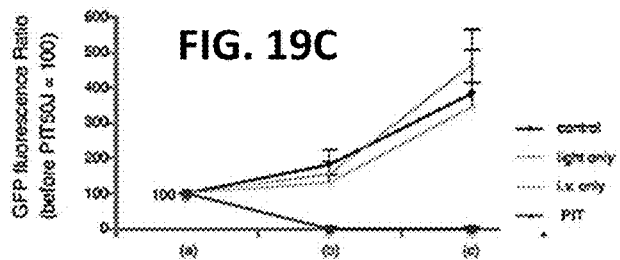
Figure 19D:
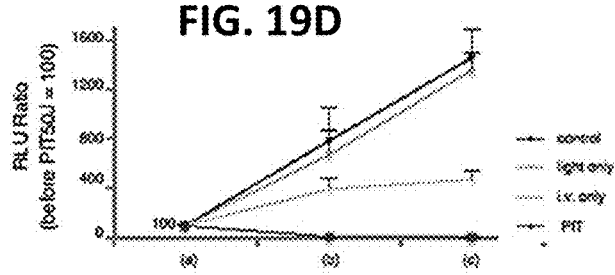
Figure 20:
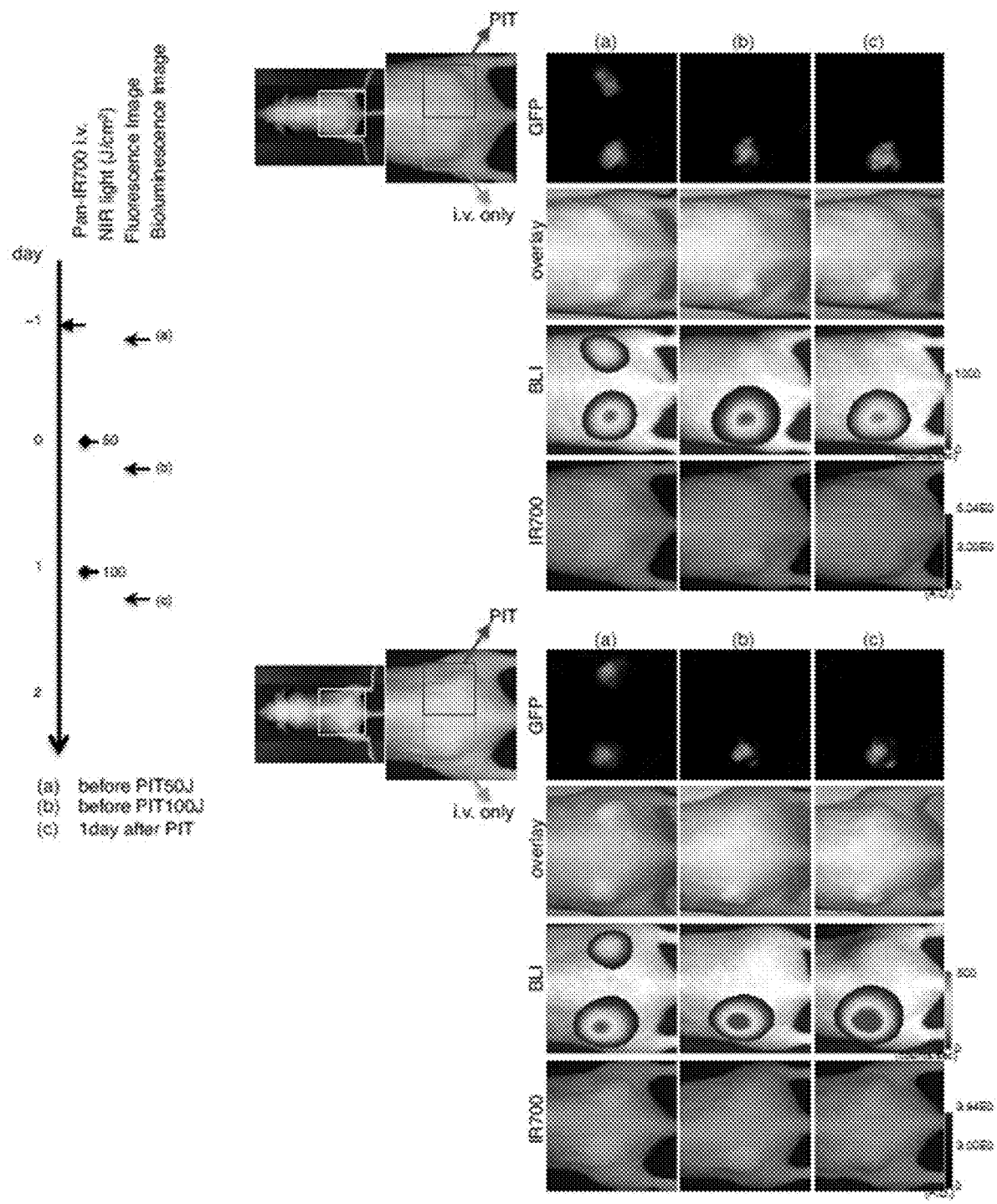
FIG. 20 shows the PIT effect on in vivo A431-luc-GFP flank tumor. in vivo GFP/IR700 fluorescence imaging and BLI of bilateral flank tumors in two additional mice. The tumor treated with PIT demonstrated loss of both GFP fluorescence and bioluminescence after PIT.

PIT caused necrotic cell death in the APC-bound layer of A431-luc-GFP cells in the 3D spheroid (FIG. 16). PIT killing effects on A431-luc-GFP spheroids monitored with GFP fluorescence, BLI and size volumetric, all showed a light-dose dependence (FIGS. 17A-17E). Daily repeated PIT achieved complete eradication of A431-luc-GFP cells within spheroids (FIGS. 18A-18F). These results indicate that repeated PIT could eradicate target-expressing cells growing in 3D spheroids. Finally, the PIT effect was evaluated in a A431-luc-GFP flank tumor model in mice (FIGS. 19A-D and FIG. 20). Repeated PIT (FIG. 19A) led to disappearance of both GFP signal and luciferase activity in A431-luc-GFP tumor (FIG. 19B and FIG. 20) suggesting complete eradication of the A431-luc-GFP tumor (FIGS. 19C-19D). Ex vivo A431-luc-GFP tumor images validated the in vivo results (FIGS. 21A-21B).

Figure 22A:
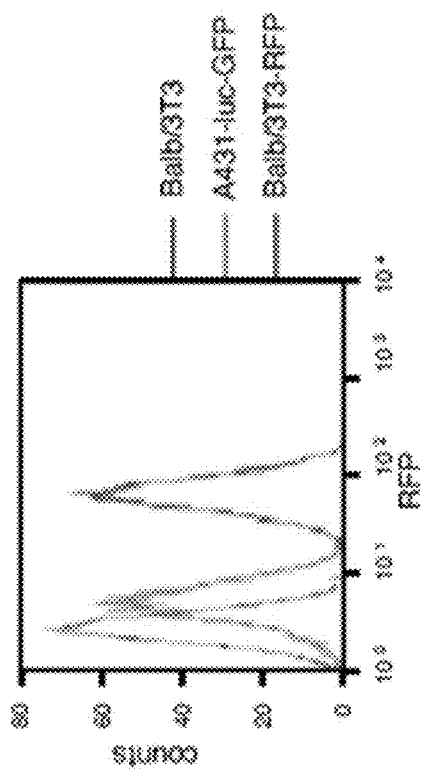
FIGS. 22A-22B show the selective/specific fluorescence in stable cells and specific killing effect of PIT. (A) FACS demonstrates sorting of the two cell lines (A431 and Balb/3T3) by their GFP and RFP fluorescence. (B) Mixture of A431-luc-GFP cells and Balb/3T3-RFP cells were incubated with Pan-IR700 for 6 hr. Baseline and 1 hour post-PIT (2 J/cm2) microscopic images demonstrate specific cell killing of A431-luc-GFP. Bar=20 μm. Membrane damage and necrosis induced by PIT was confirmed by dead cell Cytox staining.
Figure 22B:
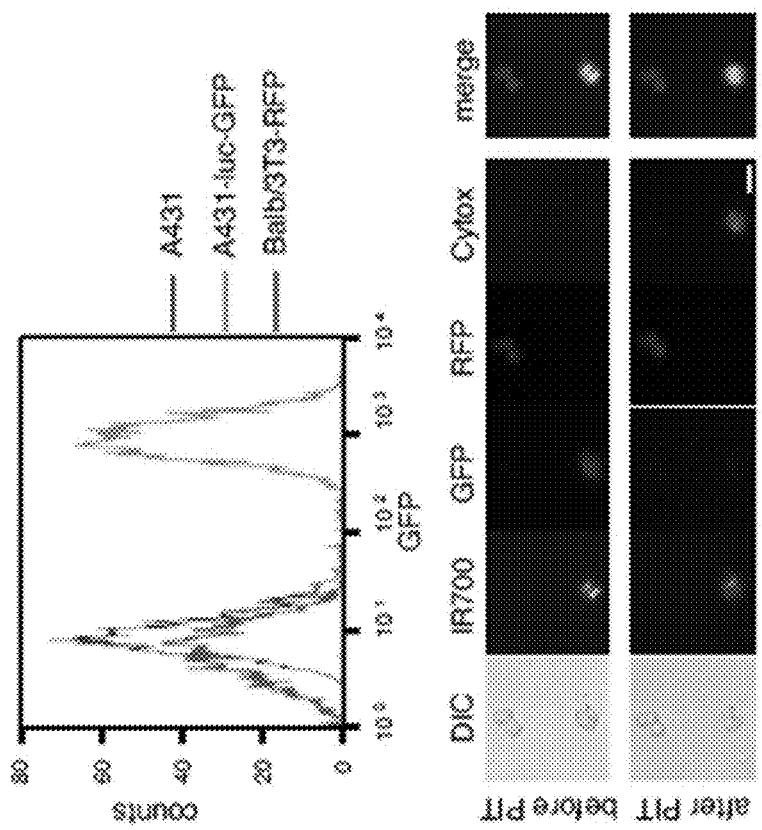
Figure 23B:
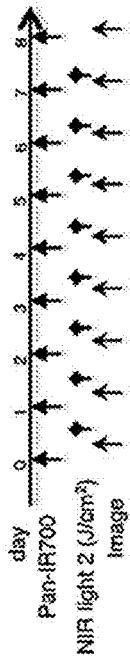
FIGS. 23A-23E show target cell elimination in 2D cell culture. (A) Representative image demonstrates that A431-luc-GFP cells were eliminated 1 hr after PIT. Bar=200 μm. Almost confluent mixed cell culture of A431-luc-GFP and Balb/3T3-RFP was used. Cells were incubated with Pan-IR700 for 6 hr, and observed before and after irradiation with NIR light (2 J/cm2). (B) Repeated PIT (2 J/cm2) regimen is shown (2 J/cm2). (D) Repeated PIT completely eliminated targeted cells with no harm to non-targeted cells, until non-target cells became confluent. 100:10 ratio mixtures of A431-luc-GFP and Balb/3T3-RFP cells were cultured. Bar=200 μm. (D) Quantification of fluorescence ratios showed complete elimination of targeted cells and no effect on non-targeted cells. (n=10 fields in each group) (E) Quantification of luciferase activities (RLU ratio) demonstrates complete target cell elimination (n=10 in each group).
Figure 23D:
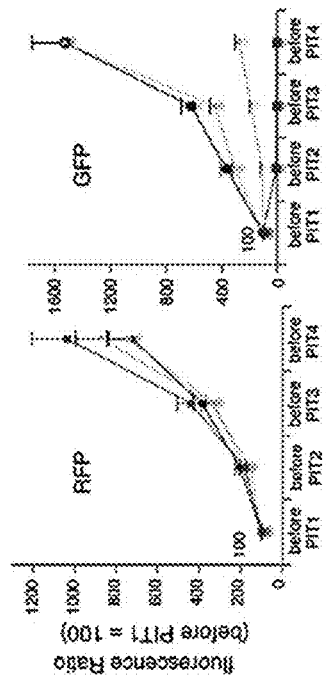
Figure 23E:
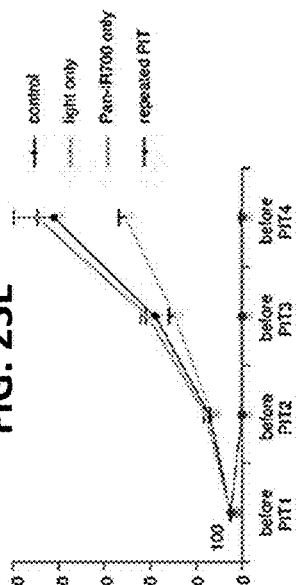
Figure 23A:
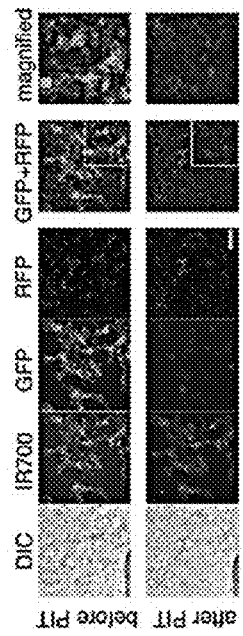
Figure 23C:
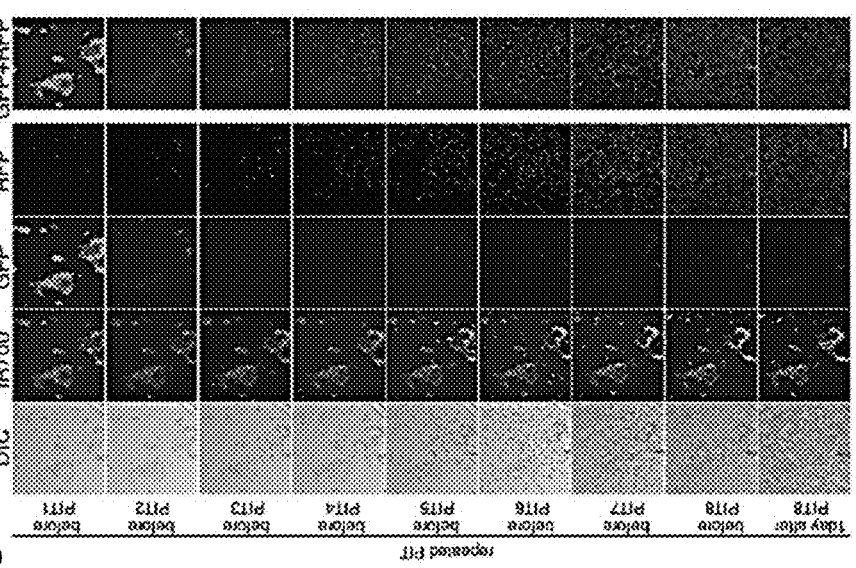

In order to demonstrate selective elimination of target-expressing cells from mixed 2D and 3D cell cultures or mixed tumor models, we used the two previously described cell lines (A431-luc-GFP and Balb/3T3-RFP) (FIG. 22A). Selective cell killing of A431-luc-GFP was documented with Cytox dead staining (FIG. 22B). Elimination of A431-luc-GFP from an almost-confluent 2D mixed cell culture was demonstrated after PIT (FIG. 23A). Repeated PIT (FIG. 23B) led to complete target cell elimination without affecting the non-target cell growth (FIG. 23C and FIGS. 24A-24C). Quantification of cell growth by fluorescence signal and luciferase activity confirmed the selective killing of A431-luc-GFP (FIGS. 23D and 23E).

With PIT, no remarkable change was detected to non-target-expressing 3D spheroid, while target 3D spheroid clearly decreased in size (FIG. 25A). In order to demonstrate target cell elimination from 3D cell culture, a mixed 3D spheroid was established (FIG. 25B). Repeated PIT (FIG. 25A) resulted in complete target cell elimination from the mixed 3D cell culture without damaging non-target cells (FIG. 26B and FIGS. 27A-27C). Each cell population was monitored by fluorescence signal and BLI (FIGS. 26C-26D).

When other target cells were added to the spheroid, appropriately targeted APCs with NIR resulted in their selective elimination from 3D mixed spheroids. For instance, targeted HER2 and PSMA APCs in a mixed model of 3T3/HER2-luc-GFP and PC3-PIP-luc-GFP cells resulted in the selective elimination of these targeted cells in each case (FIGS. 28A and 28B).

Figure 30A:
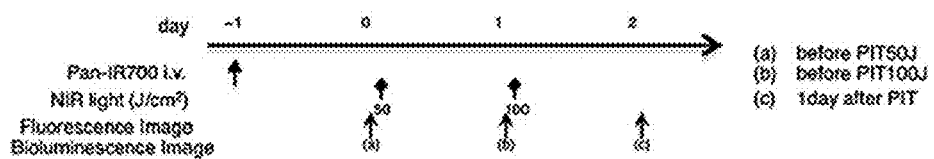
FIGS. 30A-30E show target cell elimination within a mixed tumor model in vivo. (A) PIT (2 J/cm2) regimen is shown. (B) Repeated PIT completely eliminated target cells from mixed tumors in vivo. (C) Quantification of fluorescence ratios showed complete elimination of target cells in mixed tumors. (n=10 in each group). (D) Quantification of luciferase activities (RLU ratio) demonstrated complete elimination of target cells in vivo. (n=10 in each group). (E) Representative image of ex vivo tumors showed complete elimination of target cells from mixed tumors.
Figure 30B:
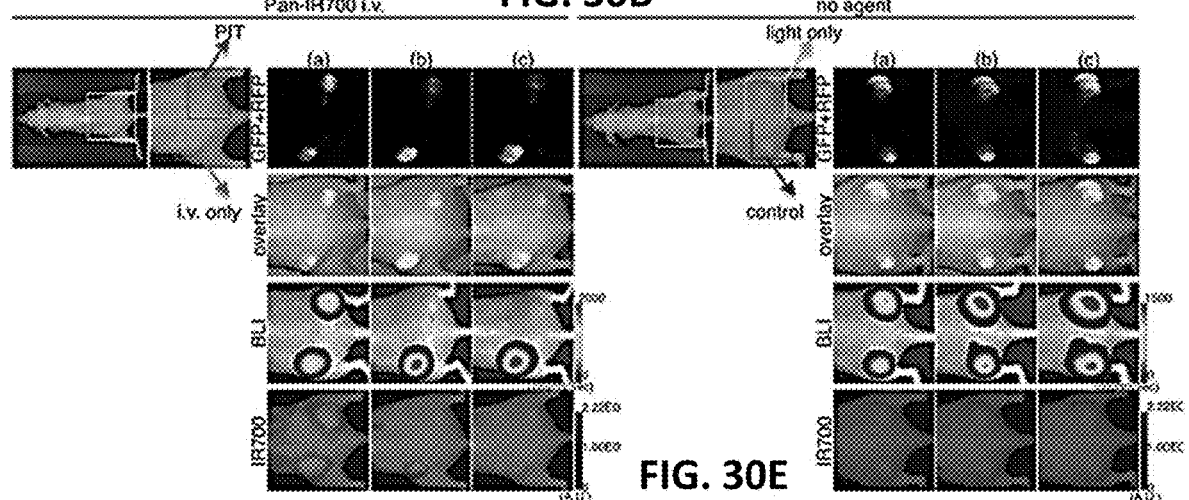
Figure 30C:
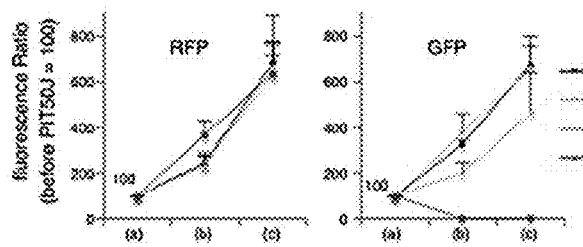
Figure 30D:
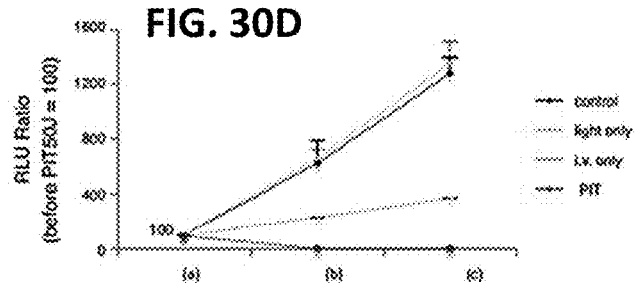
Figure 30E:
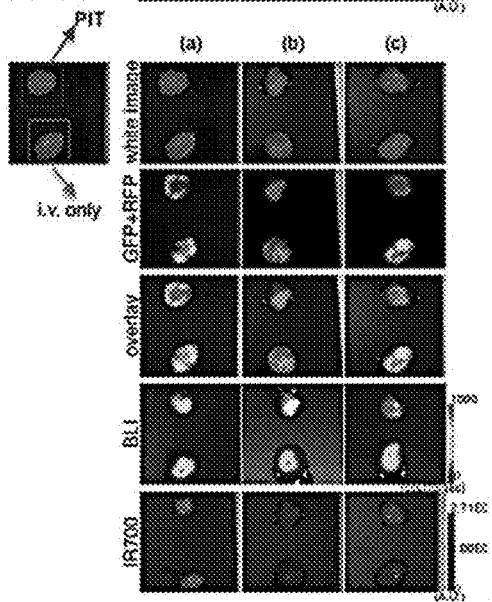
Figure 31:
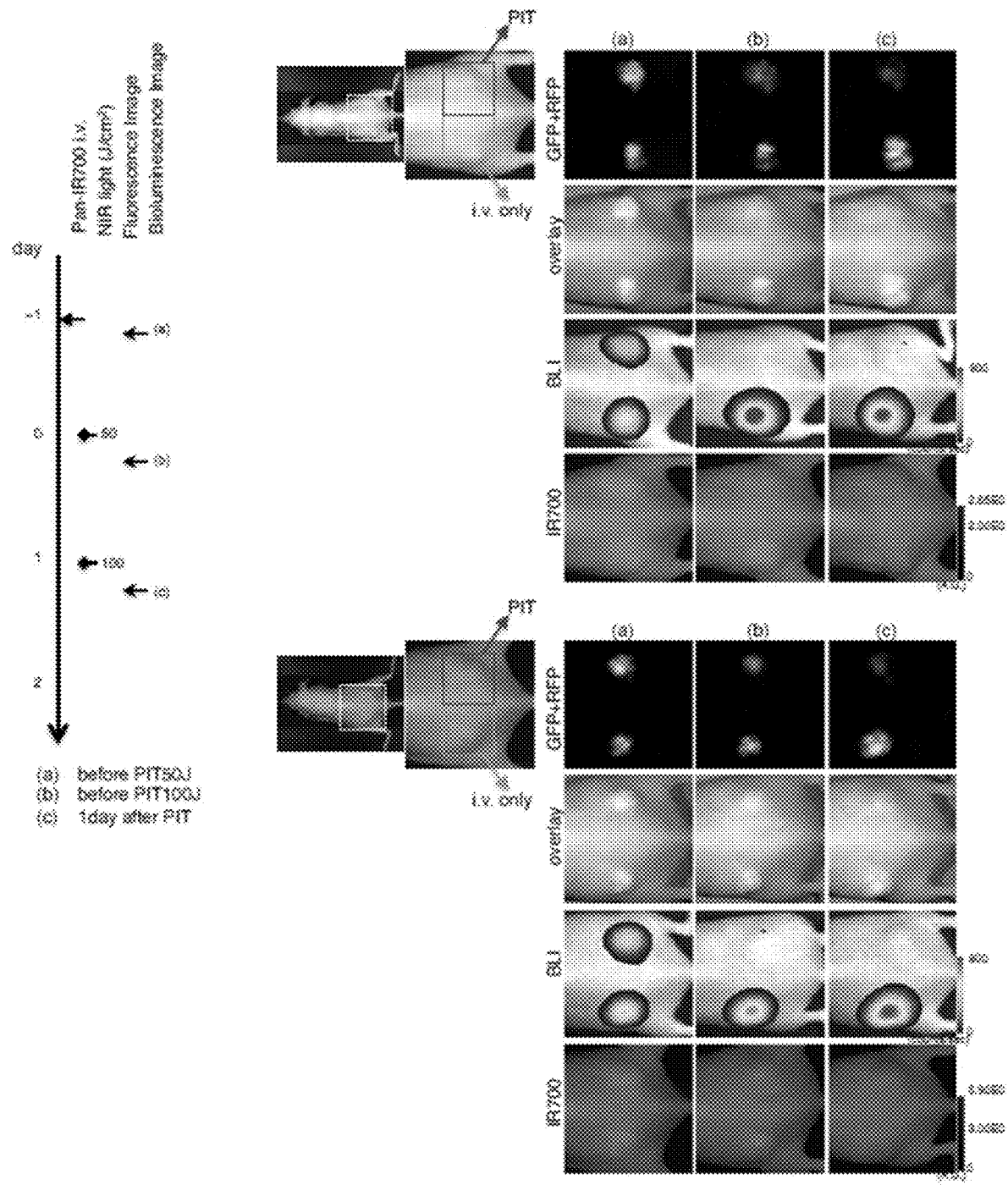
FIG. 31 shows target cell elimination in vivo. Repeated PIT completely eliminated target cells in mixed tumors. In vivo GFP/IR700 fluorescence imaging and BLI of bilateral flank tumor (2 additional mice). The tumor treated by PIT demonstrated disappearance of both GFP fluorescence and bioluminescence after PIT.
Figure 32A:
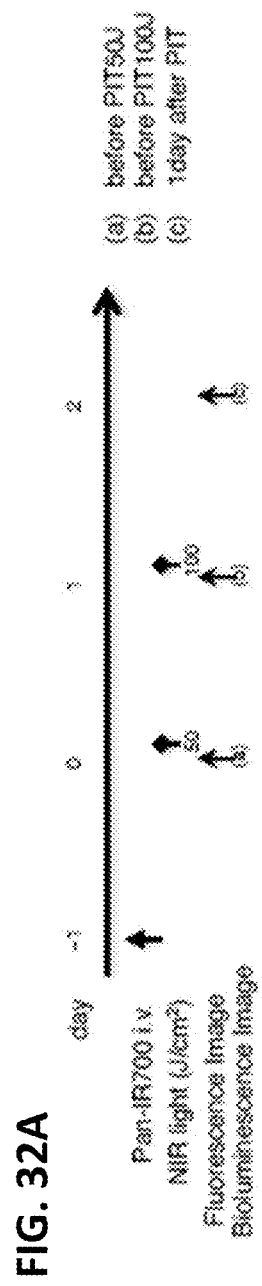
FIGS. 32A-32B show cell elimination on ex vivo mixed tumor (control tumor). (A) The PIT regimen incorporating repeated NIR light exposures is shown. (B) Ex vivo GFP/IR700 fluorescence imaging and BLI of a mixed tumor in response to PIT. ex vivo images of control tumors are shown.
Figure 32B:
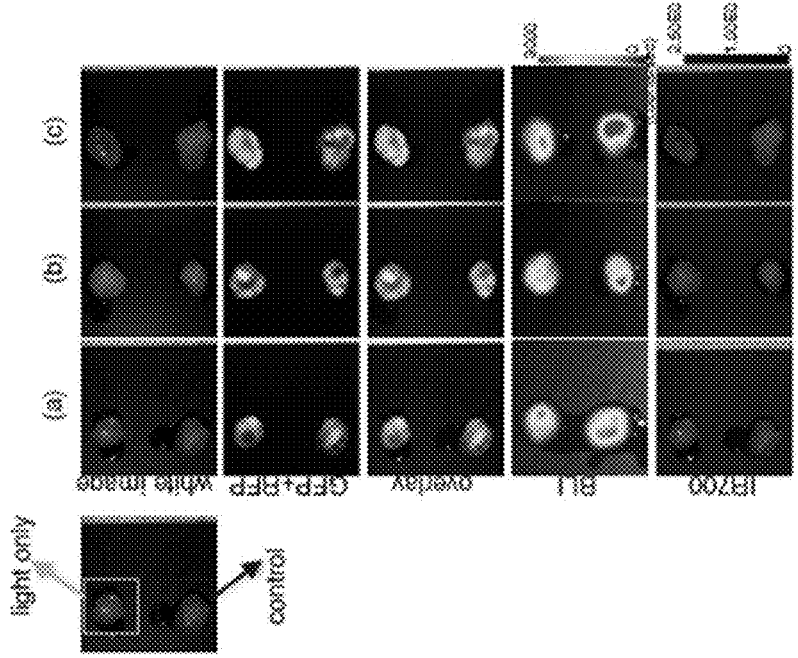

Finally, complete target cell elimination within a mixed tumor implanted in the flank of a mouse was demonstrated. As with the cell cultures, non-target-expressing tumor cells showed minimal damage, while target-expressing cells were eradicated (FIGS. 29A and 29B). Repeated PIT (FIG. 30A) led to complete elimination of target-expressing cells from mixed tumors in vivo with minimal damage to non-target cells (FIGS. 30B and 31). Quantification of cell population was achieved with fluorescence signal and luciferase activity (FIGS. 30C, 30D). Complete cell elimination from mixed tumors was also confirmed on ex vivo images (FIGS. 30E and 32A-32B).

In conclusion, this example shows that the disclosed methods can be used to selectively remove target cells from a mixed 2D culture, a mixed 3D spheroid and a mixed in vivo tumor. Thus, the disclosed methods can be used for selectively eliminating cells from cell mixtures, spheroids and in vivo tumors.

In view of the many possible embodiments to which the principles of the disclosure may be applied, it should be recognized that illustrated embodiments are only examples of the disclosure and should not be considered a limitation on the scope of the invention. Rather, the scope of the invention is defined by the following claims. We therefore claim as our invention all that comes within the scope and spirit of these claims.

We claim:

1. A method of removing a target from a sample, comprising:
    contacting the sample with a phthalocyanine IRDye 700DX (IR700) conjugated to a molecule (IR700-molecule conjugate) to form an IR700-molecule conjugate-target complex, wherein the molecule of the IR700-molecule conjugate comprises a specific binding agent that specifically binds to the target;
    irradiating the sample after the contacting step, at a wavelength of 660 to 710 nm and at a dose of at least 1 J cm$^{-2}$ under conditions sufficient for cleaving and removing one or both of the hydrophilic side chains of the IR700 and generating a hydrophobic IR700-molecule conjugate-target complex;
    incubating the sample, after the contacting step under conditions that allow the hydrophobic IR700-molecule conjugate-target complex to aggregate; and
    separating the aggregate of the hydrophobic IR700-molecule conjugate-target complex from the sample, thereby removing the target from the sample, wherein the target is a protein, peptide, lectin, carbohydrate, metal, nucleic acid molecule, recreational drug, small organic molecule, pathogen, or spore.

2. The method of claim 1, wherein the IR700-molecule conjugate comprises an IR700-antibody conjugate, IR700-antibody fragment conjugate, IR700-antibody mimetic molecule conjugate, IR700-hapten conjugate, IR700-lectin conjugate, IR700-protein conjugate, IR700-nucleic acid molecule conjugate, or IR700-functional nucleic acid conjugate,
    wherein the antibody, antibody fragment, antibody mimetic molecule, hapten, lectin, protein, nucleic acid molecule, and functional nucleic acid specifically bind to the target molecule.

3. The method of claim 1, wherein the sample is a food sample, environmental sample, reactor sample, fermentation sample, or sample obtained from a subject.

4. The method of claim 1, wherein the sample is irradiated at a wavelength of 690 nm+/−20 nm or 690 nm+/−4 nm.

5. The method of claim 1, wherein incubating the sample comprises centrifuging the sample to form a pellet.

6. The method of claim 1, wherein incubating the sample comprises allowing the hydrophobic IR700-molecule conjugate-target complex to settle to the bottom of a container.

7. The method of claim 1, wherein separating the hydrophobic IR700-molecule conjugate-target complex from the sample comprises collecting a supernatant after allowing the hydrophobic IR700-molecule conjugate-target complex to aggregate.

8. The method of claim 1, further comprising measuring the target removed from the sample.

9. The method of claim 1, wherein the sample is irradiated at a wavelength of 660 to 710 nm and at a dose of at least 4 J cm$^2$.

10. The method of claim 1, wherein the sample is irradiated at a wavelength of 660 to 710 nm and at a dose of at least 100 J cm$^2$.

11. The method of claim 1, wherein the method comprises irradiating the sample at a wavelength of 680 to 690 nm and at a dose of at least 4 J cm$^2$.

12. A method of removing and detecting a target from a subject, comprising:
    administering to the subject systemically, inhaltionally or intranasally, a therapeutically effective amount of a phthalocyanine IRDye 700DX (IR700) conjugated to a molecule (IR700-molecule), wherein the molecule comprises a specific binding agent that specifically binds to the target;
    allowing the administered IR700-molecule to bind to the target via the specific binding agent;
    irradiating the subject after the administering step, at a wavelength of 660 nm to 710 nm and at a dose of at least 4 J cm$^{-2}$ under conditions sufficient for cleaving and removing one or both of the hydrophilic side chains of the IR700 and forming a hydrophobic IR700-molecule-target complex;
    allowing the hydrophobic IR700-molecule-target complex to aggregate in the subject;
    subsequently, after allowing to aggregate, obtaining from the subject a urine or bowel movement sample comprising the hydrophobic IR700-molecule-target complex aggregate; and
    detecting in the urine or bowel movement sample the hydrophobic IR700-molecule-target complex aggregate, wherein detection of the aggregate indicates detection of the removed target from the subject.

13. The method of claim 12, wherein the target is a protein, peptide, lectin, carbohydrate, metal, nucleic acid molecule, small organic molecule, recreational drug, pathogen, spore, or cell.

14. The method of claim 13, wherein the target cell is a cell in a tumor.

15. The method of claim 14, wherein the cell in the tumor is a tumor cell, immune cell, or cancer stem cell.

16. The method of claim 14, wherein the target cell is a negative regulatory T-cell.

17. The method of claim 16, wherein the negative regulatory T-cell is a CD4$^+$CD25$^+$FoxP3$^+$ T cell, and the IR700-molecule conjugate comprises an anti-CD25 or anti-CLTA4 antibody.

18. The method of claim 13, wherein the target cell is a lymphocyte, dendritic cell, or macrophage.

19. The method of claim 12, wherein the IR700-molecule conjugate comprises an IR700-antibody conjugate, IR700-antibody fragment conjugate, IR700-antibody mimetic molecule conjugate, IR700-hapten conjugate, IR700-lectin conjugate, IR700-protein conjugate, IR700-nucleic acid molecule conjugate, or IR700-functional nucleic acid conjugate,
    wherein the antibody, antibody fragment, antibody mimetic molecule, hapten, lectin, protein, nucleic acid molecule, and functional nucleic acid specifically bind to the target molecule.

20. The method of claim 13, wherein the subject is irradiated at a wavelength of 690 nm+/−20 nm or 690 nm+/−4 nm.

21. The method of claim 12, wherein irradiating the subject comprises using a device worn by the subject, wherein the device comprises a near infrared (NIR) light emitting diode (LED).

22. The method of claim 12, wherein the subject has a cancer of the breast, liver, kidney, uterus, colon, ovary, prostate, pancreas, brain, cervix, bone, skin, or lung.

\* \* \* \* \*